US011180740B2

(12) United States Patent
Yu et al.

(10) Patent No.: US 11,180,740 B2
(45) Date of Patent: Nov. 23, 2021

(54) SYNTHESIS OF GLUCAN COMPRISING BETA-1,3 GLYCOSIDIC LINKAGES WITH BETA-1,3-GLUCAN PHOSPHORYLASE ENZYMES

(71) Applicant: DANISCO US INC, Palo Alto, CA (US)

(72) Inventors: Zheyong Yu, Shanghai (CN); Slavko Kralj, Copenhagen (DK); Natnael Behabtu, Wilmington, DE (US); Zhenghong Zhang, Shanghai (CN); Laurie A Howe, Bear, DE (US)

(73) Assignee: DANISCO US INC, Palo Alto, CA (US)

( * ) Notice: Subject to any disclaimer, the term of this patent is extended or adjusted under 35 U.S.C. 154(b) by 0 days.

(21) Appl. No.: 16/383,820

(22) Filed: Apr. 15, 2019

(65) Prior Publication Data
US 2019/0322990 A1 Oct. 24, 2019

(30) Foreign Application Priority Data

Apr. 23, 2018 (WO) ................ PCT/CN2018/084036

(51) Int. Cl.
*C12N 9/10* (2006.01)
*C12P 19/04* (2006.01)
*C08B 37/00* (2006.01)

(52) U.S. Cl.
CPC ........ *C12N 9/1051* (2013.01); *C08B 37/0003* (2013.01); *C12P 19/04* (2013.01); *C12Y 204/01097* (2013.01)

(58) Field of Classification Search
CPC .................................................. C08B 37/0024
USPC ....................................................... 435/194
See application file for complete search history.

(56) References Cited

U.S. PATENT DOCUMENTS

| | | | |
|---|---|---|---|
| 5,254,174 | A | 10/1993 | Hansen et al. |
| 5,403,604 | A | 4/1995 | Black, Jr. et al. |
| 5,716,837 | A | 2/1998 | Barry et al. |
| 6,454,946 | B1 | 9/2002 | DeFrees |
| 7,229,801 | B2 | 6/2007 | Fujii et al. |
| 7,968,309 | B2 | 6/2011 | Fujii et al. |
| 8,530,202 | B2 | 9/2013 | Isono et al. |
| 8,889,379 | B2 | 11/2014 | Tran et al. |
| 9,909,119 | B2 | 3/2018 | Kishimoto et al. |
| 9,913,876 | B2 | 3/2018 | Walker |
| 9,932,503 | B2 | 4/2018 | Harrington et al. |
| 2002/0133849 | A1 | 9/2002 | Kossmann et al. |
| 2013/0059340 | A1 | 3/2013 | Tran et al. |
| 2014/0057323 | A1 | 2/2014 | Cate et al. |
| 2014/0087435 | A1 | 3/2014 | Chen et al. |
| 2017/0166938 | A1 | 6/2017 | Nagy et al. |
| 2017/0327857 | A1 | 11/2017 | Behabtu et al. |

FOREIGN PATENT DOCUMENTS

EP 2397557 A1 12/2011

OTHER PUBLICATIONS

Moreno et al, 2014 GenBank Database Acc#ETT58856. Alignment with SEQ ID No. 6.*
Beno, 2017 UniProt Database Acc#A0A1R0X211. Alignment with SEQ ID No. 6.*
Kitakoa et al, Characterization of a Bacterial Laminaribiose Phosphorylase. Biosci. Biotechnol. Biochem., 76 (2), 343-348, 2012.*
Kuhaudomlarp et al., Identification of Euglena gracilis B-1,3-glucan phosphorylase and establishment of a new glycoside hydrolase (GH) family GH149. J. Biol. Chem. (2018) 293(8) 2865-2876.*
Yamamoto et al, Purification and Characterization of 1,3-β-D-Glucan Phosphorylase from Ochromonas danica. Biosci. Biotechnol. Biochem., 77 (9), 1949-1954, 2013.*
Brownfield, L. et al., 2009, Biochemical and Molecular Properties of Biosynthetic Enzymes for (1,3)-Beta-Glucans in Embryophytes, Chlorophytes and Rhodophytes, in Antony Bacic et al., Eds., Chemistry, Biochemistry, and Biology of 1-3 Beta Glucans and Related Polysaccharides, Academic Press, Burlington, MA.
Nogami, S. et al., 2009, Biosynthetic Enzymes for (1-3)-Beta-Glucans, (1-3;1-6)-Beta-Glucans from Yeasts: Biochemical Properties and Molecular Biology, in Antony Bacic et al., Eds., Chemistry, Biochemistry, and Biology of 1-3 Beta Glucans and Related Polysaccharides, Academic Press, Burlington, MA.
Bulone, V., 2009, Biosynthetic Enzymes for (1,3)-Beta-Glucans and (1,3;1,6)-Beta-Glucans in Protozoans and Chromistans: Biochemical Characterization and Molecular Biology, in Antony Bacic et al., Eds., Chemistry, Biochemistry, and Biology of 1-3 Beta Glucans and Related Polysaccharides, Academic Press, Burlington, MA.
Stanisich, V. A., 2009, Enzymology and Molecular Genetics of Biosynthetic Enzymes for (1,3)-Beta-Glucans: Prokaryotes, in Antony Bacic et al., Eds., Chemistry, Biochemistry, and Biology of 1-3 Beta Glucans and Related Polysaccharides, Academic Press, Burlington, MA.
Stone, B. A. (2009, Chemistry of Beta-Glucans, In Antony Bacic et al., Eds., Chemistry, Biochemistry, and Biology of 1-3 Beta Glucans and Related Polysaccharides, Academic Press, Burlington, MA.
Kitakoa et al. (2012, Biosci. Biotechnol. Biochem. 76:343-348).
Kitakoa et al. (1993, Arch. Biochem. Biophys. 304:508-514).
Nihira et al. (2012, Carb. Res. 361:49-54).
Hamura et al. (2012, Biosci. Biotechnol. Biochem. 76:812-818).
Reichenbecher et al. (1997, Eur. J. Biochem. 247:262-267).
Miyamoto and Tamari, 1973, Agr. Biol. Chem. 37:1253-1260.
Franck (2003, Ann. Trans. Nordic Rheol. Soc. 11:95-100).
Catarino et al. (2008, J. Membrane Science 312:34-40).
Machado et al. (2016, J. Food Eng. 180:120-128).
Legentil et al., 2015, Molecules 20:9745-9766.
Mishima et al., 2009, J. Biol. Chem. 284:28687-28697.
Ogawa et al., 1973, Carbohydr. Res. 29:397-403.
Albrecht et al_Phytochemistry_1971, 10: 1293-1298.
Beta-1,3 poster EUROCARB2017.

(Continued)

*Primary Examiner* — Sheridan Swope

(57) ABSTRACT

Reaction compositions are disclosed herein comprising at least water, alpha-glucose-1-phosphate (alpha-G1P), an acceptor molecule, and a beta-1,3-glucan phosphorylase enzyme. These reactions can synthesize oligosaccharides and polysaccharides with beta-1,3 glycosidic linkages. Further disclosed are methods of isolating beta-1,3-glucan.

24 Claims, No Drawings

Specification includes a Sequence Listing.

(56) References Cited

OTHER PUBLICATIONS

Gidley et al_Physico-chemistry of 1,3-Beta-Glucans_Chap 2.2_ 2009, 47-118.
Goldemberg et al_J Biol Chem_1966, 241:45-51.
Kuge et al_AgricBiolChem_1977, 41, 7: 1315-1316.
Kuhaudomlarp et al_J Biol Chem_2018, 293, 8: 2865-2876.
Marechal I_BiochimicaBiophysicaActa_1967, 146: 417-430.
Marechal II_BiochimicaBiophysicaActa_1967, 146: 431-442.
O'Neill et al_Carb Res_2015, 403: 23-37.
Santek et al_Eng Life Sci_2009, 9, 1: 23-28.
Yamamoto, Y, et al, Purification and Characterization of 1,3-beta-D-Glucan Phosphorylase from Ochromonas danica, Bioscicence, Biotechnology, and Biochemistry, vol. 77, No. 9, 2013, pp. 1949-1954, XP002793269.
Database UniProt [Online], Den Bakker, H.C. et al., "Full= Cellobiose phosphorylase" database accession No. A0A089M2A2, Mar. 28, 2018, XP002793270.
Database UniProt [Online], Isono, N. et al, "Full=1,3-beta-D-glucan phosphorylase, EC=2.4.1.97", database accession No. A0A143T210, Mar. 28, 2018, XP002793271.
Database UniProt [Online], Isono, N. et al., "Full=1,3-beta-D-glucan phosphorylase, EC=2.4.1.97", database accession No. A0A143T443, Mar. 28, 2018, XP002793272.

* cited by examiner

SEQUENCE LISTING

```
<160> NUMBER OF SEQ ID NOS: 24

<210> SEQ ID NO 1
<211> LENGTH: 3264
<212> TYPE: DNA
<213> ORGANISM: Paenibacillus stellifer DSM 14472

<400> SEQUENCE: 1
atgccagcct attatatgga taatcagtat tttgtcatag aggaattcga taaagccaag     60
accttcgcca gcttcctgcc cggcctagcc ggaccgaagg gcatcccgat gtggacgttc    120
tacgtcaacc ggggccaggg aattgcaagc ttcggcatcc gggacaagaa ttcgcccatc    180
atggagttct ccccggctaa catcagctac aaaaatgtgc cgctcagcgg cttccggaca    240
ttcatcaagc ttggcggcgc cgtctacgaa ccgttccagg atcaaggcga ggactcttct    300
atccggcgga cgatgtcaat cgggttaaac gagctagtga ttgaagagac gaaccatact    360
ctgaatcttc aggtgaaaat cgtgtacttc aacgttccgg gcgacgggtt cgccgcgctg    420
gccaggcaca cggaaatcac gaacctgtcg gcatcgccga tgccgctcga ggtgctggac    480
ggcctgcccg agcttcttcc ctatggaatc gacaatgccg gatacaagga aatgggcaat    540
ctgcttcgca gctggatgga ggtctacaat ctggagaacg ccgtgccatt tttcaagctc    600
cgctccagta ccaaggatga ggccgaagtc agcgagatta agggagggca tttctatctt    660
tcgttcagcg acgaggaaga gcttcttccg ccgatcgtcg attatgaagt catcttcgga    720
cataatactt ctctcgtgta tccggcctca tttgcgcgcg cttccctaga acaactcgga    780
gcgatgccgc agattaccgc gaacaaggtt ccgtgcgcct tagcggcgc ggcgggcaag    840 ctgggaccgg gcgagagcct gaacctgtac gcgatgatcg gacatacacg cgatatcgga    900
agcatccagt cgcagaccgg acgtctctgc cgggcggaat acttccgaac caaacgggag    960
```

```
gaggctgcca gaatggcgga acaacttacc ggcgatatcg cgacttccac ttcgtcaacg    1020
atgttcgacg cttactgccg gcagagctat ctcgacaata tgctgcgcgg cggctatccc    1080
gtggtattcg gccaagggca ggagaccaag atctatcatt tattttcccg gaagcatggg    1140
gatctggagc gcgattataa cttttttctca ctggctccgg aatattattc caaggcaac    1200 ggcaatttcc gggatatgaa ccagaaccgc cgcaacgacg tcttgttcca tccggaagcg    1260
ggcgcattca atatttatat gttcttcagc cttattcagg cggacggcta taatccgctg    1320
caggtcaagg gcagcacctt ccaagtgccg gaggaacggg cagcggagct cgccagctta    1380
ctggaacaag cggtaggcag ccaccgccgg gaactgtccg ctatagcggc caaaccgttt    1440
accccggggc agatcattca ttacctctgc gatcatgaga ttatgcttaa cgtgagcgaa    1500
gaggagtttc tggataagct gctgggtctg tccgcgcaaa atattgaagc aagctttgga    1560
gaaggctact ggattgatca ctggacctac aatatggatc tggtggacag ctaccgttct    1620 gttttttccgg ataaaatgga ggagctgctg tatacgcctg gaacctgccg cttcttcgac    1680
agccccgttc gcgtgctgcc gcgcagcgaa aagacggtgc ttaaggatgg caaggtacgc    1740
caatatggct ctgccgtgca tgatgaagag aagctggagc gccttggcgg cggaatgtcc    1800
gacacccgct ggctgagaac gcagcatgga acaggcgagg tctaccgtac cgatctgttc    1860
gccaaaatgc tgtccctggc cctgatcaaa atgacgacgc tggacccttaa cggcatgggc    1920 attgagatgg aagggaataa ccgggctgg aatgatgcga tgaacgggct tcccggtctg    1980
ttcggctccg gtatggggga gacctatgaa ctgaagcgtc tagtgctgtt catactggaa    2040
gcgctatccg gaatgccggg aggggcagtt gtctccgggg acccgggaga ttcagggctt    2100
gccggacgga aggtccgcct gcctttggaa atggcggagc tgctgtcgga gacggactcg    2160
gttctatccc gccgggagag cggggacatc tccgacctgg aatgctggga tctgctggcg    2220
acggcgcgcg agcgttaccg cgagagtatc cggttcggcc tgtccggcga cgagcaggag    2280
attgtctttg cggcattgga gccggtcttc aagcggtttc tggggcggct gaatgagggg    2340
atcgcgaagg ccgtcaagct tggcgggggc cttgttccca cctacttccg cttcgaggca    2400
gaggactacg agcctctaaa gggcggtgac ggaggcccgg ttatcagctc ttacggactt    2460
ccggtagtat cggtgagtcg gttccgcgcc gaagcgcttc cggcgtttct ggaagggccg    2520
gtgcatgggc tgaagcttgc ggaaagcaag gaggaagcac agggtattta ccggcggtg    2580 cgaagcagcg gcctgtacga cgagaagctc ggcatgtaca aaacctccgt cagcctggag    2640
cagcagccgc aggaaatcgg ccgcatccgc gcgttcaccc cgggctggct ggagcgggaa    2700
tcgatattcc tgcacatgtc ctacaaatat gtccttgagc tgctgaagac cgggctgacc    2760
gggacgttct atgaagaatt caagcgcgcg ctgatcccgt tccaggaccc cgccgtctac    2820
gggcgcagca cgctggagaa ttcctccttc ctcgccagca cgtcaaccc cgaccccggc    2880 gtgcacggcc gcggctttgt cgcccgcctg agcggctcga ctgcggagtt cctgagcatg    2940
tggtcgctca tgatggcggg aagccgtccc ttccggttga gtggagacgg agaccttgtg    3000
ctggagcttg caccgcgcgct tccggctgg ctgttcaagg atgacggccg tctctcgttc    3060
cggttccttg gctcggtccg cgtgacttac ctcaatgagc ggcgggccga tacgttcgga    3120
gagaactgcg ccgctatccg gcgaattagc gtcaaagacg gcgccgggaa cacgctgacc    3180
gttgagggaa gcgtactgtc cggcaagctg gctgaagaca tccggggccgg acggtacacg    3240 gagcttgagg ttgtgctgga atag                                            3264
```

-continued

```
<210> SEQ ID NO 2
<211> LENGTH: 1087
<212> TYPE: PRT
<213> ORGANISM: Paenibacillus stellifer DSM 14472

<400> SEQUENCE: 2
```

Met Pro Ala Tyr Tyr Met Asp Asn Gln Tyr Phe Val Ile Glu Glu Phe
1               5                   10                  15

Asp Lys Ala Lys Thr Phe Ala Ser Phe Leu Pro Gly Leu Ala Gly Pro
            20                  25                  30

Lys Gly Ile Pro Met Trp Thr Phe Tyr Val Asn Arg Gly Gln Gly Ile
        35                  40                  45

Ala Ser Phe Gly Ile Arg Asp Lys Asn Ser Pro Ile Met Glu Phe Ser
    50                  55                  60

Pro Ala Asn Ile Ser Tyr Lys Asn Val Pro Leu Ser Gly Phe Arg Thr
65                  70                  75                  80

Phe Ile Lys Leu Gly Gly Ala Val Tyr Glu Pro Phe Gln Asp Gln Gly
                85                  90                  95

Glu Asp Ser Ser Ile Arg Arg Thr Met Ser Ile Gly Leu Asn Glu Leu
            100                 105                 110

Val Ile Glu Thr Asn His Thr Leu Asn Leu Gln Val Lys Ile Val
            115                 120                 125

Tyr Phe Asn Val Pro Gly Asp Gly Phe Ala Ala Leu Ala Arg His Thr
    130                 135                 140

Glu Ile Thr Asn Leu Ser Ala Ser Pro Met Pro Leu Glu Val Leu Asp
145                 150                 155                 160

Gly Leu Pro Glu Leu Leu Pro Tyr Gly Ile Asp Asn Ala Gly Tyr Lys
                165                 170                 175

Glu Met Gly Asn Leu Leu Arg Ser Trp Met Glu Val Tyr Asn Leu Glu
            180                 185                 190

Asn Ala Val Pro Phe Phe Lys Leu Arg Ser Ser Thr Lys Asp Glu Ala
        195                 200                 205

Glu Val Ser Glu Ile Lys Gly Gly His Phe Tyr Leu Ser Phe Ser Asp
    210                 215                 220

Glu Glu Glu Leu Leu Pro Pro Ile Val Asp Tyr Glu Val Ile Phe Gly
225                 230                 235                 240

His Asn Thr Ser Leu Val Tyr Pro Ala Ser Phe Ala Arg Ala Ser Leu
                245                 250                 255

Glu Gln Leu Gly Ala Met Pro Gln Ile Thr Ala Asn Lys Val Pro Cys
            260                 265                 270

Ala Phe Ser Gly Ala Ala Gly Lys Leu Gly Pro Gly Glu Ser Leu Asn
        275                 280                 285

Leu Tyr Ala Met Ile Gly His Thr Arg Asp Ile Gly Ser Ile Gln Ser
    290                 295                 300

Gln Thr Gly Arg Leu Cys Arg Ala Glu Tyr Phe Arg Thr Lys Arg Glu
305                 310                 315                 320

Glu Ala Ala Arg Met Ala Glu Gln Leu Thr Gly Asp Ile Ala Thr Ser
                325                 330                 335

Thr Ser Thr Met Phe Asp Ala Tyr Cys Arg Gln Ser Tyr Leu Asp
            340                 345                 350

Asn Met Leu Arg Gly Gly Tyr Pro Val Val Phe Gly Gln Gly Gln Glu
        355                 360                 365

Thr Lys Ile Tyr His Leu Phe Ser Arg Lys His Gly Asp Leu Glu Arg
    370                 375                 380

```
Asp Tyr Asn Phe Phe Ser Leu Ala Pro Glu Tyr Tyr Ser Gln Gly Asn
385                 390                 395                 400

Gly Asn Phe Arg Asp Met Asn Gln Asn Arg Arg Asn Asp Val Leu Phe
            405                 410                 415

His Pro Glu Ala Gly Ala Phe Asn Ile Tyr Met Phe Phe Ser Leu Ile
        420                 425                 430

Gln Ala Asp Gly Tyr Asn Pro Leu Gln Val Lys Gly Ser Thr Phe Gln
            435                 440                 445

Val Pro Glu Glu Arg Ala Ala Glu Leu Ala Ser Leu Leu Glu Gln Ala
    450                 455                 460

Val Gly Ser His Arg Arg Glu Leu Ser Ala Ile Ala Ala Lys Pro Phe
465                 470                 475                 480

Thr Pro Gly Gln Ile Ile His Tyr Leu Cys Asp His Glu Ile Met Leu
            485                 490                 495

Asn Val Ser Glu Glu Phe Leu Asp Lys Leu Leu Gly Leu Ser Ala
            500                 505                 510

Gln Asn Ile Glu Ala Ser Phe Gly Glu Gly Tyr Trp Ile Asp His Trp
            515                 520                 525

Thr Tyr Asn Met Asp Leu Val Asp Ser Tyr Arg Ser Val Phe Pro Asp
    530                 535                 540

Lys Met Glu Glu Leu Leu Tyr Thr Pro Gly Thr Cys Arg Phe Phe Asp
545                 550                 555                 560

Ser Pro Val Arg Val Leu Pro Arg Ser Glu Lys Thr Val Leu Lys Asp
            565                 570                 575

Gly Lys Val Arg Gln Tyr Gly Ser Ala Val His Asp Glu Lys Leu
            580                 585                 590

Glu Arg Leu Gly Gly Gly Met Ser Asp Thr Arg Trp Leu Arg Thr Gln
    595                 600                 605

His Gly Thr Gly Glu Val Tyr Arg Thr Asp Leu Phe Ala Lys Met Leu
610                 615                 620

Ser Leu Ala Leu Ile Lys Met Thr Thr Leu Asp Pro Tyr Gly Met Gly
625                 630                 635                 640

Ile Glu Met Glu Gly Asp Lys Pro Gly Trp Asn Asp Ala Met Asn Gly
            645                 650                 655

Leu Pro Gly Leu Phe Gly Ser Gly Met Gly Glu Thr Tyr Glu Leu Lys
            660                 665                 670

Arg Leu Val Leu Phe Ile Leu Glu Ala Leu Ser Gly Met Pro Gly Gly
            675                 680                 685

Ala Val Val Ser Gly Asp Pro Gly Asp Ser Gly Leu Ala Gly Arg Lys
            690                 695                 700

Val Arg Leu Pro Leu Glu Met Ala Glu Leu Leu Ser Glu Thr Asp Ser
705                 710                 715                 720

Val Leu Ser Arg Arg Glu Ser Gly Asp Ile Ser Asp Leu Glu Cys Trp
            725                 730                 735

Asp Leu Leu Ala Thr Ala Arg Glu Arg Tyr Arg Glu Ser Ile Arg Phe
            740                 745                 750

Gly Leu Ser Gly Asp Glu Gln Glu Ile Val Phe Ala Ala Leu Glu Pro
            755                 760                 765

Val Phe Lys Arg Phe Leu Gly Arg Leu Asn Glu Gly Ile Ala Lys Ala
            770                 775                 780

Val Lys Leu Gly Gly Gly Leu Val Pro Thr Tyr Phe Arg Phe Glu Ala
785                 790                 795                 800
```

```
Glu Asp Tyr Glu Pro Leu Lys Gly Gly Asp Gly Gly Pro Val Ile Ser
            805                 810                 815

Ser Tyr Gly Leu Pro Val Val Ser Val Ser Arg Phe Arg Ala Glu Ala
        820                 825                 830

Leu Pro Ala Phe Leu Glu Gly Pro Val His Gly Leu Lys Leu Ala Glu
    835                 840                 845

Ser Lys Glu Glu Ala Gln Gly Ile Tyr Arg Ala Val Arg Ser Ser Gly
850                 855                 860

Leu Tyr Asp Glu Lys Leu Gly Met Tyr Lys Thr Ser Val Ser Leu Glu
865                 870                 875                 880

Gln Gln Pro Gln Glu Ile Gly Arg Ile Arg Ala Phe Thr Pro Gly Trp
            885                 890                 895

Leu Glu Arg Glu Ser Ile Phe Leu His Met Ser Tyr Lys Tyr Val Leu
            900                 905                 910

Glu Leu Leu Lys Thr Gly Leu Thr Gly Thr Phe Tyr Glu Glu Phe Lys
        915                 920                 925

Arg Ala Leu Ile Pro Phe Gln Asp Pro Ala Val Tyr Gly Arg Ser Thr
930                 935                 940

Leu Glu Asn Ser Ser Phe Leu Ala Ser Ser Val Asn Pro Asp Pro Gly
945                 950                 955                 960

Val His Gly Arg Gly Phe Val Ala Arg Leu Ser Gly Ser Thr Ala Glu
            965                 970                 975

Phe Leu Ser Met Trp Ser Leu Met Met Ala Gly Ser Arg Pro Phe Arg
                980                 985                 990

Leu Ser Gly Asp Gly Asp Leu Val  Leu Glu Leu Ala Pro  Ala Leu Pro
        995                 1000                 1005

Gly Trp  Leu Phe Lys Asp Asp  Gly Arg Leu Ser Phe  Arg Phe Leu
    1010                 1015                 1020

Gly Ser  Val Arg Val Thr Tyr  Leu Asn Glu Arg Arg  Ala Asp Thr
    1025                 1030                 1035

Phe Gly  Glu Asn Cys Ala Ala  Ile Arg Arg Ile Ser  Val Lys Asp
    1040                 1045                 1050

Gly Ala  Gly Asn Thr Leu Thr  Val Glu Gly Ser Val  Leu Ser Gly
    1055                 1060                 1065

Lys Leu  Ala Glu Asp Ile Arg  Ala Gly Arg Tyr Thr  Glu Leu Glu
    1070                 1075                 1080

Val Val  Leu Glu
    1085

<210> SEQ ID NO 3
<211> LENGTH: 3234
<212> TYPE: DNA
<213> ORGANISM: Gorillibacterium massiliense G5

<400> SEQUENCE: 3
atggcgaact attctttcga gcagaacacg tttgtaatcg agaactatca tgaagcgaaa      60
cccttTgcca gcttttTacc gggtctagcc ggactgaagg gtattccaat gtggacgttt     120 tacgtaaaacc gggggcaggc gatcagcggt ttcggcatca aggataaaaa cagcccgatc    180
atggagtttt cgccggccag catcgcctac aagacggtgt cagccagcgg gtttcgtacc    240
ttcatcaaga ttggtggaga gctgtatgag ccgttccaaa cctttcgtcc cgatcccgat    300
atccatcgcg tcatgcgtgt gaaggctaac gagatttcct tgacgaaaac ccatagccgc    360
catgggctga aggttaacgt cgtttatttt catgtgcccg gcgaggattt tgcggcgctg    420
```

-continued

| | | |
|---|---|---|
| gtgcggcatg tggagattga aagccttggt gacggccagc gggagatcga gctgttggac | 480 | |
| ggcttgccgg aaattttgcc ctacggcgta ggaaacgggg agttcaagga gatcggccat | 540 | |
| ctgcttcgca gctggatgga agtggagaat tgccgaacc gcatcccctt ctataaaaac | 600 | |
| cgttccagca cccacgacga ggcagaagtg agcgaagtgg tcagcggcca tttctacttg | 660 | |
| agcttctccg atgaggaaga tctgctgcgt cccattgtcg atcccgacct cgttttcggc | 720 | |
| gaaaacagtt cgttgtctta tcctgacgtt ttcgcggctg ttcctttggc ggagctgagc | 780 | |
| gagcgcattc cttacgccta caataaaatt ccatgcggct tcagcggcaa aagcgcaaag | 840 | |
| ctcgccccag ggggtaagct gaatctctac acgttgatcg gcaacgtatc tcgggtcgag | 900 | |
| cggatcaatg ccaaggccgc gagtgtttgc tccgctgcct atatcgcgga gaaacgggag | 960 | |
| gaagcgaacc ggttagtgga cgaactgacg gcggacatca gcacccgcac cggggtgccg | 1020 | |
| gtgattgacg cctacgcccg ccaatgctac ctggacaact ttttgcgggg tgggtatcca | 1080 | |
| tttattttcg gcggcgacgg caacaacggt tcaggcacta catcgaaggt cgttcatctt | 1140 | |
| ttctcccgca agcacggcga cctggagcgg gattataact tttttctcgct gctgccggag | 1200 | |
| ttttattccc aaggtaacgg caatttccgc gacgccaacc aaaaccggcg caacgatgtc | 1260 | |
| tttttccagc cgaaggtggg caccttcaac atccgcatgt tcttcagcct gatgcaggcg | 1320 | |
| gacggctata cccgttgggg cgtcgagggt accactttca cggttcctgc ggcaaaagcg | 1380 | |
| gctgaactgg acgctcatct cgcggcatcg gtcaaaaacg gtcaggccga tctgacggct | 1440 | |
| ctggcgcgta aagccttcac accgggcaag gtgatcaacc tgatcgctga ccggaacatc | 1500 | |
| gagctgctcc agccggaagc ggatttcctg aacggtctgt tggggctggc ggagcaaaat | 1560 | |
| atcgaagccc gcttcaacga gggctactgg tccgaccact ggacctataa catggacctg | 1620 | |
| gtggatgcgt atctgtccgt gttcccggac aagaaaaacg agctgttgtt cggcgacgaa | 1680 | |
| acctatgcct actttgacag cccggtgcgg gtattgcctc gcagtgaaaa atatgtggtg | 1740 | |
| aaagacggag ccgtacgtca atatggctcg gttgtccacg atgaagagaa gatgcagacc | 1800 | |
| ctcggcattg ctctgaacgg tacccattgg ttgaagacac agcaaggccg cggagagatt | 1860 | |
| tatcggacta atctgctggt gaaaatcctt tccctgtccc tgagcaaatt cgccaccctc | 1920 | |
| gacccgtacg gcatgggcat cgaaatggaa ggcaacaagc cgggctggaa cgatgccatg | 1980 | |
| aacggactgc ccggcctcat cggctccggc atgagcgaaa cctttgagct gaagcggatg | 2040 | |
| cttcagttcc tcgcaaccgc atgtgcggaa gcatccgacc gcgaagtgcg ggtgccggag | 2100 | |
| gaaatctacc gcttcctgca aaagacggcg aacctggcgg agcagcgtga aagggcgag | 2160 | |
| ctcgacgcct tcccttattg ggatggagta gcggcggcgc gggaagatta ccgggatgaa | 2220 | |
| atccgcttcg gcatcacagg ggcggaaaca gccgtctcct tgaaggatct gcatgcgatc | 2280 | |
| agccgaactt ttttgcaagt ggtggatctc ggcatcgagc gcgcggtaga aatgggcggc | 2340 | |
| ggcatcgtgc ccacttactt ccgatttgaa gcggaagagt tcgaaacgat gctggacgca | 2400 | |
| tcggggaagc cggcgatgag ccactacgga ctgcccaagg caatcgtgcg caagtttcaa | 2460 | |
| ggcatcgcgc tgccacactt cttggaaggg ccggctcgct ggctaaaaac ggtggataac | 2520 | |
| gccgaagagg cacgcgatat ctataaccgc atcaaggcga cggacttgta tgatcccaaa | 2580 | |
| ctgaagatgt acaaaacatc cgtcagcctg gaaaatgaat ctctcgaaat tggccgcatc | 2640 | |
| cgtgcccttta ctccgggatg gctggagcgg gaatccgtat tcatgcatat gtcttacaag | 2700 | |
| tacgtgctga agctgctgaa aaatggtctc tacgaggagt acgaggagga aatgcagcat | 2760 | |
| tccctcgtgc cgttcttgga cccggcgatt tacgccgca gcacgttgga gaactcctcc | 2820 | |

-continued

```
ttcatcgcta cctcggtgaa tcccgatccg caaacgctgg gacgtggttt ttatgcgcgg    2880
ctgagcggct ctacggcgga attcctcagt atgtgggtgg gcatgatggc gggaacgccc    2940
ttccacgtaa cggaagatgg acgtttggcg ttagagttca agccggtact acccggctgg    3000
ctgttcgatg ctgaaggccg aattgccttc cgcttcctcg gcaaaacgga ggtcagctac    3060
cgcaacccgc gcaaagcctc cacatacgga gaaaacgccg cgcgcatcgc atccctgaag    3120
ctgaccgccg aagatggcga acaacataca gtaaacggtt ctgttgtata cggcgaatgg    3180
gcggagaaag tacgcaatgg cgagattgcc gccatcgaaa tcgaactgcg ataa          3234
```

<210> SEQ ID NO 4
<211> LENGTH: 1077
<212> TYPE: PRT
<213> ORGANISM: Gorillibacterium massiliense G5

<400> SEQUENCE: 4

```
Met Ala Asn Tyr Ser Phe Glu Gln Asn Thr Phe Val Ile Glu Asn Tyr
1               5                   10                  15

His Glu Ala Lys Pro Phe Ala Ser Phe Leu Pro Gly Leu Ala Gly Leu
            20                  25                  30

Lys Gly Ile Pro Met Trp Thr Phe Tyr Val Asn Arg Gly Gln Ala Ile
        35                  40                  45

Ser Gly Phe Gly Ile Lys Asp Lys Asn Ser Pro Ile Met Glu Phe Ser
    50                  55                  60

Pro Ala Ser Ile Ala Tyr Lys Thr Val Ser Ala Ser Gly Phe Arg Thr
65                  70                  75                  80

Phe Ile Lys Ile Gly Gly Glu Leu Tyr Glu Pro Phe Gln Thr Phe Arg
                85                  90                  95

Pro Asp Pro Asp Ile His Arg Val Met Arg Val Lys Ala Asn Glu Ile
            100                 105                 110

Ser Leu Thr Glu Thr His Ser Arg His Gly Leu Lys Val Asn Val Val
        115                 120                 125

Tyr Phe His Val Pro Gly Glu Asp Phe Ala Ala Leu Val Arg His Val
    130                 135                 140

Glu Ile Glu Ser Leu Gly Asp Gly Gln Arg Glu Ile Glu Leu Leu Asp
145                 150                 155                 160

Gly Leu Pro Glu Ile Leu Pro Tyr Gly Val Gly Asn Gly Glu Phe Lys
                165                 170                 175

Glu Ile Gly His Leu Leu Arg Ser Trp Met Glu Val Glu Asn Leu Pro
            180                 185                 190

Asn Arg Ile Pro Phe Tyr Lys Asn Arg Ser Ser Thr His Asp Glu Ala
        195                 200                 205

Glu Val Ser Glu Val Val Ser Gly His Phe Tyr Leu Ser Phe Ser Asp
    210                 215                 220

Glu Glu Asp Leu Leu Arg Pro Ile Val Asp Pro Asp Leu Val Phe Gly
225                 230                 235                 240

Glu Asn Ser Ser Leu Ser Tyr Pro Asp Val Phe Ala Ala Val Pro Leu
                245                 250                 255

Ala Glu Leu Ser Glu Arg Ile Pro Tyr Ala Tyr Asn Lys Ile Pro Cys
            260                 265                 270

Gly Phe Ser Gly Lys Ser Ala Lys Leu Ala Pro Gly Gly Lys Leu Asn
        275                 280                 285

Leu Tyr Thr Leu Ile Gly Asn Val Ser Arg Val Glu Arg Ile Asn Ala
    290                 295                 300
```

-continued

```
Lys Ala Ala Ser Val Cys Ser Ala Ala Tyr Ile Ala Glu Lys Arg Glu
305                 310                 315                 320

Glu Ala Asn Arg Leu Val Asp Glu Leu Thr Ala Asp Ile Ser Thr Arg
            325                 330                 335

Thr Gly Val Pro Val Ile Asp Ala Tyr Ala Arg Gln Cys Tyr Leu Asp
                340                 345                 350

Asn Phe Leu Arg Gly Gly Tyr Pro Phe Ile Phe Gly Gly Asp Gly Asn
            355                 360                 365

Asn Gly Ser Gly Thr Thr Ser Lys Val Val His Leu Phe Ser Arg Lys
370                 375                 380

His Gly Asp Leu Glu Arg Asp Tyr Asn Phe Phe Ser Leu Leu Pro Glu
385                 390                 395                 400

Phe Tyr Ser Gln Gly Asn Gly Asn Phe Arg Asp Ala Asn Gln Asn Arg
                405                 410                 415

Arg Asn Asp Val Phe Phe Gln Pro Lys Val Gly Thr Phe Asn Ile Arg
                420                 425                 430

Met Phe Phe Ser Leu Met Gln Ala Asp Gly Tyr Asn Pro Leu Gly Val
            435                 440                 445

Glu Gly Thr Thr Phe Thr Val Pro Ala Ala Lys Ala Ala Glu Leu Asp
450                 455                 460

Ala His Leu Ala Ala Ser Val Lys Asn Gly Gln Ala Asp Leu Thr Ala
465                 470                 475                 480

Leu Ala Arg Lys Ala Phe Thr Pro Gly Lys Val Ile Asn Leu Ile Ala
                485                 490                 495

Asp Arg Asn Ile Glu Leu Leu Gln Pro Glu Ala Asp Phe Leu Asn Gly
            500                 505                 510

Leu Leu Gly Leu Ala Glu Gln Asn Ile Glu Ala Arg Phe Asn Glu Gly
            515                 520                 525

Tyr Trp Ser Asp His Trp Thr Tyr Asn Met Asp Leu Val Asp Ala Tyr
            530                 535                 540

Leu Ser Val Phe Pro Asp Lys Lys Asn Glu Leu Leu Phe Gly Asp Glu
545                 550                 555                 560

Thr Tyr Ala Tyr Phe Asp Ser Pro Val Arg Val Leu Pro Arg Ser Glu
                565                 570                 575

Lys Tyr Val Val Lys Asp Gly Ala Val Arg Gln Tyr Gly Ser Val Val
            580                 585                 590

His Asp Glu Glu Lys Met Gln Thr Leu Gly Ile Ala Leu Asn Gly Thr
            595                 600                 605

His Trp Leu Lys Thr Gln Gln Gly Arg Gly Glu Ile Tyr Arg Thr Asn
610                 615                 620

Leu Leu Val Lys Ile Leu Ser Leu Ser Leu Ser Lys Phe Ala Thr Leu
625                 630                 635                 640

Asp Pro Tyr Gly Met Gly Ile Glu Met Glu Gly Asn Lys Pro Gly Trp
            645                 650                 655

Asn Asp Ala Met Asn Gly Leu Pro Gly Leu Ile Gly Ser Gly Met Ser
            660                 665                 670

Glu Thr Phe Glu Leu Lys Arg Met Leu Gln Phe Leu Ala Thr Ala Cys
            675                 680                 685

Ala Glu Ala Ser Asp Arg Glu Val Arg Val Pro Glu Glu Ile Tyr Arg
            690                 695                 700

Phe Leu Gln Lys Thr Ala Asn Leu Ala Glu Gln Arg Glu Lys Gly Glu
705                 710                 715                 720
```

-continued

```
Leu Asp Ala Phe Pro Tyr Trp Asp Gly Val Ala Ala Arg Glu Asp
            725                 730                 735

Tyr Arg Asp Glu Ile Arg Phe Gly Ile Thr Gly Ala Glu Thr Ala Val
        740                 745                 750

Ser Leu Lys Asp Leu His Ala Ile Ser Arg Thr Phe Leu Gln Val Val
        755                 760                 765

Asp Leu Gly Ile Glu Arg Ala Val Glu Met Gly Gly Ile Val Pro
        770                 775             780

Thr Tyr Phe Arg Phe Glu Ala Glu Glu Phe Glu Thr Met Leu Asp Ala
785                 790                 795                 800

Ser Gly Lys Pro Ala Met Ser His Tyr Gly Leu Pro Lys Ala Ile Val
                805                 810                 815

Arg Lys Phe Gln Gly Ile Ala Leu Pro His Phe Leu Glu Gly Pro Ala
                820                 825                 830

Arg Trp Leu Lys Thr Val Asp Asn Ala Glu Glu Ala Arg Asp Ile Tyr
                835                 840                 845

Asn Arg Ile Lys Ala Thr Asp Leu Tyr Asp Pro Lys Leu Lys Met Tyr
850                 855                 860

Lys Thr Ser Val Ser Leu Glu Asn Glu Ser Leu Glu Ile Gly Arg Ile
865                 870                 875                 880

Arg Ala Phe Thr Pro Gly Trp Leu Glu Arg Glu Ser Val Phe Met His
                885                 890                 895

Met Ser Tyr Lys Tyr Val Leu Glu Leu Leu Lys Asn Gly Leu Tyr Glu
                900                 905                 910

Glu Tyr Glu Glu Glu Met Gln His Ser Leu Val Pro Phe Leu Asp Pro
                915                 920                 925

Ala Ile Tyr Gly Arg Ser Thr Leu Glu Asn Ser Ser Phe Ile Ala Thr
        930                 935                 940

Ser Val Asn Pro Asp Pro Gln Thr Leu Gly Arg Gly Phe Tyr Ala Arg
945                 950                 955                 960

Leu Ser Gly Ser Thr Ala Glu Phe Leu Ser Met Trp Val Gly Met Met
                965                 970                 975

Ala Gly Thr Pro Phe His Val Thr Glu Asp Gly Arg Leu Ala Leu Glu
                980                 985                 990

Phe Lys Pro Val Leu Pro Gly Trp Leu Phe Asp Ala Glu Gly Arg Ile
                995                 1000                1005

Ala Phe Arg Phe Leu Gly Lys Thr Glu Val Ser Tyr Arg Asn Pro
        1010                1015                1020

Arg Lys Ala Ser Thr Tyr Gly Glu Asn Ala Ala Arg Ile Ala Ser
        1025                1030                1035

Leu Lys Leu Thr Ala Glu Asp Gly Glu Gln His Thr Val Asn Gly
        1040                1045                1050

Ser Val Val Tyr Gly Glu Trp Ala Glu Lys Val Arg Asn Gly Glu
        1055                1060                1065

Ile Ala Ala Ile Glu Ile Glu Leu Arg
        1070                1075

<210> SEQ ID NO 5
<211> LENGTH: 3228
<212> TYPE: DNA
<213> ORGANISM: Paenibacillus sp. FSL H8-237
```

<400> SEQUENCE: 5

```
gtgagtaatt attatttcga atcaggtaat tttgtaatgg agcagtttga tacaggaaag     60
cctttctcta gtttcctgcc aggtcttgca ggtcttaagg gaattccaat gtggactttt    120
tatgtgaacc gggggcaagc gatttgcagc tttggagtac gcgacaagaa ctcgccaatc    180
atggaatttt ctccagcaaa tatctcttat aaagacgtag gaaccaccgg cttccgaacc    240
tttattaaaa taaaggcgca gcaagagatt tatgagccat ttcaatcggc acgtccagat    300
cctgccgcca agcggatcat gaccattttg cctaacggac tgacccttga agaaagccat    360
gccgggcatg ggctgaagac gaccgtacac tatttcaatc tgcctaatga cgattatgcc    420
gcgttggtac gtcgggtgga gattgagaat atcggggggca aagagattga actggagctg    480
atggatggtc tgcctgagat cttgccttac ggagtagaaa acagcggcta aaggagatt     540
ggtaacctgc tgcgcagctg gatggacgta tacaatctgg agaacggtat tccgttctat    600
aagctgcgtt ccagcaccaa cgatagcgcg caggttagcg aaatcacaaa tgggcatttc    660
tatctgtcgt ttactggaga aggagaaaaa gtcgcgccaa tcgttgattt cgagcttatt    720
ttcggcggca atacctctct tacttaccca gaccgctttg cgggattaac gctttcggag    780
ctgagtgagc ttccacaata tccagtcaat aaggttcctt gcggcttcag tggtgtggct    840
agacgtttgg cacccggcag cagcttgacc ctgaatactt tggttgggca tgtaaatgac    900
atcgataaaa tcaataaaaa ggcagagcat ttatgccgag atgaatatat tctgtccaaa    960
tcccaagaag ccgcaggtct gacagaggaa ttaacagaag acattgccac gcacacttca   1020
tcggctgtgt tgatgcttta tgccgtcag tcctatctcg ataacttcct gcgtggaggc    1080
tatccttta tttttgacaa tggcggagat ggctttgtgg ttcatttata ttcccgtaaa    1140
catggcgatt tggagcgcga ctataacttc ttctcgcttg ccccagaata ctattcacag   1200
gggaacggaa acttccgcga tatgaatcag aaccgccgga tgatgtgtt ttttaatccg     1260
aaggtgggca gcttcaacat caaaatgttc tatagcttaa ttcaagcaga tggctacaac   1320
ccacttagtg ttcaaggaac aaccctttgaa gtgaagtcag acagcagagc gaaggctgcg   1380
gaatggatcg gagaagcggc tgcggatcat caagctgagc ttgttaagct atgcaacagt   1440
cggttcaccc caggcagcct gatcaattac attgcggatc ataacgttac gttgaaggtt    1500
agtgagcagg agtttctgtc gggtctgcta gccctgtcac agcaaaacat tgaggctgct   1560
tttggcgaag gcttctggtc tgatcactgg acgtataatt tggatctcgt agtaggttat   1620
ttggacatct tccctgacaa gaagcaggag ctttttatttg gggataacac ttatgcgttc   1680
tatgacagcc cagcatatgt gctgccacgt agtgagaagt atgtaattag tgatggaaaa   1740
gcccggcaat atggcgccct cctggaggat gaggagaagc tgcataagct gaaatggaaa    1800
gcaggagata cccattggct gcgtgctgaa ggtgggcaag gtgctattta ccacaccaat    1860
ctgttcgtga agatgttgtc tcttgctttg aataaatttg ctacgcttga ccccttacggc   1920
atgggtgtgg agatggaagg caacaagccg ggctggaacg atgccatgaa cggtctgcca    1980
ggattgtttg gctccggaat gagtgagact tttgagctga gcgtactgt agtctttttg     2040
ctggatgtgc tgaacggtgc tgagaatgta caggagctg taaagctgcc agaagaaatc    2100
gcggagctgc ttgaagcggt atatcacgcg gtaactgctg tcctagcagg agatgtggaa   2160
caattcaact attgggatac agtagcttca gcccgtgaag cttatagagc aagtatccgg    2220
tttggcatta ctggtgttga gtccgcagta acgctggagc acatccgcga agccctttcc   2280
aagttcctag ttaaaattga tgaggggatc aacaaggcgg tagaaatggg caatggactt   2340
```

```
acccccacct atttccgttt tgaagcggag aaattccatc aggtaacaga tgctgagggt    2400
cagccagtca ttagcggata cggactgcca aaagctgtgg tagaggagtt taaggcttat    2460
gccttgcctt atttcctgga aggacctacc cgctggttga agacgatgaa gaacccggtg    2520
caggcaaaag aaatctataa tctgattaag caaacagagc tgtatgatcg ggcaacatct    2580
atgtatcaga cctctgttag tctagaaggc gaatcgcatg aaatcggacg aatgagagcc    2640
ttcacaccag gctggctaga acgggagtct aacttcctac acatgtccta taagtatctg    2700
cttgagctgc tgaagggcgg gctgtacgag gaattctacg gtgagctgaa gacgtcgctg    2760
gtgccattcc ttgatcctgc tgtttatgga cgcagtacac tggaaaattc atcttttatc    2820
gcaactggag gcaatcctga tccaaataac cacggtagag ggttcgtagc gagacttagt    2880
ggatcgactg cggaattctt aagcatgtgg agaacaatga tggctggaag ccatgttttc    2940
agattggagg atggagcgct tacgctgtct ctcgatccgg tattgccagg atggctgttt    3000
gatgaagagg gcaatctgtc cttcactttc cttgggaata cggaggtaat ctattctaac    3060
ccaaaacgtg aaaatacctt tggcgagaag aaggttagca ttcaatcttt gatgcttgta    3120
taccgtaatg gaactatgac taaaatatct ggagcgttcg tgcgcggtga agaggcagag    3180
gctctgcggc gtggagaaat cgcgcaaatt caagcagtat tagcataa                3228
```

<210> SEQ ID NO 6
<211> LENGTH: 1075
<212> TYPE: PRT
<213> ORGANISM: Paenibacillus sp. FSL H8-237

<400> SEQUENCE: 6

```
Met Ser Asn Tyr Tyr Phe Glu Ser Gly Asn Phe Val Met Glu Gln Phe
1               5                   10                  15

Asp Thr Gly Lys Pro Phe Ser Ser Phe Leu Pro Gly Leu Ala Gly Leu
            20                  25                  30

Lys Gly Ile Pro Met Trp Thr Phe Tyr Val Asn Arg Gly Gln Ala Ile
        35                  40                  45

Cys Ser Phe Gly Val Arg Asp Lys Asn Ser Pro Ile Met Glu Phe Ser
    50                  55                  60

Pro Ala Asn Ile Ser Tyr Lys Asp Val Gly Thr Thr Gly Phe Arg Thr
65                  70                  75                  80

Phe Ile Lys Ile Lys Gly Glu Gln Glu Ile Tyr Glu Pro Phe Gln Ser
                85                  90                  95

Ala Arg Pro Asp Pro Ala Ala Lys Arg Ile Met Thr Ile Leu Pro Asn
            100                 105                 110

Gly Leu Thr Leu Glu Glu Ser His Ala Gly His Gly Leu Lys Thr Thr
        115                 120                 125

Val His Tyr Phe Asn Leu Pro Asn Asp Asp Tyr Ala Ala Leu Val Arg
    130                 135                 140

Arg Val Glu Ile Glu Asn Ile Gly Gly Lys Glu Ile Glu Leu Glu Leu
145                 150                 155                 160

Met Asp Gly Leu Pro Glu Ile Leu Pro Tyr Gly Val Glu Asn Ser Gly
                165                 170                 175

Tyr Lys Glu Ile Gly Asn Leu Leu Arg Ser Trp Met Asp Val Tyr Asn
            180                 185                 190

Leu Glu Asn Gly Ile Pro Phe Tyr Lys Leu Arg Ser Ser Thr Asn Asp
        195                 200                 205

Ser Ala Gln Val Ser Glu Ile Thr Asn Gly His Phe Tyr Leu Ser Phe
    210                 215                 220
```

-continued

Thr Gly Glu Gly Glu Lys Val Ala Pro Ile Val Asp Phe Glu Leu Ile
225                 230                 235                 240

Phe Gly Gly Asn Thr Ser Leu Thr Tyr Pro Asp Arg Phe Ala Gly Leu
            245                 250                 255

Thr Leu Ser Glu Leu Ser Glu Leu Pro Gln Tyr Pro Val Asn Lys Val
            260                 265                 270

Pro Cys Gly Phe Ser Gly Val Ala Arg Arg Leu Ala Pro Gly Ser Ser
        275                 280                 285

Leu Thr Leu Asn Thr Leu Val Gly His Val Asn Asp Ile Asp Lys Ile
    290                 295                 300

Asn Lys Lys Ala Glu His Leu Cys Arg Asp Glu Tyr Ile Leu Ser Lys
305                 310                 315                 320

Ser Gln Glu Ala Ala Gly Leu Thr Glu Glu Leu Thr Glu Asp Ile Ala
                325                 330                 335

Thr His Thr Ser Ser Ala Val Phe Asp Ala Tyr Cys Arg Gln Ser Tyr
            340                 345                 350

Leu Asp Asn Phe Leu Arg Gly Gly Tyr Pro Phe Ile Phe Asp Asn Gly
            355                 360                 365

Gly Asp Gly Phe Val Val His Leu Tyr Ser Arg Lys His Gly Asp Leu
370                 375                 380

Glu Arg Asp Tyr Asn Phe Phe Ser Leu Ala Pro Glu Tyr Tyr Ser Gln
385                 390                 395                 400

Gly Asn Gly Asn Phe Arg Asp Met Asn Gln Asn Arg Arg Asn Asp Val
                405                 410                 415

Phe Phe Asn Pro Lys Val Gly Ser Phe Asn Ile Lys Met Phe Tyr Ser
            420                 425                 430

Leu Ile Gln Ala Asp Gly Tyr Asn Pro Leu Ser Val Gln Gly Thr Thr
            435                 440                 445

Phe Glu Val Lys Ser Asp Ser Arg Ala Lys Ala Ala Glu Trp Ile Gly
450                 455                 460

Glu Ala Ala Asp His Gln Ala Glu Leu Val Lys Leu Cys Asn Ser
465                 470                 475                 480

Arg Phe Thr Pro Gly Ser Leu Ile Asn Tyr Ile Ala Asp His Asn Val
            485                 490                 495

Thr Leu Lys Val Ser Glu Gln Glu Phe Leu Ser Gly Leu Leu Ala Leu
            500                 505                 510

Ser Gln Gln Asn Ile Glu Ala Ala Phe Gly Glu Gly Phe Trp Ser Asp
            515                 520                 525

His Trp Thr Tyr Asn Leu Asp Leu Val Val Gly Tyr Leu Asp Ile Phe
    530                 535                 540

Pro Asp Lys Lys Gln Glu Leu Leu Phe Gly Asp Asn Thr Tyr Ala Phe
545                 550                 555                 560

Tyr Asp Ser Pro Ala Tyr Val Leu Pro Arg Ser Glu Lys Tyr Val Ile
            565                 570                 575

Ser Asp Gly Lys Ala Arg Gln Tyr Gly Ala Leu Leu Glu Asp Glu Glu
            580                 585                 590

Lys Leu His Lys Leu Lys Trp Lys Ala Gly Asp Thr Trp Leu Arg
    595                 600                 605

Ala Glu Gly Gly Gln Gly Ala Ile Tyr His Thr Asn Leu Phe Val Lys
    610                 615                 620

Met Leu Ser Leu Ala Leu Asn Lys Phe Ala Thr Leu Asp Pro Tyr Gly
625                 630                 635                 640

```
Met Gly Val Glu Met Glu Gly Asn Lys Pro Gly Trp Asn Asp Ala Met
            645                 650                 655

Asn Gly Leu Pro Gly Leu Phe Gly Ser Gly Met Ser Glu Thr Phe Glu
        660                 665                 670

Leu Lys Arg Thr Val Val Phe Leu Leu Asp Val Leu Asn Gly Ala Glu
    675                 680                 685

Asn Val Gln Gly Ala Val Lys Leu Pro Glu Glu Ile Ala Glu Leu Leu
690                 695                 700

Glu Ala Val Tyr His Ala Val Thr Ala Val Leu Ala Gly Asp Val Glu
705                 710                 715                 720

Gln Phe Asn Tyr Trp Asp Thr Val Ala Ser Ala Arg Glu Ala Tyr Arg
                725                 730                 735

Ala Ser Ile Arg Phe Gly Ile Thr Gly Val Glu Ser Ala Val Thr Leu
            740                 745                 750

Glu His Ile Arg Glu Ala Leu Ser Lys Phe Leu Val Lys Ile Asp Glu
        755                 760                 765

Gly Ile Asn Lys Ala Val Glu Met Gly Asn Gly Leu Thr Pro Thr Tyr
    770                 775                 780

Phe Arg Phe Glu Ala Glu Lys Phe His Gln Val Thr Asp Ala Glu Gly
785                 790                 795                 800

Gln Pro Val Ile Ser Gly Tyr Gly Leu Pro Lys Ala Val Val Glu Glu
                805                 810                 815

Phe Lys Ala Tyr Ala Leu Pro Tyr Phe Leu Gly Pro Thr Arg Trp
            820                 825                 830

Leu Lys Thr Met Lys Asn Pro Val Gln Ala Lys Glu Ile Tyr Asn Leu
        835                 840                 845

Ile Lys Gln Thr Glu Leu Tyr Asp Arg Ala Thr Ser Met Tyr Gln Thr
    850                 855                 860

Ser Val Ser Leu Glu Gly Glu Ser His Glu Ile Gly Arg Met Arg Ala
865                 870                 875                 880

Phe Thr Pro Gly Trp Leu Glu Arg Glu Ser Asn Phe Leu His Met Ser
                885                 890                 895

Tyr Lys Tyr Leu Leu Glu Leu Leu Lys Gly Gly Leu Tyr Glu Glu Phe
            900                 905                 910

Tyr Gly Glu Leu Lys Thr Ser Leu Val Pro Phe Leu Asp Pro Ala Val
        915                 920                 925

Tyr Gly Arg Ser Thr Leu Glu Asn Ser Ser Phe Ile Ala Thr Gly Gly
    930                 935                 940

Asn Pro Asp Pro Asn Asn His Gly Arg Gly Phe Val Ala Arg Leu Ser
945                 950                 955                 960

Gly Ser Thr Ala Glu Phe Leu Ser Met Trp Arg Thr Met Met Ala Gly
                965                 970                 975

Ser His Val Phe Arg Leu Glu Asp Gly Ala Leu Thr Leu Ser Leu Asp
            980                 985                 990

Pro Val Leu Pro Gly Trp Leu Phe Asp Glu Glu Gly Asn Leu Ser Phe
        995                 1000                1005

Thr Phe Leu Gly Asn Thr Glu Val Ile Tyr Ser Asn Pro Lys Arg
        1010                1015                1020

Glu Asn Thr Phe Gly Glu Lys Lys Val Ser Ile Gln Ser Leu Met
        1025                1030                1035

Leu Val Tyr Arg Asn Gly Thr Met Thr Lys Ile Ser Gly Ala Phe
        1040                1045                1050
```

Val Arg Gly Glu Glu Ala Glu Ala Leu Arg Arg Gly Glu Ile Ala
1055                1060                    1065

Gln Ile Gln Ala Val Leu Ala
    1070            1075

<210> SEQ ID NO 7
<211> LENGTH: 3216
<212> TYPE: DNA
<213> ORGANISM: Caloramator australicus RC3

<400> SEQUENCE: 7

| | | | | | |
|---|---|---|---|---|---|
| atgagtaagt | tttactttga | tgaaaaaaat | agatttgtta | tagaaaattt | taatgcatca | 60 |
| aagcctttg | caagtttctt | acctggaata | gcaggtaaga | agggaattcc | aatgtggata | 120 |
| ttttacgtca | atagaggtca | atgtatatca | tcctttggaa | taaaaaacaa | agataatcca | 180 |
| ataatggagt | ttttcccagc | atataaatgt | tatcaaaatg | ttcaaagcgt | aggatttagg | 240 |
| acatttataa | agtttacaga | tgaacaaaat | atatatgaac | ctttcttata | tccaagaaat | 300 |
| aataaagtta | atcaaaaaat | gtatatagga | atgaatgagc | ttgaaataga | agaagtaaac | 360 |
| acagaaaatg | gattgcaaat | aaatgttctt | tattttatgc | ttccacaaga | aaagatagct | 420 |
| gctctagtta | ggaaagtaac | aattaaaaat | atttcaaaca | acaaaaaaag | tcttgaaatc | 480 |
| ttggacggga | tgccagtagt | gcttccatat | gggataagcg | atggtggatt | aaaacaagtt | 540 |
| ggcaataccc | ttaaagcatg | gatggaagta | tataatcatg | aaggcggaat | cccaattttt | 600 |
| agaatgagat | cgtcatcaga | agatagtgtt | aatgttacag | agtttaaaga | aggtaatttt | 660 |
| tacttgtcat | ttaaaaatgt | aaaaggtaaa | aaggatttaa | taaatccaat | tgttgatatt | 720 |
| gaccttgttt | ttggaatgaa | tacatccctt | agctatccag | atgtatttta | taatttccct | 780 |
| ttaagtgaaa | ttttagatag | aaagcaaatt | acttcaaaca | aaataccatg | tagttttttca | 840 |
| gcagtaagtt | tggatgttaa | tgcaggggaa | gctttggata | tatatactat | tatcggccat | 900 |
| gcaccggaga | tttctgtttt | agaaagctat | aaagaaatat | ttatggatga | aaattatatt | 960 |
| aataataaat | atttagaagg | taaaaaaatt | gtagagagat | aacagatga | tatatataca | 1020 |
| aaacatcat | cgaagctatt | tgatgaatat | tgtagacaaa | gttacctaga | caacattcta | 1080 |
| aggggtggat | atccttaat | attaaaaaat | ggtgacaagc | cacttgttta | ttatatgtat | 1140 |
| tcaagaaaac | atggcgactt | agaaagagat | tataattact | tttcacttga | accagaatat | 1200 |
| tattcaagcg | gaaatggaaa | ttacagagat | ataaatcaaa | atagaagaaa | tgatgttttc | 1260 |
| tttaatccag | aagtaaaaag | ttataacata | aaaattttca | tgaatttaat | tcaatcagat | 1320 |
| ggttataatc | cactagttat | taatgggggtt | aaatatagaa | ttaaagctaa | cagtttagac | 1380 |
| tttatcgacg | aactagctga | agatacgac | aagttaaagg | agattttatc | aaatccatttt | 1440 |
| acaccaggta | ggctgattac | atttatagaa | caaagaaata | taaaacttaa | ggtttcacaa | 1500 |
| gaggaattct | taacaaagat | tatggaaaat | gcggaagaag | aaattgatgc | agttcatggt | 1560 |
| gaaggatttt | ggacggatca | ttggacatat | aacttagact | tgattgagaa | ttatttagag | 1620 |
| gtttatccag | ataaaaagag | ggatttgcta | tttaatgaat | atgattatac | ttattttgat | 1680 |
| aatagtaaag | ttgtccttacc | aagggagaaa | agatatgtat | tgtctaacgg | taaagtaaga | 1740 |
| caatataatt | caatagtaga | agataaggac | aaaagaaac | ttatagaatc | aagaaaaact | 1800 |
| tataaaaata | taatgagagc | taacaaaggc | gtaggagaga | tatatacaac | taattttaатt | 1860 |
| gtgaagctat | taaatcttgc | agcagtaaaa | tttgctacta | ttgatcctgc | tggaatggga | 1920 |
| attgagatgg | aggcaggaaa | accaggatgg | tatgatgcat | aaatggtctt | tcctggactc | 1980 |

```
tttggttctt cagttgcaga ggcctttgaa ttggttagac ttttcaattt tatattagat    2040
gttttaaagg aatatccaga tgaagaaatt aaaattccga ttgaagttat gcagctaatt    2100
gaaaacgaag ttaagtatgt tcaaagatat aacgaatcaa atatggataa taaagattat    2160 gattttggt caattatgtc tgatttacgt gagaaatata gggaagatgt aaaatttggg    2220
tttcaaggca agaagtatc tgtaagatca gcggaattga tagataagat caaagaactt    2280
aaagataaat tacagttggg cttagataaa gctattataa ataacgatgg tttaatgcct    2340
acgtattttt attatgatgt agaagaatac gagatcatta aaggcattga caaagatgta    2400
gacgatgaaa atcaagaaaa gtatattaga gcattaaaat ttaaacaaaa taaaatgcca    2460
ttatttttgg aagggatagt tagagggttt aaaatttaca atgataaaga cttcttaaga    2520
gatgtatata aaagagtaaa aaacagtgac ttatttgata aaaaattaaa gatgtataaa    2580
gttaatgcct ctttaaataa ggaaactata gaaataggca gggcaagagc atttactcct    2640
ggatggctag aaaatgaatc aatttggctt catatggaat ataaatatat gcttgagcta    2700
ttaaaaagtg gtctttataa ggaatactat gatgacttta aaaacgtatt gatacccttc    2760
atggatgcaa gtgtatatgg cagaagccca cttgaaaatt catcctttat cgcaagtagt    2820
gctaatgtcg acgagtcaat tcatggaacg ggatttgttg caagattaag tggtgcaact    2880
gcagaatttt tgagtatgtg gaggttaatg tttgtaggta aaaaaccatt taaaattata    2940
aacggcaaac tcactttgag ctttaatcct gtgttaccag aatggttatt cgatgaagag    3000
aataaagtta gctttaattt tttaggcaga tgcagggtaa catattataa tccatctaga    3060
aaaaatactt atgaaatgga cattactaag caaaaaataa taatctatt acctagtgga    3120 aatactattg aatttttaga taatttttata gaagaagaat atgcaacatt gattagagaa    3180
ggaaaaataa acagaataga tatttactta aaataa                              3216
```

<210> SEQ ID NO 8
<211> LENGTH: 1071
<212> TYPE: PRT
<213> ORGANISM: Caloramator australicus RC3

<400> SEQUENCE: 8

Met Ser Lys Phe Tyr Phe Asp Glu Lys Asn Arg Phe Val Ile Glu Asn
1               5                   10                  15

Phe Asn Ala Ser Lys Pro Phe Ala Ser Phe Leu Pro Gly Ile Ala Gly
                20                  25                  30

Lys Lys Gly Ile Pro Met Trp Ile Phe Tyr Val Asn Arg Gly Gln Cys
            35                  40                  45

Ile Ser Ser Phe Gly Ile Lys Asn Lys Asp Asn Pro Ile Met Glu Phe
        50                  55                  60

Phe Pro Ala Tyr Lys Cys Tyr Gln Asn Val Gln Ser Val Gly Phe Arg
65                  70                  75                  80

Thr Phe Ile Lys Phe Thr Asp Glu Gln Asn Ile Tyr Glu Pro Phe Leu
                85                  90                  95

Tyr Pro Arg Asn Asn Lys Val Asn Gln Lys Met Tyr Ile Gly Met Asn
            100                 105                 110

Glu Leu Glu Ile Glu Glu Val Asn Thr Glu Asn Gly Leu Gln Ile Asn
        115                 120                 125

Val Leu Tyr Phe Met Leu Pro Gln Gly Lys Ile Ala Ala Leu Val Arg
    130                 135                 140

Lys Val Thr Ile Lys Asn Ile Ser Asn Asn Lys Lys Ser Leu Glu Ile
145                 150                 155                 160

-continued

```
Leu Asp Gly Met Pro Val Val Leu Pro Tyr Gly Ile Ser Asp Gly Gly
            165                 170                 175
Leu Lys Gln Val Gly Asn Thr Leu Lys Ala Trp Met Glu Val Tyr Asn
        180                 185                 190
His Glu Gly Gly Ile Pro Ile Phe Arg Met Arg Ser Ser Glu Asp
        195                 200                 205
Ser Val Asn Val Thr Glu Phe Lys Glu Gly Asn Phe Tyr Leu Ser Phe
        210                 215                 220
Lys Asn Val Lys Gly Lys Asp Leu Ile Asn Pro Ile Val Asp Ile
225                 230                 235                 240
Asp Leu Val Phe Gly Met Asn Thr Ser Leu Ser Tyr Pro Asp Val Phe
            245                 250                 255
Tyr Asn Phe Pro Leu Ser Glu Ile Leu Asp Arg Lys Gln Ile Thr Ser
            260                 265                 270
Asn Lys Ile Pro Cys Ser Phe Ser Ala Val Ser Leu Asp Val Asn Ala
        275                 280                 285
Gly Glu Ala Leu Asp Ile Tyr Thr Ile Ile Gly His Ala Pro Glu Ile
        290                 295                 300
Ser Val Leu Glu Ser Tyr Lys Glu Ile Phe Met Asp Glu Asn Tyr Ile
305                 310                 315                 320
Asn Asn Lys Tyr Leu Glu Gly Lys Lys Ile Val Glu Arg Leu Thr Asp
            325                 330                 335
Asp Ile Tyr Thr Lys Thr Ser Ser Lys Leu Phe Asp Glu Tyr Cys Arg
            340                 345                 350
Gln Ser Tyr Leu Asp Asn Ile Leu Arg Gly Gly Tyr Pro Leu Ile Leu
        355                 360                 365
Lys Asn Gly Asp Lys Pro Leu Val Tyr Tyr Met Tyr Ser Arg Lys His
        370                 375                 380
Gly Asp Leu Glu Arg Asp Tyr Asn Tyr Phe Ser Leu Glu Pro Glu Tyr
385                 390                 395                 400
Tyr Ser Ser Gly Asn Gly Asn Tyr Arg Asp Ile Asn Gln Asn Arg Arg
            405                 410                 415
Asn Asp Val Phe Phe Asn Pro Glu Val Lys Ser Tyr Asn Ile Lys Ile
            420                 425                 430
Phe Met Asn Leu Ile Gln Ser Asp Gly Tyr Asn Pro Leu Val Ile Asn
        435                 440                 445
Gly Val Lys Tyr Arg Ile Lys Ala Asn Ser Leu Asp Phe Ile Asp Glu
        450                 455                 460
Leu Ala Glu Asp Thr Asp Lys Leu Lys Glu Ile Leu Ser Asn Pro Phe
465                 470                 475                 480
Thr Pro Gly Arg Leu Ile Thr Phe Ile Glu Gln Arg Asn Ile Lys Leu
            485                 490                 495
Lys Val Ser Gln Glu Glu Phe Leu Thr Lys Ile Met Glu Asn Ala Glu
            500                 505                 510
Glu Glu Ile Asp Ala Val His Gly Glu Gly Phe Trp Thr Asp His Trp
        515                 520                 525
Thr Tyr Asn Leu Asp Leu Ile Glu Asn Tyr Leu Glu Val Tyr Pro Asp
        530                 535                 540
Lys Lys Arg Asp Leu Leu Phe Asn Glu Tyr Asp Tyr Thr Tyr Phe Asp
545                 550                 555                 560
Asn Ser Lys Val Val Leu Pro Arg Glu Lys Arg Tyr Val Leu Ser Asn
            565                 570                 575
```

-continued

Gly Lys Val Arg Gln Tyr Asn Ser Ile Val Glu Asp Lys Asp Lys Lys
                580                 585                 590

Lys Leu Ile Glu Ser Arg Lys Thr Tyr Lys Asn Ile Met Arg Ala Asn
            595                 600                 605

Lys Gly Val Gly Glu Ile Tyr Thr Thr Asn Leu Ile Val Lys Leu Leu
610                 615                 620

Asn Leu Ala Ala Val Lys Phe Ala Thr Ile Asp Pro Ala Gly Met Gly
625                 630                 635                 640

Ile Glu Met Glu Ala Gly Lys Pro Gly Trp Tyr Asp Ala Leu Asn Gly
                645                 650                 655

Leu Pro Gly Leu Phe Gly Ser Ser Val Ala Glu Ala Phe Glu Leu Val
            660                 665                 670

Arg Leu Phe Asn Phe Ile Leu Asp Val Leu Lys Glu Tyr Pro Asp Glu
            675                 680                 685

Glu Ile Lys Ile Pro Ile Glu Val Met Gln Leu Ile Glu Asn Glu Val
690                 695                 700

Lys Tyr Val Gln Arg Tyr Asn Glu Ser Asn Met Asp Asn Lys Asp Tyr
705                 710                 715                 720

Asp Phe Trp Ser Ile Met Ser Asp Leu Arg Glu Lys Tyr Arg Glu Asp
                725                 730                 735

Val Lys Phe Gly Phe Gln Gly Lys Glu Val Ser Val Arg Ser Ala Glu
            740                 745                 750

Leu Ile Asp Lys Ile Lys Glu Leu Lys Asp Lys Leu Gln Leu Gly Leu
            755                 760                 765

Asp Lys Ala Ile Ile Asn Asn Asp Gly Leu Met Pro Thr Tyr Phe Tyr
770                 775                 780

Tyr Asp Val Glu Glu Tyr Glu Ile Ile Lys Gly Ile Asp Lys Asp Val
785                 790                 795                 800

Asp Asp Glu Asn Gln Glu Lys Tyr Ile Arg Ala Leu Lys Phe Lys Gln
                805                 810                 815

Asn Lys Met Pro Leu Phe Leu Glu Gly Ile Val Arg Gly Phe Lys Ile
            820                 825                 830

Tyr Asn Asp Lys Asp Phe Leu Arg Asp Val Tyr Lys Arg Val Lys Asn
            835                 840                 845

Ser Asp Leu Phe Asp Lys Lys Leu Lys Met Tyr Lys Val Asn Ala Ser
850                 855                 860

Leu Asn Lys Glu Thr Ile Glu Ile Gly Arg Ala Arg Ala Phe Thr Pro
865                 870                 875                 880

Gly Trp Leu Glu Asn Glu Ser Ile Trp Leu His Met Glu Tyr Lys Tyr
                885                 890                 895

Met Leu Glu Leu Leu Lys Ser Gly Leu Tyr Lys Glu Tyr Tyr Asp Asp
            900                 905                 910

Phe Lys Asn Val Leu Ile Pro Phe Met Asp Ala Ser Val Tyr Gly Arg
            915                 920                 925

Ser Pro Leu Glu Asn Ser Ser Phe Ile Ala Ser Ser Ala Asn Val Asp
930                 935                 940

Glu Ser Ile His Gly Thr Gly Phe Val Ala Arg Leu Ser Gly Ala Thr
945                 950                 955                 960

Ala Glu Phe Leu Ser Met Trp Arg Leu Met Phe Val Gly Lys Lys Pro
                965                 970                 975

Phe Lys Ile Ile Asn Gly Lys Leu Thr Leu Ser Phe Asn Pro Val Leu
            980                 985                 990

-continued

```
Pro Glu Trp Leu Phe Asp Glu Glu  Asn Lys Val Ser Phe  Asn Phe Leu
        995                 1000                 1005

Gly Arg  Cys Arg Val Thr Tyr  Tyr Asn Pro Ser Arg  Lys Asn Thr
    1010                 1015                 1020

Tyr Glu  Met Asp Ile Thr Lys  Gln Lys Ile Ile Ile  Tyr Leu Pro
    1025                 1030                 1035

Ser Gly  Asn Thr Ile Glu Phe  Leu Asp Asn Phe Ile  Glu Glu Glu
    1040                 1045                 1050

Tyr Ala  Thr Leu Ile Arg Glu  Gly Lys Ile Asn Arg  Ile Asp Ile
    1055                 1060                 1065

Tyr Leu  Lys
    1070

<210> SEQ ID NO 9
<211> LENGTH: 3183
<212> TYPE: DNA
<213> ORGANISM: Clostridium grantii DSM 8605

<400> SEQUENCE: 9
atgtcagtag aatatagttt taacgataaa aatcaattta tgatagaaga ttatgataaa     60
gcaaaaactt ttgcaagttt tttaccaggt attgcaggtg ttgatggtat accaatgtgg    120
tctttttatg taaatagagg gcaaggaatg gggagtttcg gtgttaaaga taaagataat    180
actataatgg aatttttccc tgctaattta atgtataaaa atatagaact acaaggattt    240
agaactttta taaaatacca aggtaaaatt catgaaattt tttcttctat gtcacaagac    300
caagttgaaa gaaaaatggc aattgagaaa aatatattat ccattgaaga agtgaataaa    360
actttaaact tgaaaattaa agtaacatat tttacaatgc ctaaagaaga ttttgctgca    420
attgtaagaa aagtagaaat tgttgatttg aataataatg aagtggaaat tgaagtgttg    480
gatgggttaa cacaaattct gccttacgga gttagtaatt cggcttatca atcaatggcc    540
aatttaagta gagcttggtt tgatgtttat aatctagaaa acaatattcc atactataag    600
gtaagagcaa ctacaagtga ttcttcagaa gtaggagaag taacaaaagg gaatttttac    660
ttagctttcg cttcaaacaa tgaaggcttg ctaccaacta tatttgatgt agatgttata    720
tttggaacaa atacatcttt aacttatcca gcaggatggg attgctcagt agaagaatta    780
aataagcgta ttcaaattcc acaaaacaag gtatcaggag gatttacagc tgttaaagcc    840
tcaataaaag ataaatttac tttatgttca attattggtc atatagcgtc cccagaactt    900
ataaatgcta aaaagcataa tttcactatg gaatacatta aaaataaaga gtttgaagca    960
agaaaattag tggattcttt agtagaggac actaaaacaa aaacatcaaa tgctttattt   1020
gataaatata ttgattcatg ttatttggat aatatcttaa gaggcggata tcctttagct   1080
atagaagcgg gggataaaaa tcatatttat catgtttttt ctagaaaaca tggagataca   1140
gaaagagaat acaatttctt ttctttagaa ccggcttatt attctcaagg aaatggtaat   1200
tttagagatg taaatcagaa tagaagaagt gatatattat ttaaccctaa ggtgaaaaat   1260
tttaatgtaa aacaatttat gagtttaata caagcggatg ggtataatcc tttatccgtt   1320
aaaggctcta cctttacttt tgataattca tatatggatg aagttttaaa ttatttagaa   1380
aaggggaaag agggatttaa gagtatttta gaggagaact ttactcctgg cgatattata   1440
acatatttat gtgagaataa tattgattta agtatatcaa atgatgagta tttaaatctt   1500
atattaagta aatctactca aaattatgaa gcgaactttg gagaaggtta ttggacagat   1560
cattggactt ataacatgga tttagtagat acttatttga atatttatcc agacatgttg   1620
```

-continued

```
gaagactttt tgtttgaaga aatggattat aaatattttg atagtccagt aaaagtttta   1680
aaaagagaag aaaaatatat aattaaaaat ggtaaagttc gtcaatatgg ttctatattt   1740
gaggatgaaa agaaatgcca tgatttaggg atagacataa agggtacaaa ttggttaaaa   1800
acagaaggcg gaaaaggaaa agtatatgaa acaaatcttt atgctaagct tatttctctt   1860
gctttaaata aatttgtaac aatggaccct tatggtatgg gtattgaaat ggaaggggaa   1920
aaacctggtt ggaatgatgc aatgaatgga ttaccaggat tattcggctc tggactaaat   1980
gaaactgctg aacttaaaag aattgttgaa tttatagtag aagtatcttc taaattcaat   2040
aaagatttta tgtttccagt agaaatgaca gaattactga tgcacacaga aaaaacttta   2100
aatagatatt taaatgaaga atttgaagag tttgagtact ggaataaaat agctacctta   2160
agagaagaat atcgtgaaaa aatatactac ggtattgctg gagaagaagt aaaactttct   2220
tcaaaagaaa ttcttcaagc ctttacaaag tttaatcaca aaataaataa aggtcttgag   2280
aaagcgctag agtacggtaa tggtatatat ccaacttact ttacttatga agctaaagaa   2340
tatgagataa tagaaggcaa agtaaatccg gtaaatggat atcaaaatgt aaaagtcaat   2400
gcctttgaat gtaagcctat gcctttattt ttagaaggac ctgctcgtac tttaaaaagt   2460
atgaaggata taaacaaatc cagaactctt tataaagcta taaaagaaag tgatatttat   2520
gataaaaaac ttaagatgta taaaacttct gttccattag atgagttaag taatgaaatt   2580
ggaagagcaa gagcctttac tgctggatgg ttagaaagag aagctgtatt ccttcatatg   2640
gaatataaat atttgttagc tcttttaaaa gccggtttat ataatgaata ttatgaagac   2700
atgcaaacca cattaactgc tttccttgat ccacaagttt acggaagaag tactttagag   2760
aattcatcct ttatagctag ttctgttaac ccagatgatg cggttcatgg tagaggcttt   2820
gttgcaagac ttagtgggtc tacagcggaa atgttaagta tttggtttat aatgatggca   2880
ggggaaaaag tatttactta tgaaaatgat aaattacaat tagaattaag tccaattctt   2940
ccagcatggt tatttgataa tgagggcaaa gtatctttca cattcttggg taaaacagag   3000
gtaacatatc ataatcctaa aaaattaaat acttatggtg aaaataaagc tgtggcagat   3060
aaaattatta taactgtaaa tgaaaatgaa aaaattgaat taaaaggaaa cataattaca   3120
gaagattatg ctaaagctat aagagatgga aagattaata aagtagacat ttatttcaaa   3180
taa                                                                 3183
```

<210> SEQ ID NO 10
<211> LENGTH: 1060
<212> TYPE: PRT
<213> ORGANISM: Clostridium grantii DSM 8605

<400> SEQUENCE: 10

```
Met Ser Val Glu Tyr Ser Phe Asn Asp Lys Asn Gln Phe Met Ile Glu
1               5                   10                  15

Asp Tyr Asp Lys Ala Lys Thr Phe Ala Ser Phe Leu Pro Gly Ile Ala
            20                  25                  30

Gly Val Asp Gly Ile Pro Met Trp Ser Phe Tyr Val Asn Arg Gly Gln
        35                  40                  45

Gly Met Gly Ser Phe Gly Val Lys Asp Lys Asp Asn Thr Ile Met Glu
    50                  55                  60

Phe Phe Pro Ala Asn Leu Met Tyr Lys Asn Ile Glu Leu Gln Gly Phe
65                  70                  75                  80

Arg Thr Phe Ile Lys Tyr Gln Gly Lys Ile His Glu Ile Phe Ser Ser
                85                  90                  95
```

```
Met Ser Gln Asp Gln Val Glu Arg Lys Met Ala Ile Glu Lys Asn Ile
            100                 105                 110
Leu Ser Ile Glu Glu Val Asn Lys Thr Leu Asn Leu Lys Ile Lys Val
        115                 120                 125
Thr Tyr Phe Thr Met Pro Lys Glu Asp Phe Ala Ala Ile Val Arg Lys
    130                 135                 140
Val Glu Ile Val Asp Leu Asn Asn Glu Val Glu Ile Glu Val Leu
145                 150                 155                 160
Asp Gly Leu Thr Gln Ile Leu Pro Tyr Gly Val Ser Asn Ser Ala Tyr
                165                 170                 175
Gln Ser Met Ala Asn Leu Ser Arg Ala Trp Phe Asp Val Tyr Asn Leu
            180                 185                 190
Glu Asn Asn Ile Pro Tyr Tyr Lys Val Arg Ala Thr Thr Ser Asp Ser
        195                 200                 205
Ser Glu Val Gly Glu Val Thr Lys Gly Asn Phe Tyr Leu Ala Phe Ala
    210                 215                 220
Ser Asn Asn Glu Gly Leu Leu Pro Thr Ile Phe Asp Val Asp Val Ile
225                 230                 235                 240
Phe Gly Thr Asn Thr Ser Leu Thr Tyr Pro Ala Gly Trp Asp Cys Ser
                245                 250                 255
Val Glu Glu Leu Asn Lys Arg Ile Gln Ile Pro Gln Asn Lys Val Ser
            260                 265                 270
Gly Gly Phe Thr Ala Val Lys Ala Ser Ile Lys Asp Lys Phe Thr Leu
        275                 280                 285
Cys Ser Ile Ile Gly His Ile Ala Ser Pro Glu Leu Ile Asn Ala Lys
    290                 295                 300
Lys His Asn Phe Thr Met Glu Tyr Ile Lys Asn Lys Glu Phe Glu Ala
305                 310                 315                 320
Arg Lys Leu Val Asp Ser Leu Val Glu Asp Thr Lys Thr Lys Thr Ser
                325                 330                 335
Asn Ala Leu Phe Asp Lys Tyr Ile Asp Ser Cys Tyr Leu Asp Asn Ile
            340                 345                 350
Leu Arg Gly Gly Tyr Pro Leu Ala Ile Glu Ala Gly Asp Lys Asn His
        355                 360                 365
Ile Tyr His Val Phe Ser Arg Lys His Gly Asp Thr Glu Arg Glu Tyr
    370                 375                 380
Asn Phe Phe Ser Leu Glu Pro Ala Tyr Tyr Ser Gln Gly Asn Gly Asn
385                 390                 395                 400
Phe Arg Asp Val Asn Gln Asn Arg Arg Ser Asp Ile Leu Phe Asn Pro
                405                 410                 415
Lys Val Lys Asn Phe Asn Val Lys Gln Phe Met Ser Leu Ile Gln Ala
            420                 425                 430
Asp Gly Tyr Asn Pro Leu Ser Val Lys Gly Ser Thr Phe Thr Phe Asp
        435                 440                 445
Asn Ser Tyr Met Asp Glu Val Leu Asn Tyr Leu Glu Lys Gly Lys Glu
    450                 455                 460
Gly Phe Lys Ser Ile Leu Glu Glu Asn Phe Thr Pro Gly Asp Ile Ile
465                 470                 475                 480
Thr Tyr Leu Cys Glu Asn Asn Ile Asp Leu Ser Ile Ser Asn Asp Glu
                485                 490                 495
Tyr Leu Asn Leu Ile Leu Ser Lys Ser Thr Gln Asn Tyr Glu Ala Asn
            500                 505                 510
```

```
Phe Gly Glu Gly Tyr Trp Thr Asp His Trp Thr Tyr Asn Met Asp Leu
            515                 520                 525

Val Asp Thr Tyr Leu Asn Ile Tyr Pro Asp Met Leu Glu Asp Phe Leu
530                 535                 540

Phe Glu Glu Met Asp Tyr Lys Tyr Phe Asp Ser Pro Val Lys Val Leu
545                 550                 555                 560

Lys Arg Glu Glu Lys Tyr Ile Ile Lys Asn Gly Lys Val Arg Gln Tyr
                565                 570                 575

Gly Ser Ile Phe Glu Asp Glu Lys Lys Cys His Asp Leu Gly Ile Asp
            580                 585                 590

Ile Lys Gly Thr Asn Trp Leu Lys Thr Glu Gly Gly Lys Gly Lys Val
            595                 600                 605

Tyr Glu Thr Asn Leu Tyr Ala Lys Leu Ile Ser Leu Ala Leu Asn Lys
610                 615                 620

Phe Val Thr Met Asp Pro Tyr Gly Met Gly Ile Glu Met Glu Gly Glu
625                 630                 635                 640

Lys Pro Gly Trp Asn Asp Ala Met Asn Gly Leu Pro Gly Leu Phe Gly
                645                 650                 655

Ser Gly Leu Asn Glu Thr Ala Glu Leu Lys Arg Ile Val Glu Phe Ile
            660                 665                 670

Val Glu Val Ser Ser Lys Phe Asn Lys Asp Phe Met Phe Pro Val Glu
            675                 680                 685

Met Thr Glu Leu Leu Met His Thr Glu Lys Thr Leu Asn Arg Tyr Leu
690                 695                 700

Asn Glu Glu Phe Glu Glu Phe Glu Tyr Trp Asn Lys Ile Ala Thr Leu
705                 710                 715                 720

Arg Glu Glu Tyr Arg Glu Lys Ile Tyr Tyr Gly Ile Ala Gly Glu Glu
                725                 730                 735

Val Lys Leu Ser Ser Lys Glu Ile Leu Gln Ala Phe Thr Lys Phe Asn
            740                 745                 750

His Lys Ile Asn Lys Gly Leu Glu Lys Ala Leu Glu Tyr Gly Asn Gly
            755                 760                 765

Ile Tyr Pro Thr Tyr Phe Thr Tyr Glu Ala Lys Glu Tyr Glu Ile Ile
770                 775                 780

Glu Gly Lys Val Asn Pro Val Asn Gly Tyr Gln Asn Val Lys Val Asn
785                 790                 795                 800

Ala Phe Glu Cys Lys Pro Met Pro Leu Phe Leu Glu Gly Pro Ala Arg
                805                 810                 815

Thr Leu Lys Ser Met Lys Asp Ile Asn Lys Ser Arg Thr Leu Tyr Lys
            820                 825                 830

Ala Ile Lys Glu Ser Asp Ile Tyr Asp Lys Leu Lys Met Tyr Lys
            835                 840                 845

Thr Ser Val Pro Leu Asp Glu Leu Ser Asn Glu Ile Gly Arg Ala Arg
850                 855                 860

Ala Phe Thr Ala Gly Trp Leu Glu Arg Glu Ala Val Phe Leu His Met
865                 870                 875                 880

Glu Tyr Lys Tyr Leu Leu Ala Leu Leu Lys Ala Gly Leu Tyr Asn Glu
                885                 890                 895

Tyr Tyr Glu Asp Met Gln Thr Thr Leu Thr Ala Phe Leu Asp Pro Gln
            900                 905                 910

Val Tyr Gly Arg Ser Thr Leu Glu Asn Ser Ser Phe Ile Ala Ser Ser
            915                 920                 925
```

Val Asn Pro Asp Asp Ala Val His Gly Arg Gly Phe Val Ala Arg Leu
          930                 935                 940

Ser Gly Ser Thr Ala Glu Met Leu Ser Ile Trp Phe Ile Met Met Ala
945                 950                 955                 960

Gly Glu Lys Val Phe Thr Tyr Glu Asn Asp Lys Leu Gln Leu Glu Leu
                965                 970                 975

Ser Pro Ile Leu Pro Ala Trp Leu Phe Asp Asn Glu Gly Lys Val Ser
            980                 985                 990

Phe Thr Phe Leu Gly Lys Thr Glu Val Thr Tyr His Asn Pro Lys Lys
        995                 1000                1005

Leu Asn Thr Tyr Gly Glu Asn Lys Ala Val Ala Asp Lys Ile Ile
    1010                1015                1020

Ile Thr Val Asn Glu Asn Glu Lys Ile Glu Leu Lys Gly Asn Ile
    1025                1030                1035

Ile Thr Glu Asp Tyr Ala Lys Ala Ile Arg Asp Gly Lys Ile Asn
    1040                1045                1050

Lys Val Asp Ile Tyr Phe Lys
    1055                1060

<210> SEQ ID NO 11
<211> LENGTH: 3093
<212> TYPE: DNA
<213> ORGANISM: Lachnoclostridium phytofermentans KNHs2131

<400> SEQUENCE: 11

```
atgtttgaca acaaaggaag atttataata cgaaattatg caaaagagag tccttttgca      60
agcttttac  ctggaattag tggaaaatac ggaattccaa tctggtgttt ttatgtaaat     120
cggggacagg cagtgactag ttttggagtg ttggataaag atcattctat catggaattc     180
tatcctgcgc atcaggctta tcaaataacg aaaaccaatg ggtttcgaac ttttttaaag     240
attgaccact cctatacgga agcatttacc gaggaagaca gagagcatgc gatgtatatc     300
ggaatgaatg agctggaatt ggaagaaaag atagaacaaa aataagtgt gaatgttaca     360
tattttacct taccaaatga agcgcttggt ggattagttc gaaaagttac agtgaaaaat     420
attgatacta cggaacatct agtagaacta ttagatggta tgccttcctt aatacccttat    480
ggagtaagcc tcaattcaat gaaggagatg gggcagacca caaaagcctg gatgcaagtt     540
gaaaatttat cagagcgttt gccattttt aaagtaagag ccagtatgga ggattctgtc      600
gatgttcatg aagttattgg gggacatttc tcttttggaa ttgatggtaa ggggcttctg     660
cctgttttag tagatcctta tcttgttttt ggttacgata cttctcttac aaaggcaatt     720
ggctttaaag agggagaact caattactta ttaagaaaga atcaggtggt aaccaataat     780
cttccttgta gtttctttgc aaaacaaaaa atattaatgc cagaagaaga gtttacaatt     840
tatgaggtga ttgggcaggc aaaagagcat tgctactgtc gggaattcgc caccagttgt     900
gtgtcagagg atatttcaa gaaaaatat gaagaagcaa tcgctttaac ggaggatctt     960
tgtaaaggaa ttgaaacgaa aactgcatcg cctgtatttg atgcctattg caaacaaacc    1020
tatcttgata tatttttacg tggtggctat ccaataaagt tagggaaaga taaatattc     1080
tatctttatt ccagaaaaca tggtgatatt gagagagact ataacttttt tagcatgtta    1140
ccggagtact actctcaggg gaatgcaaat tatagagatg tgaatcaaaa cagacgatgt    1200
gacgtattat tttcacccctt tgttgaagat gaatgcatta aatgttttta taatctgatt   1260
caaatcgatg gatataatcc gttggcggtg caaaagcta cctttgtat accttcggaa     1320
```

-continued

```
aaaatggagg aagccgtatc aatactacca atcaaagaaa aggtgaatgg ttacaacttc    1380
tttcaaaact cgtttactcc agggagtttt ttgggtttct tagaacagca gggatgtact    1440
gataaagaga cactagagaa caccttatcc tctgtaatgg aagtttccga aagtgaaatc    1500
gcagcttcct tcggagaagg ttattgggtg gatcattgga cctataattt agatttggtg    1560
gaagcttttc tatcgattta tccggagaga gaagaagact tattctatca tgatattacg    1620
tatacttatt ttgaatcaat ggctatcgta aataaaaggc agaatcgtta tgttgaaact    1680
aagaatggac ttcgtcagta taagtctcta gataagggaa gtaaaaaaga agttgcgcac    1740
aagcagttac gttgtgatta tggaaaaggt tctgtgtatc aaacatcatt attagaaaaa    1800
ctttattat taatttccat caaaattgct acccttgatc cggaaggaat gggtattgag    1860
atggaagcag gaaacccgg tggtatgat gcattaaatg gtttgccggg aatctttgga    1920
tcatctatgt gtgaaacaat agaattggag cgtatgatat cctttgtttt atctatcgtg    1980
aatcgttatc caaacaatgt tccagtagcg ttggaaataa agaactaat ggaaaatctg    2040
tatgaagttt caagaagaga gattacttcc atggaggcat gggatttaag gaataatagt    2100
aaggaaaatt acagagagaa aacaaaatta ggtgtcgaag gtaccaaaga ggttctcatg    2160
gtagaagata tcagagccat gcttactacc tggtcttccc ttgtaaagaa aggaattgag    2220
aaagcagtaa agcttggaaa aggaatctgt cctacgtatt tctactacaa ggcaaaggag    2280
tatgaaaaga agaagatgg tatcttcatc aaagagtttg aacttatgtc aatgccttat    2340
ttcttagaag gtccagtcca ttaccttaag ctcgaacaga gccaagagga aaagaagaga    2400
ttatatcaag ccgtgaagga gagtaatctg tatgaccgta agcttaagat gtataaggtg    2460
aatgaatcac tgcataaggc gtcctttgaa gtaggtcgtt ccaccgcatt tacaccgggg    2520
tggcttgaaa atgagtctat ttggctccat atggaataca atattactt agaattatta    2580
aagtcagggc tatatgagga gtattttgaa gattttaaga atggcctaat accatttcta    2640
gaggaaaaga gtatggtag aagtatctta gagaattcat cgttcttagc aagcagtgca    2700
aatcctgatg agaagattca tggaaaaggc tttgttgcaa gacttagtgg ttccacagcg    2760
gaatttgttc atatgtggca gattatgatg tttggacata atccattccg gtatgagcag    2820
gaagagcttt acctatcctt agaacctatc ttaccagaat atttaattgg tgaggatggt    2880
gtaattaagg caaccttcct tggtaagata ccagtatgct atcagctttt aaagaagaaa    2940
gccttattac caggaagata taagtagaa agctatacat tacagtatga agacggtgaa    3000
ataaaacaga tttcagaatc aaagctacca tgcaaagaat caatggatgt cagagatggc    3060
agagtaaata gcatcagtgt ctctatcagt taa                                3093
```

<210> SEQ ID NO 12
<211> LENGTH: 1030
<212> TYPE: PRT
<213> ORGANISM: Lachnoclostridium phytofermentans KNHs2131

<400> SEQUENCE: 12

```
Met Phe Asp Asn Lys Gly Arg Phe Ile Ile Arg Asn Tyr Ala Lys Glu
1               5                   10                  15

Ser Pro Phe Ala Ser Phe Leu Pro Gly Ile Ser Gly Lys Tyr Gly Ile
            20                  25                  30

Pro Ile Trp Cys Phe Tyr Val Asn Arg Gly Gln Ala Val Thr Ser Phe
        35                  40                  45

Gly Val Leu Asp Lys Asp His Ser Ile Met Glu Phe Tyr Pro Ala His
    50                  55                  60
```

```
Gln Ala Tyr Gln Ile Thr Lys Thr Asn Gly Phe Arg Thr Phe Leu Lys
 65                  70                  75                  80

Ile Asp His Ser Tyr Thr Glu Ala Phe Thr Glu Glu Asp Arg Glu His
                 85                  90                  95

Ala Met Tyr Ile Gly Met Asn Glu Leu Glu Leu Glu Glu Lys Ile Glu
            100                 105                 110

Gln Lys Ile Ser Val Asn Val Thr Tyr Phe Thr Leu Pro Asn Glu Ala
        115                 120                 125

Leu Gly Gly Leu Val Arg Lys Val Thr Val Lys Asn Ile Asp Thr Thr
    130                 135                 140

Glu His Leu Val Glu Leu Leu Asp Gly Met Pro Ser Leu Ile Pro Tyr
145                 150                 155                 160

Gly Val Ser Leu Asn Ser Met Lys Glu Met Gly Gln Thr Thr Lys Ala
                165                 170                 175

Trp Met Gln Val Glu Asn Leu Ser Glu Arg Leu Pro Phe Phe Lys Val
            180                 185                 190

Arg Ala Ser Met Glu Asp Ser Val Asp Val His Glu Val Ile Gly Gly
        195                 200                 205

His Phe Ser Phe Gly Ile Asp Gly Lys Gly Leu Leu Pro Val Leu Val
    210                 215                 220

Asp Pro Tyr Leu Val Phe Gly Tyr Asp Thr Ser Leu Thr Lys Ala Ile
225                 230                 235                 240

Gly Phe Lys Glu Gly Glu Leu Asn Tyr Leu Leu Arg Lys Asn Gln Val
                245                 250                 255

Val Thr Asn Asn Leu Pro Cys Ser Phe Phe Ala Lys Gln Lys Ile Leu
            260                 265                 270

Met Pro Glu Glu Phe Thr Ile Tyr Glu Val Ile Gly Gln Ala Lys
        275                 280                 285

Ser Ile Ala Thr Val Arg Glu Phe Ala Thr Ser Cys Val Ser Glu Gly
    290                 295                 300

Tyr Phe Lys Lys Lys Tyr Glu Glu Ala Ile Ala Leu Thr Glu Asp Leu
305                 310                 315                 320

Cys Lys Gly Ile Glu Thr Lys Thr Ala Ser Pro Val Phe Asp Ala Tyr
                325                 330                 335

Cys Lys Gln Thr Tyr Leu Asp Asn Ile Leu Arg Gly Gly Tyr Pro Ile
            340                 345                 350

Lys Leu Gly Lys Asp Lys Ile Phe Tyr Leu Tyr Ser Arg Lys His Gly
        355                 360                 365

Asp Ile Glu Arg Asp Tyr Asn Phe Phe Ser Met Leu Pro Glu Tyr Tyr
    370                 375                 380

Ser Gln Gly Asn Ala Asn Tyr Arg Asp Val Asn Gln Asn Arg Arg Cys
385                 390                 395                 400

Asp Val Leu Phe Ser Pro Phe Val Glu Asp Glu Cys Ile Lys Met Phe
                405                 410                 415

Tyr Asn Leu Ile Gln Ile Asp Gly Tyr Asn Pro Leu Ala Val Gln Lys
            420                 425                 430

Ala Thr Phe Cys Ile Pro Ser Glu Lys Met Glu Glu Ala Val Ser Ile
        435                 440                 445

Leu Pro Ile Lys Glu Lys Val Asn Gly Tyr Asn Phe Phe Gln Asn Ser
    450                 455                 460

Phe Thr Pro Gly Ser Phe Leu Gly Phe Leu Glu Gln Gln Gly Cys Thr
465                 470                 475                 480
```

```
Asp Lys Glu Thr Leu Glu Asn Thr Leu Ser Ser Val Met Glu Val Ser
                485                 490                 495

Glu Ser Glu Ile Ala Ala Ser Phe Gly Glu Gly Tyr Trp Val Asp His
            500                 505                 510

Trp Thr Tyr Asn Leu Asp Leu Val Glu Ala Phe Leu Ser Ile Tyr Pro
        515                 520                 525

Glu Arg Glu Glu Asp Leu Phe Tyr His Asp Ile Thr Tyr Thr Tyr Phe
    530                 535                 540

Glu Ser Met Ala Ile Val Asn Lys Arg Gln Asn Arg Tyr Val Glu Thr
545                 550                 555                 560

Lys Asn Gly Leu Arg Gln Tyr Lys Ser Leu Asp Lys Gly Ser Lys Lys
                565                 570                 575

Glu Val Ala His Lys Gln Leu Arg Cys Asp Tyr Gly Lys Gly Ser Val
            580                 585                 590

Tyr Gln Thr Ser Leu Leu Glu Lys Leu Leu Leu Ile Ser Ile Lys
        595                 600                 605

Ile Ala Thr Leu Asp Pro Glu Gly Met Gly Ile Glu Met Glu Ala Gly
    610                 615                 620

Lys Pro Gly Trp Tyr Asp Ala Leu Asn Gly Leu Pro Gly Ile Phe Gly
625                 630                 635                 640

Ser Ser Met Cys Glu Thr Ile Glu Leu Glu Arg Met Ile Ser Phe Val
                645                 650                 655

Leu Ser Ile Val Asn Arg Tyr Pro Asn Asn Val Pro Val Ala Leu Glu
            660                 665                 670

Ile Lys Glu Leu Met Glu Asn Leu Tyr Glu Val Ser Arg Arg Glu Ile
        675                 680                 685

Thr Ser Met Glu Ala Trp Asp Leu Arg Asn Asn Ser Lys Glu Asn Tyr
    690                 695                 700

Arg Glu Lys Thr Lys Leu Gly Val Gly Thr Lys Glu Val Leu Met
705                 710                 715                 720

Val Glu Asp Ile Arg Ala Met Leu Thr Thr Trp Ser Phe Leu Val Lys
                725                 730                 735

Lys Gly Ile Glu Lys Ala Val Lys Leu Gly Lys Gly Ile Cys Pro Thr
            740                 745                 750

Tyr Phe Tyr Tyr Lys Ala Lys Glu Tyr Glu Lys Lys Glu Asp Gly Ile
        755                 760                 765

Phe Ile Lys Glu Phe Glu Leu Met Ser Met Pro Tyr Phe Leu Glu Gly
    770                 775                 780

Pro Val His Tyr Leu Lys Leu Glu Gln Ser Gln Glu Glu Lys Lys Arg
785                 790                 795                 800

Leu Tyr Gln Ala Val Lys Glu Ser Asn Leu Tyr Asp Arg Lys Leu Lys
                805                 810                 815

Met Tyr Lys Val Asn Glu Ser Leu His Lys Ala Ser Phe Glu Val Gly
            820                 825                 830

Arg Ser Thr Ala Phe Thr Pro Gly Trp Leu Glu Asn Glu Ser Ile Trp
        835                 840                 845

Leu His Met Glu Tyr Lys Tyr Tyr Leu Glu Leu Leu Lys Ser Gly Leu
    850                 855                 860

Tyr Glu Glu Tyr Phe Glu Asp Phe Lys Asn Gly Leu Ile Pro Phe Leu
865                 870                 875                 880

Glu Glu Lys Lys Tyr Gly Arg Ser Ile Leu Glu Asn Ser Ser Phe Leu
                885                 890                 895
```

```
Ala Ser Ser Ala Asn Pro Asp Glu Lys Ile His Gly Lys Gly Phe Val
            900                 905                 910

Ala Arg Leu Ser Gly Ser Thr Ala Glu Phe Val His Met Trp Gln Ile
        915                 920                 925

Met Met Phe Gly His Asn Pro Phe Arg Tyr Glu Gln Glu Leu Tyr
    930                 935                 940

Leu Ser Leu Glu Pro Ile Leu Pro Glu Tyr Leu Ile Gly Glu Asp Gly
945                 950                 955                 960

Val Ile Lys Ala Thr Phe Leu Gly Lys Ile Pro Val Cys Tyr Gln Leu
                965                 970                 975

Leu Lys Lys Lys Ala Leu Leu Pro Gly Arg Tyr Lys Val Glu Ser Tyr
            980                 985                 990

Thr Leu Gln Tyr Glu Asp Gly Glu  Ile Lys Gln Ile Ser  Glu Ser Lys
        995                1000                1005

Leu Pro  Cys Lys Glu Ser Met  Asp Val Arg Asp Gly  Arg Val Asn
   1010                1015                1020

Ser Ile  Ser Val Ser Ile Ser
   1025                1030

<210> SEQ ID NO 13
<211> LENGTH: 3288
<212> TYPE: DNA
<213> ORGANISM: Artificial sequence
<220> FEATURE:
<223> OTHER INFORMATION: PstGp1 codon-optimized and w/ additional
      C-terminal residues including 6x-His tag

<400> SEQUENCE: 13
atgcctgcat attatatgga taatcaatat tttgttatag aagaatttga taaagcaaaa      60
acatttgctt cgtttcttcc gggccttgca ggacctaaag catccctat gtggacattt     120 tatgttaata gaggacaagg aattgcatca tttggcatca gagataaaaa tagcccgatc     180
atggagttca gccctgcaaa tatcagctat aagaatgttc ctctgagcgg ctttagaacc     240
tttatcaaac tgggcggagc agtttatgaa ccgtttcaag atcaaggcga agattcttca     300
attcgccgca cgatgtctat cggacttaac gagttagtta tagaggaaac gaatcataca     360
cttaatcttc aagttaaaat cgtttatttt aatgttccgg gagatggatt tgcagcactt     420
gcacgccata cggaaattac gaatctgtca gcatcaccga tgccgctgga agttcttgat     480
ggattacctg aattacttcc gtatggcatt gataatgcag gctacaagga atgggcaat      540 ctgctgcgct cttggatgga gtttataat ctggaaaatg cagttccgtt ctttaaactg      600
cgctcttcta cgaaagatga agcagaagtt agcgaaatca aggcggaca ttttttatctg      660 agctttagcg atgaagaaga actgcttcct cctattgttg attatgaagt tatctttggc      720
cataatacgt cactggttta tcctgcttca tttgcacgcg catcacttga caactgggc      780 gcaatgcctc aaatcacagc aaacaaagtt ccgtgcgcat tcagcggcgc agcaggcaaa     840
cttggtccgg gtgaaagcct taatctgtat gcaatgatcg ccatacgag agacataggc     900 tcaatccaaa gccaaacagg ccgcctgtgc cgcgcagaat attttcgcac gaaacgcgaa     960
gaagcagcac gcatggcaga caactgact ggggatattg caacgtctac gagctctacg    1020
atgtttgatg catattgccg ccaaagctat cttgataata tgctgagagg cggctatccg    1080 gttgttttg gccaaggcca agaaacgaaa atctatcatc tgttttctcg caacatggc     1140 gacctggaac gcgattataa cttctttagc cttgcaccgg aatattattc acaaggcaat    1200
ggcaattttc gcgatatgaa tcaaaataga cgcaatgatg ttctgtttca tccggaagcc    1260
```

-continued

```
ggggcgttta atatctatat gttttttcagc cttatccaag cagatggcta taatccgtta   1320
caagttaaag gatctacatt tcaagttccg gaagaacgcg cagcagaact tgcatcactg   1380
ctggaacaag cagttggctc acatagacgc gaactgtcag caattgcagc aaaaccgttt   1440
acaccgggcc aaatcatcca ttatctgtgc gatcatgaaa tcatgcttaa tgttagcgaa   1500
gaagaatttc tggataaact gctgggactg tcagcacaaa atatagaggc ctcctttggc   1560
gaaggctatt ggattgatca ttggacgtat aatatggatc tggttgattc atatcgctca   1620
gttttttcctg ataagatgga agaactgctg tatacaccgg gcacgtgccg cttctttgat   1680
agcccggtta gagttcttcc tcgctcagaa aaaacggttc ttaaagatgg caaagttcgc   1740
caatatggct cagcagttca tgatgaagaa aaactgaaac gcctgggagg tggcatgtca   1800
gatacacgct ggttacgcac acaacatggc acgggcgaag tttatcgcac ggatctgttt   1860
gcaaaaatgc tgagccttgc actgatcaaa atgacgacat tagatccgta tggcatgggc   1920
atagagatgg agggcgataa accgggctgg aatgatgcta tgaatggttt accgggactg   1980
tttggctcag gcatgggcga aacgtatgaa cttaaacgcc ttgttctgtt tatccttgaa   2040
gcactgagcg catgccggg cggcgcagtt gttagcggag atccgggaga ttcaggatta   2100
gcaggacgca aagttagact tcctctggaa atggcagaat tactgtcaga aacggatagc   2160
gttctgtctc gccgcgaaag cggagacatt tctgatctgg aatgctggga tctgcttgca   2220
acagcacgcg aacgctatag agaatctatc cgctttggcc tgagcggcga tgaacaagaa   2280
atcgttttg cagcacttga accggttttt aaacgctttc tgggccgcct gaacgaggga   2340
attgcaaaag cagttaaatt gggcggagga ctggttccga cgtattttcg ctttgaagca   2400
gaagattatg aacctcttaa aggcggcgat ggcggcccgg ttatctctag ctatggcctt   2460
ccggttgtta gcgtttctcg ctttcgcgca gaagcattac ctgcatttct gaaggaccg   2520
gttcatggac ttaaacttgc agaatctaaa gaagaagcac aaggcatcta tagagcagtt   2580
cgctctagcg gcttatatga tgaaaaatta ggcatgtata agacgagcgt tagccttgaa   2640
caacaacctc aagaaatcgg acgcattcgc gcgtttacac cggctggtt agaacgcgaa   2700
tcaatctttc ttcacatgtc atacaagtat gttcttgaac tgcttaaaac gggactgaca   2760
ggcacatttt atgaagagtt taaacgcgca ctgatcccgt ttcaagatcc tgcagtttat   2820
ggacgctcta cacttgaaaa tagctcattt cttgcatcta cgttaatcc tgatccggga   2880
gttcatggcc gcggctttgt tgcacgcctg agcggctcta cggcagaatt tctgtctatg   2940
tggtctctta tgatggcagg cagtagaccg tttagactga gcggagatgg cgatctggtt   3000
ctggaacttg cacctgcact tccgggctgg ctctttaaag atgatggccg cctgagcttt   3060
cgctttctgg gctcagttcg cgttacgtat cttaacgagc gccgcgcaga tacgtttggc   3120
gaaaattgcg cagcaattcg ccgcatcagc gttaaagatg gcgcaggcaa tacactgacg   3180
gttgaaggct cagttctgtc aggcaaatta gcagaagata ttcgcgcagg ccgctatacg   3240
gaacttgaag ttgttcttga actcgagcac caccaccacc accactga                3288
```

<210> SEQ ID NO 14
<211> LENGTH: 1095
<212> TYPE: PRT
<213> ORGANISM: Artificial sequence
<220> FEATURE:
<223> OTHER INFORMATION: PstGp1 w/ additional C-terminal residues including 6x-His tag

<400> SEQUENCE: 14

```
Met Pro Ala Tyr Tyr Met Asp Asn Gln Tyr Phe Val Ile Glu Glu Phe
1               5                   10                  15

Asp Lys Ala Lys Thr Phe Ala Ser Phe Leu Pro Gly Leu Ala Gly Pro
            20                  25                  30

Lys Gly Ile Pro Met Trp Thr Phe Tyr Val Asn Arg Gly Gln Gly Ile
        35                  40                  45

Ala Ser Phe Gly Ile Arg Asp Lys Asn Ser Pro Ile Met Glu Phe Ser
    50                  55                  60

Pro Ala Asn Ile Ser Tyr Lys Asn Val Pro Leu Ser Gly Phe Arg Thr
65                  70                  75                  80

Phe Ile Lys Leu Gly Gly Ala Val Tyr Glu Pro Phe Gln Asp Gln Gly
                85                  90                  95

Glu Asp Ser Ser Ile Arg Arg Thr Met Ser Ile Gly Leu Asn Glu Leu
            100                 105                 110

Val Ile Glu Glu Thr Asn His Thr Leu Asn Leu Gln Val Lys Ile Val
        115                 120                 125

Tyr Phe Asn Val Pro Gly Asp Gly Phe Ala Ala Leu Ala Arg His Thr
    130                 135                 140

Glu Ile Thr Asn Leu Ser Ala Ser Pro Met Pro Leu Glu Val Leu Asp
145                 150                 155                 160

Gly Leu Pro Glu Leu Leu Pro Tyr Gly Ile Asp Asn Ala Gly Tyr Lys
                165                 170                 175

Glu Met Gly Asn Leu Leu Arg Ser Trp Met Glu Val Tyr Asn Leu Glu
            180                 185                 190

Asn Ala Val Pro Phe Phe Lys Leu Arg Ser Ser Thr Lys Asp Glu Ala
        195                 200                 205

Glu Val Ser Glu Ile Lys Gly Gly His Phe Tyr Leu Ser Phe Ser Asp
    210                 215                 220

Glu Glu Glu Leu Leu Pro Pro Ile Val Asp Tyr Glu Val Ile Phe Gly
225                 230                 235                 240

His Asn Thr Ser Leu Val Tyr Pro Ala Ser Phe Ala Arg Ala Ser Leu
                245                 250                 255

Glu Gln Leu Gly Ala Met Pro Gln Ile Thr Ala Asn Lys Val Pro Cys
            260                 265                 270

Ala Phe Ser Gly Ala Ala Gly Lys Leu Gly Pro Gly Glu Ser Leu Asn
        275                 280                 285

Leu Tyr Ala Met Ile Gly His Thr Arg Asp Ile Gly Ser Ile Gln Ser
    290                 295                 300

Gln Thr Gly Arg Leu Cys Arg Ala Glu Tyr Phe Arg Thr Lys Arg Glu
305                 310                 315                 320

Glu Ala Ala Arg Met Ala Glu Gln Leu Thr Gly Asp Ile Ala Thr Ser
                325                 330                 335

Thr Ser Ser Thr Met Phe Asp Ala Tyr Cys Arg Gln Ser Tyr Leu Asp
            340                 345                 350

Asn Met Leu Arg Gly Gly Tyr Pro Val Val Phe Gly Gln Gly Gln Glu
        355                 360                 365

Thr Lys Ile Tyr His Leu Phe Ser Arg Lys His Gly Asp Leu Glu Arg
    370                 375                 380

Asp Tyr Asn Phe Phe Ser Leu Ala Pro Glu Tyr Tyr Ser Gln Gly Asn
385                 390                 395                 400

Gly Asn Phe Arg Asp Met Asn Gln Asn Arg Arg Asn Asp Val Leu Phe
                405                 410                 415
```

His Pro Glu Ala Gly Ala Phe Asn Ile Tyr Met Phe Phe Ser Leu Ile
            420                 425                 430

Gln Ala Asp Gly Tyr Asn Pro Leu Gln Val Lys Gly Ser Thr Phe Gln
        435                 440                 445

Val Pro Glu Glu Arg Ala Ala Glu Leu Ala Ser Leu Leu Glu Gln Ala
    450                 455                 460

Val Gly Ser His Arg Arg Glu Leu Ser Ala Ile Ala Ala Lys Pro Phe
465                 470                 475                 480

Thr Pro Gly Gln Ile Ile His Tyr Leu Cys Asp His Glu Ile Met Leu
                485                 490                 495

Asn Val Ser Glu Glu Phe Leu Asp Lys Leu Leu Gly Leu Ser Ala
            500                 505                 510

Gln Asn Ile Glu Ala Ser Phe Gly Glu Gly Tyr Trp Ile Asp His Trp
        515                 520                 525

Thr Tyr Asn Met Asp Leu Val Asp Ser Tyr Arg Ser Val Phe Pro Asp
    530                 535                 540

Lys Met Glu Glu Leu Leu Tyr Thr Pro Gly Thr Cys Arg Phe Phe Asp
545                 550                 555                 560

Ser Pro Val Arg Val Leu Pro Arg Ser Glu Lys Thr Val Leu Lys Asp
                565                 570                 575

Gly Lys Val Arg Gln Tyr Gly Ser Ala Val His Asp Glu Glu Lys Leu
        580                 585                 590

Glu Arg Leu Gly Gly Met Ser Asp Thr Arg Trp Leu Arg Thr Gln
    595                 600                 605

His Gly Thr Gly Glu Val Tyr Arg Thr Asp Leu Phe Ala Lys Met Leu
            610                 615                 620

Ser Leu Ala Leu Ile Lys Met Thr Thr Leu Asp Pro Tyr Gly Met Gly
625                 630                 635                 640

Ile Glu Met Glu Gly Asp Lys Pro Gly Trp Asn Asp Ala Met Asn Gly
                645                 650                 655

Leu Pro Gly Leu Phe Gly Ser Gly Met Gly Glu Thr Tyr Glu Leu Lys
        660                 665                 670

Arg Leu Val Leu Phe Ile Leu Glu Ala Leu Ser Gly Met Pro Gly Gly
    675                 680                 685

Ala Val Val Ser Gly Asp Pro Gly Asp Ser Gly Leu Ala Gly Arg Lys
            690                 695                 700

Val Arg Leu Pro Leu Glu Met Ala Glu Leu Leu Ser Glu Thr Asp Ser
705                 710                 715                 720

Val Leu Ser Arg Arg Glu Ser Gly Asp Ile Ser Asp Leu Glu Cys Trp
                725                 730                 735

Asp Leu Leu Ala Thr Ala Arg Glu Arg Tyr Arg Glu Ser Ile Arg Phe
        740                 745                 750

Gly Leu Ser Gly Asp Glu Gln Glu Ile Val Phe Ala Ala Leu Glu Pro
    755                 760                 765

Val Phe Lys Arg Phe Leu Gly Arg Leu Asn Glu Gly Ile Ala Lys Ala
            770                 775                 780

Val Lys Leu Gly Gly Gly Leu Val Pro Thr Tyr Phe Arg Phe Glu Ala
785                 790                 795                 800

Glu Asp Tyr Glu Pro Leu Lys Gly Gly Asp Gly Pro Val Ile Ser
                805                 810                 815

Ser Tyr Gly Leu Pro Val Val Ser Val Ser Arg Phe Arg Ala Glu Ala
        820                 825                 830

Leu Pro Ala Phe Leu Glu Gly Pro Val His Gly Lys Leu Ala Glu
    835                 840                 845

Ser Lys Glu Glu Ala Gln Gly Ile Tyr Arg Ala Val Arg Ser Ser Gly
    850                 855                 860

Leu Tyr Asp Glu Lys Leu Gly Met Tyr Lys Thr Ser Val Ser Leu Glu
865                 870                 875                 880

Gln Gln Pro Gln Glu Ile Gly Arg Ile Arg Ala Phe Thr Pro Gly Trp
                885                 890                 895

Leu Glu Arg Glu Ser Ile Phe Leu His Met Ser Tyr Lys Tyr Val Leu
            900                 905                 910

Glu Leu Leu Lys Thr Gly Leu Thr Gly Thr Phe Tyr Glu Glu Phe Lys
        915                 920                 925

Arg Ala Leu Ile Pro Phe Gln Asp Pro Ala Val Tyr Gly Arg Ser Thr
    930                 935                 940

Leu Glu Asn Ser Ser Phe Leu Ala Ser Ser Val Asn Pro Asp Pro Gly
945                 950                 955                 960

Val His Gly Arg Gly Phe Val Ala Arg Leu Ser Gly Ser Thr Ala Glu
                965                 970                 975

Phe Leu Ser Met Trp Ser Leu Met Met Ala Gly Ser Arg Pro Phe Arg
            980                 985                 990

Leu Ser Gly Asp Gly Asp Leu Val  Leu Glu Leu Ala Pro  Ala Leu Pro
        995                 1000                 1005

Gly Trp  Leu Phe Lys Asp Asp  Gly Arg Leu Ser Phe  Arg Phe Leu
    1010                 1015                 1020

Gly Ser  Val Arg Val Thr Tyr  Leu Asn Glu Arg Arg  Ala Asp Thr
    1025                 1030                 1035

Phe Gly  Glu Asn Cys Ala Ala  Ile Arg Arg Ile Ser  Val Lys Asp
    1040                 1045                 1050

Gly Ala  Gly Asn Thr Leu Thr  Val Glu Gly Ser Val  Leu Ser Gly
    1055                 1060                 1065

Lys Leu  Ala Glu Asp Ile Arg  Ala Gly Arg Tyr Thr  Glu Leu Glu
    1070                 1075                 1080

Val Val  Leu Glu Leu Glu His  His His His His His
    1085                 1090                 1095

<210> SEQ ID NO 15
<211> LENGTH: 3258
<212> TYPE: DNA
<213> ORGANISM: Artificial sequence
<220> FEATURE:
<223> OTHER INFORMATION: GmaGp1 codon-optimized and w/ additional
      C-terminal residues including 6x-His tag

<400> SEQUENCE: 15
atggcaaatt atagctttga acaaaatacg tttgttattg aaaattatca tgaagcaaaa      60
ccttttgctt cgtttctgcc gggccttgca ggacttaaag gaatccctat gtggacgttt     120
tatgttaata gaggccaagc aattagcggc tttggcatca agataaaaaa tagcccgatc     180
atggagttta gcccggcatc tattgcatac aagacggtta gcgcatcagg ctttcgcaca     240
ttcatcaaaa tcggcggtga actgtatgaa ccgtttcaaa cgtttcgccc tgatcctgat     300
attcatagag ttatgcgcgt taaagcaaac gaaatcagcc ttacggaaac acatagtcgt     360
catggcctta agttaatgt tgtttatttt catgttccgg agaagatttt gcagcactg      420 gttcgccatg ttgaaataga atcactgggc gatggacaac gcgaaattga gctgctggat     480
ggattaccgg aaattctgcc gtatggagtt ggcaatggcg agttcaaaga aatcggccat     540

```
ctgctgcgct cttggatgga agttgaaaat cttcctaata ggataccgtt ttacaagaat    600
cgctcttcta cacatgatga agcagaagtt agcgaagttg ttagcggcca ttttatctg    660
agctttagcg atgaagaaga tcttctgcgc ccgattgttg atccggatct ggttttggc    720
gaaaatagct cactgagcta tccggatgtt tttgcagcag ttcctcttgc agaactgagc    780
gaacgcatcc cgtatgcata taacaagatc ccgtgcggct ttagcggcaa agcgcaaaa    840
cttgcaccgg aggcaaact taatctgtat acgctgatcg gcaatgttag ccgcgttgaa    900
cgcatcaatg caaaagcagc atcagtttgc tcagcagcat atattgcaga aaacgcgaa    960
gaagcaaata gactggttga tgaactgaca gcagatattt ctacacgcac aggggttccg   1020
gttatagacg catacgcacg ccaatgctat cttgataatt ttctgcgagg gggctatccg   1080
tttatctttg ggggagatgg caacaatggc tcaggcacga cgtctaaagt tgttcatctg   1140
tttagccgca acatggcga tcttgaacgc gattataact tctttagcct gctgccggaa   1200
ttttattctc aaggcaatgg caattttaga gatgcaaatc aaaatagacg caatgatgta   1260
ttctttcaac ctaaagttgg cacgtttaat attcgcatgt ttttcagcct tatgcaagca   1320
gatggctata tccgctgggg agttgaagga cgacgtttta cggttccggc agcaaaagca   1380
gcagaactgg atgcacatct tgcagcatca gttaaaaacg acaagcaga tctgacggca   1440
cttgcacgca aagcctttac accgggcaaa gttattaatc tgattgcaga tagaaatata   1500
gaattacttc aaccggaagc agattttctt aacggcctgc tgggccttgc agaacaaaat   1560
attgaagcac gctttaacga gggctattgg tcagatcatt ggacgtataa tatggatctg   1620
gttgatgcat atctgtcagt ttttccggat aaaaagaacg agctgctgtt tggcgatgaa   1680
acgtatgcat attttgattc accggttcgc gttcttcctc gctctgaaaa atatgttgtt   1740
aaagatggcg cagttcgcca atatggctca gttgttcatg atgaagaaaa aatgcaaaca   1800
ctgggaattg cacttaatgg cacacattgg cttaaaacac aacaaggacg cggcgaaatc   1860
tatagaacga accttcttgt taaaatcctg tctctgtctc tgtctaaatt tgcaacatta   1920
gatccgtatg gcatgggaat tgagatggaa ggcaataagc cgggctggaa tgatgcgatg   1980
aacggtctgc cgggacttat cggctcaggc atgagcgaaa cgtttgaact taaacgcatg   2040
cttcaatttc tggcaacggc atgcgcagaa gcatcagata gagaagttcg cgttcctgaa   2100
gaaatctatc gctttcttca aaaaacagca aatcttgcag aacaacgcga aaaaggcgaa   2160
cttgatgcat ttccgtattg ggatggagtt gcagcagcac gcgaagatta tagagatgaa   2220
attcgctttg gaattacagg cgcagaaaca gcagttagcc ttaaagatct tcatgcaatc   2280
tctcgcacgt ttcttcaagt tgttgacctc ggaattgaga gggcagttga aatgggaggc   2340
ggaatcgttc cgacgtattt tcgctttgaa gcagaagaat ttgaaacgat gctggatgca   2400
tcaggcaaac ctgcaatgtc acattatgga ttacctaaag caattgttcg caaatttcaa   2460
ggaattgcac ttcctcattt tcttgaagga ccggcacgct ggcttaaaac ggttgataat   2520
gcagaagaag cacgcgatat atacaatcgc atcaaagcaa cggatctgta tgatcctaaa   2580
cttaaaatgt acaagacgag cgttagcctg gaaaatgagt cacttgaaat cggccgcatc   2640
cgcgctttta caccgggctg gttagaacgc gaaagcgttt ttatgcacat gagctacaag   2700
tatgttcttg aattacttaa aaatggcctg tatgaagaat atgaagaaga aatgcaacat   2760
agcctggttc cgtttcttga tcctgcaatc tatgccgct ctacactgga aaatagctcg   2820
tttattgcaa cgagcgttaa tcctgatcct caaacattag gccgcggctt ttatgcacgc   2880
ctgtcaggct ctacggcaga atttctgtct atgtgggttg gaatgatggc aggaacacct   2940
```

```
tttcatgtta cggaagatgg ccgcctggca cttgagttta aaccggttct gccgggctgg    3000
ttatttgatg cagaaggccg cattgcattt cgctttctgg gcaaaacgga agttagctat    3060
cgcaatcctc gcaaagcatc tacgtatggc gaaaatgcag cacgcatcgc atcacttaaa    3120
ctgacagcag aagatggcga acaacatacg gttaatggct cagttgttta tggcgaatgg    3180
gcagaaaaag ttcgcaatgg cgaaatcgca gcaatagaaa tagagctgag actcgagcac    3240
caccaccacc accactga                                                  3258
```

<210> SEQ ID NO 16
<211> LENGTH: 1085
<212> TYPE: PRT
<213> ORGANISM: Artificial sequence
<220> FEATURE:
<223> OTHER INFORMATION: GmaGp1 w/ additional C-terminal residues
      including 6x-His tag

<400> SEQUENCE: 16

```
Met Ala Asn Tyr Ser Phe Glu Gln Asn Thr Phe Val Ile Glu Asn Tyr
1               5                   10                  15

His Glu Ala Lys Pro Phe Ala Ser Phe Leu Pro Gly Leu Ala Gly Leu
            20                  25                  30

Lys Gly Ile Pro Met Trp Thr Phe Tyr Val Asn Arg Gly Gln Ala Ile
        35                  40                  45

Ser Gly Phe Gly Ile Lys Asp Lys Asn Ser Pro Ile Met Glu Phe Ser
    50                  55                  60

Pro Ala Ser Ile Ala Tyr Lys Thr Val Ser Ala Ser Gly Phe Arg Thr
65                  70                  75                  80

Phe Ile Lys Ile Gly Gly Glu Leu Tyr Glu Pro Phe Gln Thr Phe Arg
                85                  90                  95

Pro Asp Pro Asp Ile His Arg Val Met Arg Val Lys Ala Asn Glu Ile
            100                 105                 110

Ser Leu Thr Glu Thr His Ser Arg His Gly Leu Lys Val Asn Val Val
        115                 120                 125

Tyr Phe His Val Pro Gly Glu Asp Phe Ala Ala Leu Val Arg His Val
    130                 135                 140

Glu Ile Glu Ser Leu Gly Asp Gly Gln Arg Glu Ile Glu Leu Leu Asp
145                 150                 155                 160

Gly Leu Pro Glu Ile Leu Pro Tyr Gly Val Gly Asn Gly Glu Phe Lys
                165                 170                 175

Glu Ile Gly His Leu Leu Arg Ser Trp Met Glu Val Glu Asn Leu Pro
            180                 185                 190

Asn Arg Ile Pro Phe Tyr Lys Asn Arg Ser Ser Thr His Asp Glu Ala
        195                 200                 205

Glu Val Ser Glu Val Val Ser Gly His Phe Tyr Leu Ser Phe Ser Asp
    210                 215                 220

Glu Glu Asp Leu Leu Arg Pro Ile Val Asp Pro Asp Leu Val Phe Gly
225                 230                 235                 240

Glu Asn Ser Ser Leu Ser Tyr Pro Asp Val Phe Ala Ala Val Pro Leu
                245                 250                 255

Ala Glu Leu Ser Glu Arg Ile Pro Tyr Ala Tyr Asn Lys Ile Pro Cys
            260                 265                 270

Gly Phe Ser Gly Lys Ser Ala Lys Leu Ala Pro Gly Gly Lys Leu Asn
        275                 280                 285

Leu Tyr Thr Leu Ile Gly Asn Val Ser Arg Val Glu Arg Ile Asn Ala
    290                 295                 300
```

```
Lys Ala Ala Ser Val Cys Ser Ala Ala Tyr Ile Ala Glu Lys Arg Glu
305                 310                 315                 320

Glu Ala Asn Arg Leu Val Asp Glu Leu Thr Ala Asp Ile Ser Thr Arg
            325                 330                 335

Thr Gly Val Pro Val Ile Asp Ala Tyr Ala Arg Gln Cys Tyr Leu Asp
            340                 345                 350

Asn Phe Leu Arg Gly Gly Tyr Pro Phe Ile Phe Gly Asp Gly Asn
        355                 360                 365

Asn Gly Ser Gly Thr Thr Ser Lys Val Val His Leu Phe Ser Arg Lys
    370                 375                 380

His Gly Asp Leu Glu Arg Asp Tyr Asn Phe Phe Ser Leu Leu Pro Glu
385                 390                 395                 400

Phe Tyr Ser Gln Gly Asn Gly Asn Phe Arg Asp Ala Asn Gln Asn Arg
                405                 410                 415

Arg Asn Asp Val Phe Phe Gln Pro Lys Val Gly Thr Phe Asn Ile Arg
            420                 425                 430

Met Phe Phe Ser Leu Met Gln Ala Asp Gly Tyr Asn Pro Leu Gly Val
        435                 440                 445

Glu Gly Thr Thr Phe Thr Val Pro Ala Ala Lys Ala Ala Glu Leu Asp
450                 455                 460

Ala His Leu Ala Ala Ser Val Lys Asn Gly Gln Ala Asp Leu Thr Ala
465                 470                 475                 480

Leu Ala Arg Lys Ala Phe Thr Pro Gly Lys Val Ile Asn Leu Ile Ala
                485                 490                 495

Asp Arg Asn Ile Glu Leu Leu Gln Pro Glu Ala Asp Phe Leu Asn Gly
            500                 505                 510

Leu Leu Gly Leu Ala Glu Gln Asn Ile Glu Ala Arg Phe Asn Glu Gly
        515                 520                 525

Tyr Trp Ser Asp His Trp Thr Tyr Asn Met Asp Leu Val Asp Ala Tyr
    530                 535                 540

Leu Ser Val Phe Pro Asp Lys Lys Asn Glu Leu Leu Phe Gly Asp Glu
545                 550                 555                 560

Thr Tyr Ala Tyr Phe Asp Ser Pro Val Arg Val Leu Pro Arg Ser Glu
                565                 570                 575

Lys Tyr Val Val Lys Asp Gly Ala Val Arg Gln Tyr Gly Ser Val Val
            580                 585                 590

His Asp Glu Glu Lys Met Gln Thr Leu Gly Ile Ala Leu Asn Gly Thr
        595                 600                 605

His Trp Leu Lys Thr Gln Gln Gly Arg Gly Glu Ile Tyr Arg Thr Asn
    610                 615                 620

Leu Leu Val Lys Ile Leu Ser Leu Ser Leu Ser Lys Phe Ala Thr Leu
625                 630                 635                 640

Asp Pro Tyr Gly Met Gly Ile Glu Met Glu Gly Asn Lys Pro Gly Trp
                645                 650                 655

Asn Asp Ala Met Asn Gly Leu Pro Gly Leu Ile Gly Ser Gly Met Ser
            660                 665                 670

Glu Thr Phe Glu Leu Lys Arg Met Leu Gln Phe Leu Ala Thr Ala Cys
        675                 680                 685

Ala Glu Ala Ser Asp Arg Glu Val Arg Val Pro Glu Glu Ile Tyr Arg
    690                 695                 700

Phe Leu Gln Lys Thr Ala Asn Leu Ala Glu Gln Arg Glu Lys Gly Glu
705                 710                 715                 720
```

```
Leu Asp Ala Phe Pro Tyr Trp Asp Gly Val Ala Ala Arg Glu Asp
            725                 730                 735

Tyr Arg Asp Glu Ile Arg Phe Gly Ile Thr Gly Ala Glu Thr Ala Val
        740                 745                 750

Ser Leu Lys Asp Leu His Ala Ile Ser Arg Thr Phe Leu Gln Val Val
        755                 760                 765

Asp Leu Gly Ile Glu Arg Ala Val Glu Met Gly Gly Ile Val Pro
    770                 775                 780

Thr Tyr Phe Arg Phe Glu Ala Glu Glu Phe Glu Thr Met Leu Asp Ala
785                 790                 795                 800

Ser Gly Lys Pro Ala Met Ser His Tyr Gly Leu Pro Lys Ala Ile Val
                805                 810                 815

Arg Lys Phe Gln Gly Ile Ala Leu Pro His Phe Leu Glu Gly Pro Ala
                820                 825                 830

Arg Trp Leu Lys Thr Val Asp Asn Ala Glu Glu Ala Arg Asp Ile Tyr
                835                 840                 845

Asn Arg Ile Lys Ala Thr Asp Leu Tyr Asp Pro Lys Leu Lys Met Tyr
    850                 855                 860

Lys Thr Ser Val Ser Leu Glu Asn Glu Ser Leu Glu Ile Gly Arg Ile
865                 870                 875                 880

Arg Ala Phe Thr Pro Gly Trp Leu Glu Arg Glu Ser Val Phe Met His
                885                 890                 895

Met Ser Tyr Lys Tyr Val Leu Glu Leu Leu Lys Asn Gly Leu Tyr Glu
                900                 905                 910

Glu Tyr Glu Glu Glu Met Gln His Ser Leu Val Pro Phe Leu Asp Pro
            915                 920                 925

Ala Ile Tyr Gly Arg Ser Thr Leu Glu Asn Ser Ser Phe Ile Ala Thr
    930                 935                 940

Ser Val Asn Pro Asp Pro Gln Thr Leu Gly Arg Gly Phe Tyr Ala Arg
945                 950                 955                 960

Leu Ser Gly Ser Thr Ala Glu Phe Leu Ser Met Trp Val Gly Met Met
                965                 970                 975

Ala Gly Thr Pro Phe His Val Thr Glu Asp Gly Arg Leu Ala Leu Glu
            980                 985                 990

Phe Lys Pro Val Leu Pro Gly Trp  Leu Phe Asp Ala Glu  Gly Arg Ile
        995                 1000                1005

Ala Phe Arg Phe Leu Gly Lys  Thr Glu Val Ser Tyr  Arg Asn Pro
    1010                1015                1020

Arg Lys Ala Ser Thr Tyr Gly  Glu Asn Ala Ala Arg  Ile Ala Ser
    1025                1030                1035

Leu Lys Leu Thr Ala Glu Asp  Gly Glu Gln His Thr  Val Asn Gly
    1040                1045                1050

Ser Val Val Tyr Gly Glu Trp  Ala Glu Lys Val Arg  Asn Gly Glu
    1055                1060                1065

Ile Ala Ala Ile Glu Ile Glu  Leu Arg Leu Glu His  His His
    1070                1075                1080

His His
    1085

<210> SEQ ID NO 17
<211> LENGTH: 3252
<212> TYPE: DNA
<213> ORGANISM: Artificial sequence
```

<220> FEATURE:
<223> OTHER INFORMATION: PspGp2 codon-optimized and w/ additional
    C-terminal residues including 6x-His tag

<400> SEQUENCE: 17

```
atgtctaatt attattttga atcaggcaat tttgttatgg aacaatttga tacaggcaaa      60
ccgttttcta gctttctgcc gggactggca ggacttaaag gcatcccgat gtggacattt     120
tatgttaata gaggccaagc aatctgctca tttggagtta gagataaaaa tagcccgatc     180
atggagttta gccctgcaaa tatcagctac aaggatgttg aacgacggg ctttcgcacg      240
tttatcaaaa tcaagggtga acaagaaatc tatgaaccgt tcaaagcgc acgcccagat     300
cctgcagcaa aacgcatcat gacgattctg ccgaatggcc ttacgctgga agaaagccat     360
gcaggacatg gcctgaaaac gacggttcat tattttaatc ttcctaatga tgattatgca     420
gcactggttc gccgcgttga aattgaaaat atcggcggca agaaataga attagaactg     480
atggatggat taccggaaat ccttccgtat ggcgttgaaa attcaggata caaagaaatc     540
ggcaatctgc tgcgctcttg gatggatgtt tataatctgg aaaatggcat cccgttttac     600
aagctacgct cttcaacgaa tgattcagca caagttagcg aaattacgaa tggccatttt     660
tatctgagct ttacaggcga gggcgaaaaa gttgcaccga tcgttgattt tgaactgatc     720
tttggaggca atacgtcact gacgtatccg gatcgctttg caggacttac actgagcgaa     780
ctgagcgaac ttcctcaata tccggttaat aaggttccgt gcggctttag cggagttgca     840
cgccgccttg caccgggctc tagcctgaca cttaatacac tggttggcca tgttaatgat     900
atagacaaaa ttaataagaa agcagaacat ctgtgccgcg atgaatatat cctgtctaaa     960
agccaagaag cagcaggcct gacggaagaa ctgacggaag atattgcaac acatacgtct    1020
tcagcagttt ttgatgcata ttgccgccaa agctacctag ataattttct gagaggtggc    1080
tatccgttta tctttgataa cggtggagat ggatttgttg ttcatctgta tagccgcaaa    1140
catggagatc ttgaacgcga ttataacttc tttagccttg caccggaata ttattcacaa    1200
ggcaatggca attttagaga tatgaatcaa aatagacgca atgatgtgtt ctttaatcct    1260
aaagttggca gttttaatat caaaatgttt tatagcctga tccaagcaga tggctataat    1320
cctctgagcg ttcaaggaac gacgtttgaa gttaaatcag attctcgcgc aaaagcagca    1380
gagtggatcg gcgaagcagc agcagatcat caagcagaac tggttaaact gtgcaattct    1440
cgctttacac cgggctctct gatcaattat attgcagatc ataatgttac acttaaagtt    1500
agcgaacaag aatttctgtc aggattactt gcactgtcac aacaaaatat agaggcagca    1560
tttggcgaag gcttttggtc agatcattgg acgtataatc ttgatctggt tgttggctat    1620
cttgacatat ttccggataa aaaacaagaa ctgctgtttg gagataatac gtatgcattt    1680
tatgattcac ctgcctatgt tctgcctcgc tcagaaaaat atgttatcag cgatggcaaa    1740
gcacgccaat atggcgcact gctggaagat gaagaaaaac tgcataaact taagtggaaa    1800
gccggggata cacattggtt acgcgcagaa ggcggacaag gcgcaatcta tcatacgaat    1860
ctgtttgtta aaatgctgtc tcttgcactt aataagtttg caacattaga tccgtatggc    1920
atgggagttg agatgaaagg caacaagccg gctggaatg atgctatgaa tggccttccg    1980
ggcctgtttg gctcaggcat gtcagaaacg tttgaactta acgcacggt tgtttttctg    2040
ctggatgttc ttaatggcgc agaaaatgtt caaggcgcag ttaaactgcc ggaagaaatt    2100
gcagaactgc ttgaagcagt ttatcatgca gttacgcag ttcttgcagg cgatgttgaa    2160
caattcaatt attgggatac ggttgcaagc gcacgcgaag catatagagc atctattcgc    2220
```

-continued

```
tttggcatca cgggagttga aagcgcagtt acacttgaac atattcgcga agcactgtct    2280
aaatttctgg ttaaaataga tgaaggcatc aacaaggcag ttgaaatggg caatggcctg    2340
acacctacgt attttcgctt tgaagcagaa aaatttcatc aagttacaga tgcagaagga    2400
caaccggtta ttagcggcta tggacttcct aaagcagttg ttgaagagtt caaagcatac    2460
gcattaccgt attttcttga aggacctacg cgctggctta aaacgatgaa aaatccggtt    2520
caagcaaaag aaatctataa tctgatcaaa caaacggaac tgtatgatag agcaacgtct    2580
atgtatcaaa cgagcgttag cttagaaggc gaatcacatg aaatcggccg catgcgagcg    2640
ttcacaccgg gctggttaga acgcgaatct aattttcttc acatgagcta caagtatctg    2700
ctggaattac ttaagggagg actgtatgaa gaattttatg gcgaacttaa aacgagcctg    2760
gttccgtttc ttgatccggc agtttatggc cgctctacat agaaaatag cagcttcatt     2820 gcaacgggag gcaatcctga tcctaacaat catggccgcg gctttgttgc acgcctgagc    2880
ggctctacgg cagaatttct gtctatgtgg cgcacgatga tggcaggatc acatgttttt    2940
cgccttgaag atggcgcact gacgctgtct cttgatccgg ttcttccggg ctggctgttt    3000
gatgaagaag gcaatctgag ctttacgttt ctgggcaata cggaagttat ctattcaaat    3060
cctaaacgcg aaaatacgtt tggagagaaa aaagttagca tccaaagcct tatgctggtt    3120
tatcgcaatg gcacgatgac gaaaatctca ggcgcatttg ttcgcggcga agaagcagaa    3180
gcacttcgcc gcggcgaaat cgcacaaatc caagcagttc ttgcactcga gcaccaccac    3240
caccaccact ga                                                         3252
```

<210> SEQ ID NO 18
<211> LENGTH: 1083
<212> TYPE: PRT
<213> ORGANISM: Artificial sequence
<220> FEATURE:
<223> OTHER INFORMATION: PspGp2 w/ additional C-terminal residues including 6x-His tag

<400> SEQUENCE: 18

```
Met Ser Asn Tyr Tyr Phe Glu Ser Gly Asn Phe Val Met Glu Gln Phe
1               5                   10                  15

Asp Thr Gly Lys Pro Phe Ser Ser Phe Leu Pro Gly Leu Ala Gly Leu
            20                  25                  30

Lys Gly Ile Pro Met Trp Thr Phe Tyr Val Asn Arg Gly Gln Ala Ile
        35                  40                  45

Cys Ser Phe Gly Val Arg Asp Lys Asn Ser Pro Ile Met Glu Phe Ser
    50                  55                  60

Pro Ala Asn Ile Ser Tyr Lys Asp Val Gly Thr Thr Gly Phe Arg Thr
65                  70                  75                  80

Phe Ile Lys Ile Lys Gly Glu Gln Glu Ile Tyr Glu Pro Phe Gln Ser
                85                  90                  95

Ala Arg Pro Asp Pro Ala Ala Lys Arg Ile Met Thr Ile Leu Pro Asn
            100                 105                 110

Gly Leu Thr Leu Glu Glu Ser His Ala Gly His Gly Leu Lys Thr Thr
        115                 120                 125

Val His Tyr Phe Asn Leu Pro Asn Asp Asp Tyr Ala Ala Leu Val Arg
    130                 135                 140

Arg Val Glu Ile Glu Asn Ile Gly Gly Lys Glu Ile Glu Leu Glu Leu
145                 150                 155                 160

Met Asp Gly Leu Pro Glu Ile Leu Pro Tyr Gly Val Glu Asn Ser Gly
                165                 170                 175
```

-continued

Tyr Lys Glu Ile Gly Asn Leu Leu Arg Ser Trp Met Asp Val Tyr Asn
            180                 185                 190

Leu Glu Asn Gly Ile Pro Phe Tyr Lys Leu Arg Ser Ser Thr Asn Asp
            195                 200                 205

Ser Ala Gln Val Ser Glu Ile Thr Asn Gly His Phe Tyr Leu Ser Phe
    210                 215                 220

Thr Gly Glu Gly Glu Lys Val Ala Pro Ile Val Asp Phe Glu Leu Ile
225                 230                 235                 240

Phe Gly Gly Asn Thr Ser Leu Thr Tyr Pro Asp Arg Phe Ala Gly Leu
                245                 250                 255

Thr Leu Ser Glu Leu Ser Glu Leu Pro Gln Tyr Pro Val Asn Lys Val
            260                 265                 270

Pro Cys Gly Phe Ser Gly Val Ala Arg Arg Leu Ala Pro Gly Ser Ser
            275                 280                 285

Leu Thr Leu Asn Thr Leu Val Gly His Val Asn Asp Ile Asp Lys Ile
            290                 295                 300

Asn Lys Lys Ala Glu His Leu Cys Arg Asp Glu Tyr Ile Leu Ser Lys
305                 310                 315                 320

Ser Gln Glu Ala Ala Gly Leu Thr Glu Glu Leu Thr Glu Asp Ile Ala
                325                 330                 335

Thr His Thr Ser Ser Ala Val Phe Asp Ala Tyr Cys Arg Gln Ser Tyr
            340                 345                 350

Leu Asp Asn Phe Leu Arg Gly Gly Tyr Pro Phe Ile Phe Asp Asn Gly
            355                 360                 365

Gly Asp Gly Phe Val Val His Leu Tyr Ser Arg Lys His Gly Asp Leu
370                 375                 380

Glu Arg Asp Tyr Asn Phe Phe Ser Leu Ala Pro Glu Tyr Tyr Ser Gln
385                 390                 395                 400

Gly Asn Gly Asn Phe Arg Asp Met Asn Gln Asn Arg Arg Asn Asp Val
                405                 410                 415

Phe Phe Asn Pro Lys Val Gly Ser Phe Asn Ile Lys Met Phe Tyr Ser
            420                 425                 430

Leu Ile Gln Ala Asp Gly Tyr Asn Pro Leu Ser Val Gln Gly Thr Thr
            435                 440                 445

Phe Glu Val Lys Ser Asp Ser Arg Ala Lys Ala Ala Glu Trp Ile Gly
            450                 455                 460

Glu Ala Ala Ala Asp His Gln Ala Glu Leu Val Lys Leu Cys Asn Ser
465                 470                 475                 480

Arg Phe Thr Pro Gly Ser Leu Ile Asn Tyr Ile Ala Asp His Asn Val
                485                 490                 495

Thr Leu Lys Val Ser Glu Gln Glu Phe Leu Ser Gly Leu Leu Ala Leu
            500                 505                 510

Ser Gln Gln Asn Ile Glu Ala Ala Phe Gly Glu Gly Phe Trp Ser Asp
            515                 520                 525

His Trp Thr Tyr Asn Leu Asp Leu Val Val Gly Tyr Leu Asp Ile Phe
            530                 535                 540

Pro Asp Lys Lys Gln Glu Leu Leu Phe Gly Asp Asn Thr Tyr Ala Phe
545                 550                 555                 560

Tyr Asp Ser Pro Ala Tyr Val Leu Pro Arg Ser Glu Lys Tyr Val Ile
                565                 570                 575

Ser Asp Gly Lys Ala Arg Gln Tyr Gly Ala Leu Leu Glu Asp Glu Glu
            580                 585                 590

-continued

```
Lys Leu His Lys Leu Lys Trp Lys Ala Gly Asp Thr His Trp Leu Arg
            595                 600                 605

Ala Glu Gly Gly Gln Gly Ala Ile Tyr His Thr Asn Leu Phe Val Lys
        610                 615                 620

Met Leu Ser Leu Ala Leu Asn Lys Phe Ala Thr Leu Asp Pro Tyr Gly
625                 630                 635                 640

Met Gly Val Glu Met Glu Gly Asn Lys Pro Gly Trp Asn Asp Ala Met
                645                 650                 655

Asn Gly Leu Pro Gly Leu Phe Gly Ser Gly Met Ser Glu Thr Phe Glu
            660                 665                 670

Leu Lys Arg Thr Val Val Phe Leu Leu Asp Val Leu Asn Gly Ala Glu
        675                 680                 685

Asn Val Gln Gly Ala Val Lys Leu Pro Glu Glu Ile Ala Glu Leu Leu
690                 695                 700

Glu Ala Val Tyr His Ala Val Thr Ala Val Leu Ala Gly Asp Val Glu
705                 710                 715                 720

Gln Phe Asn Tyr Trp Asp Thr Val Ala Ser Ala Arg Glu Ala Tyr Arg
            725                 730                 735

Ala Ser Ile Arg Phe Gly Ile Thr Gly Val Glu Ser Ala Val Thr Leu
        740                 745                 750

Glu His Ile Arg Glu Ala Leu Ser Lys Phe Leu Val Lys Ile Asp Glu
    755                 760                 765

Gly Ile Asn Lys Ala Val Glu Met Gly Asn Gly Leu Thr Pro Thr Tyr
770                 775                 780

Phe Arg Phe Glu Ala Glu Lys Phe His Gln Val Thr Asp Ala Glu Gly
785                 790                 795                 800

Gln Pro Val Ile Ser Gly Tyr Gly Leu Pro Lys Ala Val Val Glu Glu
            805                 810                 815

Phe Lys Ala Tyr Ala Leu Pro Tyr Phe Leu Glu Gly Pro Thr Arg Trp
        820                 825                 830

Leu Lys Thr Met Lys Asn Pro Val Gln Ala Lys Glu Ile Tyr Asn Leu
    835                 840                 845

Ile Lys Gln Thr Glu Leu Tyr Asp Arg Ala Thr Ser Met Tyr Gln Thr
850                 855                 860

Ser Val Ser Leu Glu Gly Glu Ser His Glu Ile Gly Arg Met Arg Ala
865                 870                 875                 880

Phe Thr Pro Gly Trp Leu Glu Arg Glu Ser Asn Phe Leu His Met Ser
            885                 890                 895

Tyr Lys Tyr Leu Leu Glu Leu Leu Lys Gly Gly Leu Tyr Glu Glu Phe
        900                 905                 910

Tyr Gly Glu Leu Lys Thr Ser Leu Val Pro Phe Leu Asp Pro Ala Val
    915                 920                 925

Tyr Gly Arg Ser Thr Leu Glu Asn Ser Ser Phe Ile Ala Thr Gly Gly
    930                 935                 940

Asn Pro Asp Pro Asn Asn His Gly Arg Gly Phe Val Ala Arg Leu Ser
945                 950                 955                 960

Gly Ser Thr Ala Glu Phe Leu Ser Met Trp Arg Thr Met Ala Gly
            965                 970                 975

Ser His Val Phe Arg Leu Glu Asp Gly Ala Leu Thr Leu Ser Leu Asp
        980                 985                 990

Pro Val Leu Pro Gly Trp Leu Phe Asp Glu Glu Gly Asn Leu Ser Phe
    995                 1000                1005
```

```
Thr Phe Leu Gly Asn Thr Glu Val Ile Tyr Ser Asn Pro Lys Arg
    1010                1015                1020

Glu Asn Thr Phe Gly Glu Lys Lys Val Ser Ile Gln Ser Leu Met
        1025                1030                1035

Leu Val Tyr Arg Asn Gly Thr Met Thr Lys Ile Ser Gly Ala Phe
    1040                1045                1050

Val Arg Gly Glu Glu Ala Glu Ala Leu Arg Arg Gly Glu Ile Ala
    1055                1060                1065

Gln Ile Gln Ala Val Leu Ala Leu Glu His His His His His His
    1070                1075                1080

<210> SEQ ID NO 19
<211> LENGTH: 3240
<212> TYPE: DNA
<213> ORGANISM: Artificial sequence
<220> FEATURE:
<223> OTHER INFORMATION: CauGp1 codon-optimized and w/ additional
      C-terminal residues including 6x-His tag

<400> SEQUENCE: 19
atgtctaaat tttattttga tgaaaagaac cgctttgtta tagagaattt taatgcatct      60
aaaccgtttg cgtctttttct tccgggcatt gcaggcaaaa aaggcattcc tatgtggatc    120
ttttatgtta atagaggaca atgcattagc agctttggca tcaaaaacaa agataatccg    180
atcatggaat ttttccctgc atataagtgc tatcaaaatg ttcaatcagt tggctttcgc    240
acgtttatca agtttacaga tgaacaaaat atctatgaac cgtttctgta tcctcgcaat    300
aacaaagtta atcaaaaaat gtatatcggc atgaacgaac tggaaattga ggaagttaat    360
acggaaaatg ccttcaaat taatgttctg tattttatgc tgcctcaaga aaaaattgca    420
gcactggttc gcaaagttac gatcaaaaat atctctaaca ataagaaatc acttgaaatc    480
cttgatggca tgccggttgt tcttccgtat ggcatctcag atggcggcct taaacaagtt    540
ggcaatacac ttaaagcatg gatggaagtt tataatcatg aaggggggcat cccgatcttt    600 cgcatgcgct cttctagcga agattcagtt aatgttacgg agttcaaaga aggcaatttt    660
tatctgagct ttaaaaatgt taaaggcaaa aaagatctga tcaatccgat tgttgatatt    720
gatctggttt ttggcatgaa tacgtcactg agctatccgg atgtattta aatttttccg    780 ctgagcgaaa tcctggatcg caaacaaatt acgtctaaca agattccgtg ctcattttca    840
gcagttagcc ttgatgttaa tgctggcgaa gcactggaca tctatacgat catcggccat    900
gcaccggaaa tctcagttct tgaaagctac aaagaaatct ttatggatga aaattatatt    960
aataacaagt atctggaagg caaaaagatc gttgaaagac tgacggatga tatatatacg   1020
aaaacgagct ctaaactgtt tgatgaatat tgccgccaaa gctacttaga taatatcctt   1080
cgcgggggct atccgctgat cctgaaaaac ggggataaac cgctggttta ttatatgtat   1140
tcacgcaaac atggagatct ggaacgcgat tataattatt ttagcctgga accggaaatt   1200
tattctagcg gcaatggcaa ttatagagac ataaatcaaa atagacgcaa tgatgtattc   1260
tttaatccgg aagttaaaag ctataatatt aaaatcttta tgaatctgat ccaaagcgat   1320
ggctataatc ctctggttat caatggcgtt aaatatcgca tcaaagcaaa ttcactggat   1380
tttattgatg aacttgcaga agatacagat aaactgaaag aaatcctgtc taatccgttt   1440
acaccgggca gacttattac tttcattgag caacgcaata tcaaactgaa agttagccaa   1500
gaagaatttc tgacgaaaat catggaaaat gcagaagaag aaattgatgc agttcatggc   1560
gaaggctttt ggacggatca ttggacgtat aatttggatc ttatagaaaa ttacttggaa   1620
```

```
gtttatccgg ataaaaaacg cgatctgctg tttaatgagt atgattatac gtattttgat   1680
aattctaaag ttgttcttcc tagagaaaaa cgctatgttc tgtctaatgg caaagttcgc   1740
caatataata gcatcgttga agataaagat aagaagaaac tgatagaatc tcgcaaaacg   1800
tataagaata tcatgagagc aaataagggc gttggcgaaa tctatacgac gaatctgatt   1860
gttaaactgc tgaatcttgc agcagttaaa tttgcaacga tagatcctgc aggcatgggc   1920
atagagatgg aagcaggcaa accgggctgg tatgatgcac tgaatggcct gccgggactg   1980
tttggctcta gcgttgcaga agcatttgaa ctggttcgcc tgtttaattt tatccttgat   2040
gttctgaaag aatatccgga tgaagaaatc aaaatcccga ttgaggttat gcaactgata   2100
gagaatgagg ttaaatatgt tcaaagatat aacgaatcta atatggataa caaggattat   2160 gattttggt  ctatcatgtc agatcttcgc gaaaaatata gagaagatgt aaatttggc    2220 tttcaaggca agaagttag  cgttcgctca gcagaactga ttgataaaat caagaactg    2280 aaagataaac ttcaactggg actggataaa gcaatcatca acaatgatgg ccttatgccg   2340 acatatttt  attatgatgt tgaagaatat gaaatcatca aaggcataga caaagatgtt   2400
gatgatgaaa atcaagaaaa atatattaga gcacttaagt ttaaacaaaa caagatgcct   2460
ctgtttctgg aaggcatcgt tcgcggcttt aaaatctata tgataaaga  ttttctgcgc   2520 gatgtttaca acgcgttaa  aaattcagat ctgtttgata aaaaacttaa aatgtacaaa   2580
gttaatgcaa gcctgaacaa ggaaacgata gagatcggcc gcgcacgcgc gtttacaccg   2640
ggctggttag aaaacgaaag catttggtta cacatggaat acaaatatat gctggaactg   2700
ctgaaatcag gactgtataa ggaatattat gatgatttta aaaatgttct gattccgttt   2760
atggatgcaa gcgtttatgg ccgctcacct cttgaaaatt ctagctttat tgcaagctca   2820
gcaaatgttg atgaaagcat ccacggcacg ggctttgttg cacgcctgtc cggtgcaaca   2880
gcagaatttc tgtctatgtg gagacttatg tttgttggca aaaaaccgtt taaaatcatc   2940
aatggcaaac ttacacttag ctttaatccg gttctgccgg aatggctgtt tgatgaagaa   3000
aacaaggtta gctttaattt tctgggacgc tgccgcgtta cgtattataa tccgtcacgc   3060
aaaaatacgt atgagatgga tattacgaaa caaaaaatca tcatctatct tccgagcggc   3120
aatacgatag agtttcttga taattttatt gaagaagaat atgcaacact gattcgcgaa   3180
ggcaaaatca atcgcattga catctatctt aaactcgagc accaccaca  ccaccactga   3240
```

<210> SEQ ID NO 20  
<211> LENGTH: 1079  
<212> TYPE: PRT  
<213> ORGANISM: Artificial sequence  
<220> FEATURE:  
<223> OTHER INFORMATION: CauGp1 w/ additional C-terminal residues including 6x-His tag
<400> SEQUENCE: 20

Met Ser Lys Phe Tyr Phe Asp Glu Lys Asn Arg Phe Val Ile Glu Asn
1               5                   10                  15

Phe Asn Ala Ser Lys Pro Phe Ala Ser Phe Leu Pro Gly Ile Ala Gly
            20                  25                  30

Lys Lys Gly Ile Pro Met Trp Ile Phe Tyr Val Asn Arg Gly Gln Cys
        35                  40                  45

Ile Ser Ser Phe Gly Ile Lys Asn Lys Asp Asn Pro Ile Met Glu Phe
    50                  55                  60

Phe Pro Ala Tyr Lys Cys Tyr Gln Asn Val Gln Ser Val Gly Phe Arg
65                  70                  75                  80

-continued

Thr Phe Ile Lys Phe Thr Asp Glu Gln Asn Ile Tyr Glu Pro Phe Leu
            85                  90                  95

Tyr Pro Arg Asn Asn Lys Val Asn Gln Lys Met Tyr Ile Gly Met Asn
        100                 105                 110

Glu Leu Glu Ile Glu Glu Val Asn Thr Glu Asn Gly Leu Gln Ile Asn
    115                 120                 125

Val Leu Tyr Phe Met Leu Pro Gln Glu Lys Ile Ala Ala Leu Val Arg
130                 135                 140

Lys Val Thr Ile Lys Asn Ile Ser Asn Asn Lys Lys Ser Leu Glu Ile
145                 150                 155                 160

Leu Asp Gly Met Pro Val Val Leu Pro Tyr Gly Ile Ser Asp Gly Gly
                165                 170                 175

Leu Lys Gln Val Gly Asn Thr Leu Lys Ala Trp Met Glu Val Tyr Asn
            180                 185                 190

His Glu Gly Gly Ile Pro Ile Phe Arg Met Arg Ser Ser Glu Asp
        195                 200                 205

Ser Val Asn Val Thr Glu Phe Lys Glu Gly Asn Phe Tyr Leu Ser Phe
    210                 215                 220

Lys Asn Val Lys Gly Lys Lys Asp Leu Ile Asn Pro Ile Val Asp Ile
225                 230                 235                 240

Asp Leu Val Phe Gly Met Asn Thr Ser Leu Ser Tyr Pro Asp Val Phe
                245                 250                 255

Tyr Asn Phe Pro Leu Ser Glu Ile Leu Asp Arg Lys Gln Ile Thr Ser
            260                 265                 270

Asn Lys Ile Pro Cys Ser Phe Ser Ala Val Ser Leu Asp Val Asn Ala
        275                 280                 285

Gly Glu Ala Leu Asp Ile Tyr Thr Ile Ile Gly His Ala Pro Glu Ile
    290                 295                 300

Ser Val Leu Glu Ser Tyr Lys Glu Ile Phe Met Asp Glu Asn Tyr Ile
305                 310                 315                 320

Asn Asn Lys Tyr Leu Glu Gly Lys Lys Ile Val Glu Arg Leu Thr Asp
                325                 330                 335

Asp Ile Tyr Thr Lys Thr Ser Ser Lys Leu Phe Asp Glu Tyr Cys Arg
            340                 345                 350

Gln Ser Tyr Leu Asp Asn Ile Leu Arg Gly Gly Tyr Pro Leu Ile Leu
        355                 360                 365

Lys Asn Gly Asp Lys Pro Leu Val Tyr Tyr Met Tyr Ser Arg Lys His
    370                 375                 380

Gly Asp Leu Glu Arg Asp Tyr Asn Tyr Phe Ser Leu Glu Pro Glu Tyr
385                 390                 395                 400

Tyr Ser Ser Gly Asn Gly Asn Tyr Arg Asp Ile Asn Gln Asn Arg Arg
                405                 410                 415

Asn Asp Val Phe Phe Asn Pro Glu Val Lys Ser Tyr Asn Ile Lys Ile
            420                 425                 430

Phe Met Asn Leu Ile Gln Ser Asp Gly Tyr Asn Pro Leu Val Ile Asn
        435                 440                 445

Gly Val Lys Tyr Arg Ile Lys Ala Asn Ser Leu Asp Phe Ile Asp Glu
    450                 455                 460

Leu Ala Glu Asp Thr Asp Lys Leu Lys Glu Ile Leu Ser Asn Pro Phe
465                 470                 475                 480

Thr Pro Gly Arg Leu Ile Thr Phe Ile Glu Gln Arg Asn Ile Lys Leu
                485                 490                 495

```
Lys Val Ser Gln Glu Glu Phe Leu Thr Lys Ile Met Glu Asn Ala Glu
                500                 505                 510

Glu Glu Ile Asp Ala Val His Gly Gly Phe Trp Thr Asp His Trp
            515                 520                 525

Thr Tyr Asn Leu Asp Leu Ile Glu Asn Tyr Leu Glu Val Tyr Pro Asp
        530                 535                 540

Lys Lys Arg Asp Leu Leu Phe Asn Glu Tyr Asp Tyr Thr Tyr Phe Asp
545                 550                 555                 560

Asn Ser Lys Val Val Leu Pro Arg Glu Lys Arg Tyr Val Leu Ser Asn
                565                 570                 575

Gly Lys Val Arg Gln Tyr Asn Ser Ile Val Glu Asp Lys Asp Lys Lys
            580                 585                 590

Lys Leu Ile Glu Ser Arg Lys Thr Tyr Lys Asn Ile Met Arg Ala Asn
        595                 600                 605

Lys Gly Val Gly Glu Ile Tyr Thr Thr Asn Leu Ile Val Lys Leu Leu
        610                 615                 620

Asn Leu Ala Ala Val Lys Phe Ala Thr Ile Asp Pro Ala Gly Met Gly
625                 630                 635                 640

Ile Glu Met Glu Ala Gly Lys Pro Gly Trp Tyr Asp Ala Leu Asn Gly
                645                 650                 655

Leu Pro Gly Leu Phe Gly Ser Ser Val Ala Glu Ala Phe Glu Leu Val
            660                 665                 670

Arg Leu Phe Asn Phe Ile Leu Asp Val Leu Lys Glu Tyr Pro Asp Glu
        675                 680                 685

Glu Ile Lys Ile Pro Ile Glu Val Met Gln Leu Ile Glu Asn Glu Val
        690                 695                 700

Lys Tyr Val Gln Arg Tyr Asn Glu Ser Asn Met Asp Asn Lys Asp Tyr
705                 710                 715                 720

Asp Phe Trp Ser Ile Met Ser Asp Leu Arg Glu Lys Tyr Arg Glu Asp
                725                 730                 735

Val Lys Phe Gly Phe Gln Gly Lys Glu Val Ser Val Arg Ser Ala Glu
            740                 745                 750

Leu Ile Asp Lys Ile Lys Glu Leu Lys Asp Lys Leu Gln Leu Gly Leu
        755                 760                 765

Asp Lys Ala Ile Ile Asn Asn Asp Gly Leu Met Pro Thr Tyr Phe Tyr
770                 775                 780

Tyr Asp Val Glu Glu Tyr Glu Ile Ile Lys Gly Ile Asp Lys Asp Val
785                 790                 795                 800

Asp Asp Glu Asn Gln Glu Lys Tyr Ile Arg Ala Leu Lys Phe Lys Gln
                805                 810                 815

Asn Lys Met Pro Leu Phe Leu Glu Gly Ile Val Arg Gly Phe Lys Ile
            820                 825                 830

Tyr Asn Asp Lys Asp Phe Leu Arg Asp Val Tyr Lys Arg Val Lys Asn
        835                 840                 845

Ser Asp Leu Phe Asp Lys Lys Leu Lys Met Tyr Lys Val Asn Ala Ser
        850                 855                 860

Leu Asn Lys Glu Thr Ile Glu Ile Gly Arg Ala Arg Ala Phe Thr Pro
865                 870                 875                 880

Gly Trp Leu Glu Asn Glu Ser Ile Trp Leu His Met Glu Tyr Lys Tyr
                885                 890                 895

Met Leu Glu Leu Leu Lys Ser Gly Leu Tyr Lys Glu Tyr Tyr Asp Asp
            900                 905                 910
```

```
Phe Lys Asn Val Leu Ile Pro Phe Met Asp Ala Ser Val Tyr Gly Arg
            915                 920                 925

Ser Pro Leu Glu Asn Ser Ser Phe Ile Ala Ser Ser Ala Asn Val Asp
        930                 935                 940

Glu Ser Ile His Gly Thr Gly Phe Val Ala Arg Leu Ser Gly Ala Thr
945                 950                 955                 960

Ala Glu Phe Leu Ser Met Trp Arg Leu Met Phe Val Gly Lys Lys Pro
                965                 970                 975

Phe Lys Ile Ile Asn Gly Lys Leu Thr Leu Ser Phe Asn Pro Val Leu
            980                 985                 990

Pro Glu Trp Leu Phe Asp Glu Glu Asn Lys Val Ser Phe Asn Phe Leu
        995                 1000                1005

Gly Arg Cys Arg Val Thr Tyr  Tyr Asn Pro Ser Arg  Lys Asn Thr
    1010                1015                1020

Tyr Glu  Met Asp Ile Thr Lys  Gln Lys Ile Ile Ile  Tyr Leu Pro
    1025                1030                1035

Ser Gly  Asn Thr Ile Glu Phe  Leu Asp Asn Phe Ile  Glu Glu Glu
    1040                1045                1050

Tyr Ala  Thr Leu Ile Arg Glu  Gly Lys Ile Asn Arg  Ile Asp Ile
    1055                1060                1065

Tyr Leu  Lys Leu Glu His  His  His His His His
    1070                1075
```

<210> SEQ ID NO 21
<211> LENGTH: 3207
<212> TYPE: DNA
<213> ORGANISM: Artificial sequence
<220> FEATURE:
<223> OTHER INFORMATION: OgrGp1 codon-optimized and w/ additional
      C-terminal residues including 6x-His tag

<400> SEQUENCE: 21

| | |
|---|---|
| atgtcagttg aatatagctt taatgataaa aatcagttca tgattgaaga ttatgataaa | 60 |
| gcaaaaacgt ttgcttcttt tcttccgggc atcgcaggcg ttgatggcat cccgatgtgg | 120 |
| tcattttatg ttaatagagg acaaggcatg ggcagctttg gcgttaaaga taaagataat | 180 |
| acgatcatgg agttctttcc tgcaaatctt atgtataaga atatagaact tcaaggcttt | 240 |
| cgcacgttta tcaaatatca aggcaaaatc catgaaatct ttagctctat gtcacaagat | 300 |
| caagttgaac gcaaaatggc aatagaaaag aacattctga gcatagaaga gttaacaaa | 360 |
| acacttaatc ttaaaatcaa agttacgtat tttacgatgc ctaaagaaga ttttgcagca | 420 |
| attgttcgca agttgaaat tgttgatctg aacaacaacg aagttgaaat tgaggttctg | 480 |
| gatggcctga cacaaatcct gccgtatggc gtttctaata gcgcatatca atctatggca | 540 |
| aatctgagcc gcgcatggtt tgatgtttat aacctggaaa acaatattcc gtattataag | 600 |
| gttcgcgcaa caacgagcga ttcttcagaa gttggagaag ttacgaaagg caatttttat | 660 |
| cttgcatttg catctaacaa cgaaggactg ctgccgacga tctttgatgt tgatgttatc | 720 |
| tttggcacga atacgagcct gacgtatcct gcaggctggg attgctcagt tgaagaactt | 780 |
| aacaagcgca tccaaattcc tcaaaataag gtttcaggtg gctttacagc agttaaagca | 840 |
| agcatcaaag ataagttcac actgtgctct attatcggcc atattgcatc accggaactg | 900 |
| atcaatgcta aaaacataa tttttacgatg gaatatatta aaacaaaga atttgaagca | 960 |
| cgcaaactgg ttgattcact tgttgaagat acgaaaacga aaacgtctaa tgcactgttt | 1020 |
| gataaaatata ttgactcttg ctatctggat aatatcctgc gcggcggcta ccgcttgca | 1080 |

-continued

```
atagaagccg gagataaaaa tcatatctat catgtatttt ctcgcaaaca tggcgataca    1140
gaacgcgaat ataatttctt tagcctggaa ccggcatatt atagccaagg caatggcaat    1200
tttcgcgatg ttaatcaaaa tagacgctca gatattctgt ttaatcctaa agttaaaaat    1260
tttaatgtta aacaattcat gtctctgatc caagcagatg gctataatcc gctgtcagtt    1320
aaaggctcta cgttcacatt tgataatagc tatatggatg aagttcttaa ttatttggaa    1380
aaaggcaaag aaggctttaa atctattctg gaagaaaatt ttacaccggg agacatcatc    1440
acgtatctgt gcgaaaacaa tatagacctg agcattagca atgatgaata tctgaatctg    1500
atcctgtcta aatctacaca aaattatgaa gcaaattttg gcgaaggcta ttggacggat    1560
cattggacgt ataatatgga tcttgttgat acgtatctga atatctatcc ggatatgctg    1620
gaagattttc tgtttgaaga gatggattac aagtattttg attcaccggt taaagttctt    1680
aaacgcgaag aaaaatatat catcaaaaat ggcaaagttc gccaatatgg ctctatcttt    1740
gaagatgaga gaaatgcca tgatctgggc atagatatta aaggaacgaa ttggctgaaa    1800
acggaaggtg gcaaaggcaa agtttatgaa acgaatctgt atgcaaaact gattagcctt    1860
gcacttaaca gtttgttac gatggacccg tatggcatgg gcatagagat ggagggcgaa    1920
aaaccgggct ggaatgatgc gatgaatggc ctgccgggcc tgtttggctc aggacttaac    1980
gagacagcag aactgaaacg catcgttgag tttattgttg aagttagctc taagtttaac    2040
aaggatttta tgtttccggt tgaaatgacg gaactgctta tgcatacaga aaaaacactt    2100
aatcgctatc ttaacgaaga atttgaagaa tttgaatatt ggaataagat tgcaacactt    2160
cgcgaagaat atagagaaaa aatctattat ggcatcgctg gagaagaagt taaactgagc    2220
tctaaagaaa tccttcaagc attcacgaaa ttcaatcata aaatcaataa gggactggaa    2280
aaagcactgg aatatggcaa tggcatctat ccgacgtatt ttacgtatga agcaaaagaa    2340
tatgaaatca ttgagggcaa agttaatccg gttaatggct atcaaaatgt taagttaat    2400 gcatttgaat gcaaaccgat gccgctgttt ctggaaggac cggcacgcac acttaaatct    2460
atgaaagaca taaataagtc tcgcacactg tacaaggcaa tcaaagaaag cgatatatat    2520
gataaaaaac ttaaaatgta caaaacgagc gttccgttag atgaactgtc taatgagatc    2580
ggccgcgcac gcgcgtttac agcaggctgg ttagaacgcg aagcagtttt tcttcacatg    2640
gaatacaagt atctgcttgc actgctgaaa gcaggactgt ataacgaata ttatgaagat    2700
atgcaaacaa cgctgacagc atttctggac cctcaagttt atggccgctc tacattagaa    2760
aattctagct ttattgcaag cagcgttaat ccggatgatg cagttcatgg ccgcggcttt    2820
gttgcacgcc ttagcggctc aacagcagaa atgctgtcta tttggtttat catgatggca    2880
ggcgaaaaag ttttttacgta tgaaaatgat aaacttcaac tggaactgag cccgatcctt    2940
cctgcatggc tgtttgataa cgaaggcaaa gttagcttta cgtttctggg caaaacggaa    3000
gttacgtatc ataatcctaa aaaacttaat acgtatggag aaaacaaagc agttgcagat    3060
aaaatcatca ttacggttaa cgaaaacgaa aaaattgaac ttaaaggcaa tattattacg    3120
gaagattatg caaaagcaat tagagatggc aaaaatcaaca aagttgacat atattttaaa    3180
ctcgagcacc accaccacca ccactga                                         3207
```

<210> SEQ ID NO 22
<211> LENGTH: 1068
<212> TYPE: PRT
<213> ORGANISM: Artificial sequence
<220> FEATURE:
<223> OTHER INFORMATION: OgrGp1 w/ additional C-terminal residues
      including 6x-His tag

<400> SEQUENCE: 22

```
Met Ser Val Glu Tyr Ser Phe Asn Asp Lys Asn Gln Phe Met Ile Glu
1               5                   10                  15

Asp Tyr Asp Lys Ala Lys Thr Phe Ala Ser Phe Leu Pro Gly Ile Ala
            20                  25                  30

Gly Val Asp Gly Ile Pro Met Trp Ser Phe Tyr Val Asn Arg Gly Gln
        35                  40                  45

Gly Met Gly Ser Phe Gly Val Lys Asp Lys Asp Asn Thr Ile Met Glu
50                  55                  60

Phe Phe Pro Ala Asn Leu Met Tyr Lys Asn Ile Glu Leu Gln Gly Phe
65                  70                  75                  80

Arg Thr Phe Ile Lys Tyr Gln Gly Lys Ile His Glu Ile Phe Ser Ser
                85                  90                  95

Met Ser Gln Asp Gln Val Glu Arg Lys Met Ala Ile Glu Lys Asn Ile
            100                 105                 110

Leu Ser Ile Glu Glu Val Asn Lys Thr Leu Asn Leu Lys Ile Lys Val
        115                 120                 125

Thr Tyr Phe Thr Met Pro Lys Glu Asp Phe Ala Ala Ile Val Arg Lys
130                 135                 140

Val Glu Ile Val Asp Leu Asn Asn Asn Glu Val Glu Ile Glu Val Leu
145                 150                 155                 160

Asp Gly Leu Thr Gln Ile Leu Pro Tyr Gly Val Ser Asn Ser Ala Tyr
                165                 170                 175

Gln Ser Met Ala Asn Leu Ser Arg Ala Trp Phe Asp Val Tyr Asn Leu
            180                 185                 190

Glu Asn Asn Ile Pro Tyr Tyr Lys Val Arg Ala Thr Thr Ser Asp Ser
        195                 200                 205

Ser Glu Val Gly Glu Val Thr Lys Gly Asn Phe Tyr Leu Ala Phe Ala
210                 215                 220

Ser Asn Asn Glu Gly Leu Leu Pro Thr Ile Phe Asp Val Asp Val Ile
225                 230                 235                 240

Phe Gly Thr Asn Thr Ser Leu Thr Tyr Pro Ala Gly Trp Asp Cys Ser
                245                 250                 255

Val Glu Glu Leu Asn Lys Arg Ile Gln Ile Pro Gln Asn Lys Val Ser
            260                 265                 270

Gly Gly Phe Thr Ala Val Lys Ala Ser Ile Lys Asp Lys Phe Thr Leu
        275                 280                 285

Cys Ser Ile Ile Gly His Ile Ala Ser Pro Glu Leu Ile Asn Ala Lys
290                 295                 300

Lys His Asn Phe Thr Met Glu Tyr Ile Lys Asn Lys Glu Phe Glu Ala
305                 310                 315                 320

Arg Lys Leu Val Asp Ser Leu Val Glu Asp Thr Lys Thr Lys Thr Ser
                325                 330                 335

Asn Ala Leu Phe Asp Lys Tyr Ile Asp Ser Cys Tyr Leu Asp Asn Ile
            340                 345                 350

Leu Arg Gly Gly Tyr Pro Leu Ala Ile Glu Ala Gly Asp Lys Asn His
        355                 360                 365

Ile Tyr His Val Phe Ser Arg Lys His Gly Asp Thr Glu Arg Glu Tyr
370                 375                 380
```

Asn Phe Phe Ser Leu Glu Pro Ala Tyr Tyr Ser Gln Gly Asn Gly Asn
385                 390                 395                 400

Phe Arg Asp Val Asn Gln Asn Arg Arg Ser Asp Ile Leu Phe Asn Pro
            405                 410                 415

Lys Val Lys Asn Phe Asn Val Lys Gln Phe Met Ser Leu Ile Gln Ala
        420                 425                 430

Asp Gly Tyr Asn Pro Leu Ser Val Lys Gly Ser Thr Phe Thr Phe Asp
    435                 440                 445

Asn Ser Tyr Met Asp Glu Val Leu Asn Tyr Leu Glu Lys Gly Lys Glu
    450                 455                 460

Gly Phe Lys Ser Ile Leu Glu Glu Asn Phe Thr Pro Gly Asp Ile Ile
465                 470                 475                 480

Thr Tyr Leu Cys Glu Asn Asn Ile Asp Leu Ser Ile Ser Asn Asp Glu
            485                 490                 495

Tyr Leu Asn Leu Ile Leu Ser Lys Ser Thr Gln Asn Tyr Glu Ala Asn
            500                 505                 510

Phe Gly Glu Gly Tyr Trp Thr Asp His Trp Thr Tyr Asn Met Asp Leu
        515                 520                 525

Val Asp Thr Tyr Leu Asn Ile Tyr Pro Asp Met Leu Glu Asp Phe Leu
    530                 535                 540

Phe Glu Glu Met Asp Tyr Lys Tyr Phe Asp Ser Pro Val Lys Val Leu
545                 550                 555                 560

Lys Arg Glu Glu Lys Tyr Ile Ile Lys Asn Gly Lys Val Arg Gln Tyr
            565                 570                 575

Gly Ser Ile Phe Glu Asp Glu Lys Lys Cys His Asp Leu Gly Ile Asp
        580                 585                 590

Ile Lys Gly Thr Asn Trp Leu Lys Thr Glu Gly Gly Lys Gly Lys Val
    595                 600                 605

Tyr Glu Thr Asn Leu Tyr Ala Lys Leu Ile Ser Leu Ala Leu Asn Lys
610                 615                 620

Phe Val Thr Met Asp Pro Tyr Gly Met Gly Ile Glu Met Glu Gly Glu
625                 630                 635                 640

Lys Pro Gly Trp Asn Asp Ala Met Asn Gly Leu Pro Gly Leu Phe Gly
            645                 650                 655

Ser Gly Leu Asn Glu Thr Ala Glu Leu Lys Arg Ile Val Glu Phe Ile
        660                 665                 670

Val Glu Val Ser Ser Lys Phe Asn Lys Asp Phe Met Phe Pro Val Glu
    675                 680                 685

Met Thr Glu Leu Leu Met His Thr Glu Lys Thr Leu Asn Arg Tyr Leu
690                 695                 700

Asn Glu Glu Phe Glu Glu Phe Glu Tyr Trp Asn Lys Ile Ala Thr Leu
705                 710                 715                 720

Arg Glu Glu Tyr Arg Glu Lys Ile Tyr Tyr Gly Ile Ala Gly Glu Glu
            725                 730                 735

Val Lys Leu Ser Ser Lys Glu Ile Leu Gln Ala Phe Thr Lys Phe Asn
        740                 745                 750

His Lys Ile Asn Lys Gly Leu Glu Lys Ala Leu Glu Tyr Gly Asn Gly
    755                 760                 765

Ile Tyr Pro Thr Tyr Phe Thr Tyr Glu Ala Lys Glu Tyr Glu Ile Ile
    770                 775                 780

Glu Gly Lys Val Asn Pro Val Asn Gly Tyr Gln Asn Val Lys Val Asn
785                 790                 795                 800

```
Ala Phe Glu Cys Lys Pro Met Pro Leu Phe Leu Glu Gly Pro Ala Arg
                805                 810                 815

Thr Leu Lys Ser Met Lys Asp Ile Asn Lys Ser Arg Thr Leu Tyr Lys
        820                 825                 830

Ala Ile Lys Glu Ser Asp Ile Tyr Asp Lys Lys Leu Lys Met Tyr Lys
        835                 840                 845

Thr Ser Val Pro Leu Asp Glu Leu Ser Asn Glu Ile Gly Arg Ala Arg
850                 855                 860

Ala Phe Thr Ala Gly Trp Leu Glu Arg Glu Ala Val Phe Leu His Met
865                 870                 875                 880

Glu Tyr Lys Tyr Leu Leu Ala Leu Leu Lys Ala Gly Leu Tyr Asn Glu
            885                 890                 895

Tyr Tyr Glu Asp Met Gln Thr Thr Leu Thr Ala Phe Leu Asp Pro Gln
            900                 905                 910

Val Tyr Gly Arg Ser Thr Leu Glu Asn Ser Ser Phe Ile Ala Ser Ser
            915                 920                 925

Val Asn Pro Asp Asp Ala Val His Gly Arg Gly Phe Val Ala Arg Leu
    930                 935                 940

Ser Gly Ser Thr Ala Glu Met Leu Ser Ile Trp Phe Ile Met Met Ala
945                 950                 955                 960

Gly Glu Lys Val Phe Thr Tyr Glu Asn Asp Lys Leu Gln Leu Glu Leu
                965                 970                 975

Ser Pro Ile Leu Pro Ala Trp Leu Phe Asp Asn Glu Gly Lys Val Ser
            980                 985                 990

Phe Thr Phe Leu Gly Lys Thr Glu  Val Thr Tyr His Asn  Pro Lys Lys
            995                 1000                 1005

Leu Asn  Thr Tyr Gly Glu Asn  Lys Ala Val Ala Asp  Lys Ile Ile
    1010                 1015                 1020

Ile Thr  Val Asn Glu Asn Glu  Lys Ile Glu Leu Lys  Gly Asn Ile
    1025                 1030                 1035

Ile Thr  Glu Asp Tyr Ala Lys  Ala Ile Arg Asp Gly  Lys Ile Asn
    1040                 1045                 1050

Lys Val  Asp Ile Tyr Phe Lys  Leu Glu His His His  His His His
    1055                 1060                 1065

<210> SEQ ID NO 23
<211> LENGTH: 3117
<212> TYPE: DNA
<213> ORGANISM: Artificial sequence
<220> FEATURE:
<223> OTHER INFORMATION: LphGp1 codon-optimized and w/ additional
      C-terminal residues including 6x-His tag

<400> SEQUENCE: 23
atgtttgata taagggacg ctttatcatt cgcaattatg caaagaaatc accgtttgca      60
tcttttcttc cgggcatcag cggcaaatat ggcatcccga tttggtgctt ttatgttaat     120
agaggacaag cagttacgag ctttggcgtt cttgataaag atcatagcat catggaattt     180
tatcctgcac atcaagcata tcaaatcacg aaaacgaatg ctttcgcac gtttcttaaa     240 atagatcata gctatacgga ggcattcacg gaagaagata gagaacatgc aatgtatatc     300
ggcatgaatg agcttgaact ggaagaaaaa atagagcaaa aaattagcgt taatgttacg     360
tattttacgc tgcctaacga agcactggga ggactggttc gcaaagttac ggttaaaaat     420
atagacacga cggaacatct tgttgaactg ctggatggaa tgccgagcct gattccgtat     480
ggcgttagcc ttaatagcat gaaagaaatg ggacaaacga cgaaagcatg gatgcaagtt     540
```

```
gaaaatctta gcgaacgcct gccgttcttc aaagttcgcg caagtatgga agattcagtt      600
gatgttcatg aagttatcgg cggccatttt agctttggca tagacggcaa aggattactt      660
ccggttctgg ttgatccgta cctggttttt ggctatgata cgtctctgac gaaagcaatc      720
ggctttaaag agggtgaact taattatttg cttcgcaaaa atcaagttgt tacgaataac      780
ttaccgtgct cattcttcgc aaaacaaaaa atcctgatgc cggaagaaga gttcacgatc      840
tatgaagtta tcggccaagc aaaatctatc gcaacggttc gcgaatttgc aacgtcatgc      900
gttagcgaag gctattttaa aagaagtat gaagaagcaa ttgcactgac agaagatctg       960
tgcaaaggca tagagacgaa aacagcatca ccggttttg atgcatattg caaacaaacg       1020
tacctagata atatcctgcg tggaggctat ccgattaaac tgggcaaaga taaaatcttt      1080
tatctttata gccgcaaaca tggagacatt gagcgcgatt ataatttctt tagcatgctg      1140
ccggaatatt attcacaagg caatgcaaat tatagagatg ttaatcaaaa tagacgctgc      1200
gatgttctgt ttagcccgtt tgttgaagat gaatgcatca aaatgtttta atctctgatc      1260
caaattgacg gctataatcc tcttgcagtt caaaaagcaa cgttttgcat cccgagcgaa      1320
aagatggaag aagcagtttc aatccttccg attaaagaaa aagttaatgg ctataatttc      1380
tttcaaaata gctttacacc gggcagcttt ctgggctttc tggaacaaca aggatgcacg      1440
gataagaaaa cacttgaaaa tacactgagc tcagttatgg aagtttcaga atcagaaatt      1500
gcagcctctt ttggcgaagg atattgggtt gatcattgga cgtataacct agatctggtt      1560
gaagcatttc tgtctatcta tccggaacgc gaagaagatc tgttttatca tgatataacg      1620
tatacatatt ttgaatcaat ggcaattgtt aacaaacgcc aaaatcgcta tgttgaaacg      1680
aaaaatggcc ttcgccaata taagtcactt gataaaggct ctaaaaaaga agttgcacat      1740
aaacaactgc gctgcgatta tggcaaaggc tcagtttatc aaacgagcct gctggaaaaa      1800
ctgctgctgc tgatctctat taaaattgca acacttgatc cggaaggcat gggcatagag      1860
atggaagcag gcaaaccggg ctggtatgat gcacttaatg gcctgccggg catctttggc      1920
agctctatgt gcgaaacgat tgagcttgaa cgcatgatta gctttgttct gtctattgtt      1980
aatcgctatc ctaataacgt tccggttgca cttgaaatta agaactgat ggaaaatctg       2040
tatgaagttt cacgccgcga aattacgagt atggaagcat gggatctgcg caacaattct      2100
aaagaaaatt atagagaaaa aacgaaactg gagttgaag gcacgaaaga agttctgatg       2160
gttgaagata ttcgcgcaat gctgacgacg tggtcatttc ttgttaaaaa aggcattgag      2220
aaagcagtta aactgggcaa aggcatttgc cctacgtatt tttattacaa ggcaaaagaa      2280
tatgaaaaga aggaagatgg catctttatt aaagaatttg aacttatgtc tatgccgtat      2340
tttcttgaag gacctgttca ttatcttaaa ctggaacaat ctcaagaaga aaagaagcgc      2400
ctgtatcaag cagttaaaga atctaatctg tatgatcgca aacttaaaat gtataaggtt      2460
aatgagtctc ttcataaagc gtcctttgaa gttggccgct ctacagcttt cacaccgggc      2520
tggttagaaa atgagtctat ttggttacac atggaatata agtattatct ggaactgctt      2580
aaatcaggac tgtatgaaga atattttgaa gattttaaaa atggcctgat tccgttctg       2640
gaagagaaaa agtatggccg ctcaatcctt gaaaatagct catttcttgc atctagcgca      2700
aatccggatg aaaaaattca tggcaaaggc tttgttgcac gcctgagcgg ctctacagca      2760
gaatttgttc acatgtggca aatcatgatg tttggccata atccgtttcg ctatgaacaa      2820
gaagaactgt atctgagcct ggaaccgatc cttccggaat atctgatcgg cgaagatggc      2880
gttatcaaag caacgtttct gggcaaaatt ccggtttgct atcaactgct taaaaagaaa      2940
```

-continued

```
gcacttcttc cgggacgcta caaagttgaa tcatatacac ttcaatatga agatggcgaa    3000
attaaacaaa tctcagaatc taaacttccg tgcaaagaat ctatggatgt tagagatggc    3060
cgcgttaatt caattagcgt ttctatctca ctcgagcacc accaccacca ccactga       3117
```

<210> SEQ ID NO 24
<211> LENGTH: 1038
<212> TYPE: PRT
<213> ORGANISM: Artificial sequence
<220> FEATURE:
<223> OTHER INFORMATION: LphGp1 w/ additional C-terminal residues including 6x-His tag

<400> SEQUENCE: 24

```
Met Phe Asp Asn Lys Gly Arg Phe Ile Ile Arg Asn Tyr Ala Lys Glu
1               5                   10                  15

Ser Pro Phe Ala Ser Phe Leu Pro Gly Ile Ser Gly Lys Tyr Gly Ile
            20                  25                  30

Pro Ile Trp Cys Phe Tyr Val Asn Arg Gly Gln Ala Val Thr Ser Phe
        35                  40                  45

Gly Val Leu Asp Lys Asp His Ser Ile Met Glu Phe Tyr Pro Ala His
    50                  55                  60

Gln Ala Tyr Gln Ile Thr Lys Thr Asn Gly Phe Arg Thr Phe Leu Lys
65                  70                  75                  80

Ile Asp His Ser Tyr Thr Glu Ala Phe Thr Glu Glu Asp Arg Glu His
                85                  90                  95

Ala Met Tyr Ile Gly Met Asn Glu Leu Glu Leu Glu Glu Lys Ile Glu
            100                 105                 110

Gln Lys Ile Ser Val Asn Val Thr Tyr Phe Thr Leu Pro Asn Glu Ala
        115                 120                 125

Leu Gly Gly Leu Val Arg Lys Val Thr Val Lys Asn Ile Asp Thr Thr
    130                 135                 140

Glu His Leu Val Glu Leu Leu Asp Gly Met Pro Ser Leu Ile Pro Tyr
145                 150                 155                 160

Gly Val Ser Leu Asn Ser Met Lys Glu Met Gly Gln Thr Thr Lys Ala
                165                 170                 175

Trp Met Gln Val Glu Asn Leu Ser Glu Arg Leu Pro Phe Phe Lys Val
            180                 185                 190

Arg Ala Ser Met Glu Asp Ser Val Asp Val His Glu Val Ile Gly Gly
        195                 200                 205

His Phe Ser Phe Gly Ile Asp Gly Lys Gly Leu Leu Pro Val Leu Val
    210                 215                 220

Asp Pro Tyr Leu Val Phe Gly Tyr Asp Thr Ser Leu Thr Lys Ala Ile
225                 230                 235                 240

Gly Phe Lys Glu Gly Glu Leu Asn Tyr Leu Leu Arg Lys Asn Gln Val
                245                 250                 255

Val Thr Asn Asn Leu Pro Cys Ser Phe Phe Ala Lys Gln Lys Ile Leu
            260                 265                 270

Met Pro Glu Glu Glu Phe Thr Ile Tyr Glu Val Ile Gly Gln Ala Lys
        275                 280                 285

Ser Ile Ala Thr Val Arg Glu Phe Ala Thr Ser Cys Val Ser Glu Gly
    290                 295                 300

Tyr Phe Lys Lys Lys Tyr Glu Glu Ala Ile Ala Leu Thr Glu Asp Leu
305                 310                 315                 320

Cys Lys Gly Ile Glu Thr Lys Thr Ala Ser Pro Val Phe Asp Ala Tyr
                325                 330                 335
```

```
Cys Lys Gln Thr Tyr Leu Asp Asn Ile Leu Arg Gly Gly Tyr Pro Ile
                340                 345                 350
Lys Leu Gly Lys Asp Lys Ile Phe Tyr Leu Tyr Ser Arg Lys His Gly
            355                 360                 365
Asp Ile Glu Arg Asp Tyr Asn Phe Phe Ser Met Leu Pro Glu Tyr Tyr
        370                 375                 380
Ser Gln Gly Asn Ala Asn Tyr Arg Asp Val Asn Gln Asn Arg Arg Cys
385                 390                 395                 400
Asp Val Leu Phe Ser Pro Phe Val Glu Asp Glu Cys Ile Lys Met Phe
                405                 410                 415
Tyr Asn Leu Ile Gln Ile Asp Gly Tyr Asn Pro Leu Ala Val Gln Lys
            420                 425                 430
Ala Thr Phe Cys Ile Pro Ser Glu Lys Met Glu Glu Ala Val Ser Ile
        435                 440                 445
Leu Pro Ile Lys Glu Lys Val Asn Gly Tyr Asn Phe Phe Gln Asn Ser
        450                 455                 460
Phe Thr Pro Gly Ser Phe Leu Gly Phe Leu Glu Gln Gln Gly Cys Thr
465                 470                 475                 480
Asp Lys Glu Thr Leu Glu Asn Thr Leu Ser Ser Val Met Glu Val Ser
                485                 490                 495
Glu Ser Glu Ile Ala Ala Ser Phe Gly Glu Gly Tyr Trp Val Asp His
            500                 505                 510
Trp Thr Tyr Asn Leu Asp Leu Val Glu Ala Phe Leu Ser Ile Tyr Pro
            515                 520                 525
Glu Arg Glu Glu Asp Leu Phe Tyr His Asp Ile Thr Tyr Thr Tyr Phe
        530                 535                 540
Glu Ser Met Ala Ile Val Asn Lys Arg Gln Asn Arg Tyr Val Glu Thr
545                 550                 555                 560
Lys Asn Gly Leu Arg Gln Tyr Lys Ser Leu Asp Lys Gly Ser Lys Lys
                565                 570                 575
Glu Val Ala His Lys Gln Leu Arg Cys Asp Tyr Gly Lys Gly Ser Val
            580                 585                 590
Tyr Gln Thr Ser Leu Leu Glu Lys Leu Leu Leu Ile Ser Ile Lys
            595                 600                 605
Ile Ala Thr Leu Asp Pro Glu Gly Met Gly Ile Glu Met Glu Ala Gly
        610                 615                 620
Lys Pro Gly Trp Tyr Asp Ala Leu Asn Gly Leu Pro Gly Ile Phe Gly
625                 630                 635                 640
Ser Ser Met Cys Glu Thr Ile Glu Leu Glu Arg Met Ile Ser Phe Val
                645                 650                 655
Leu Ser Ile Val Asn Arg Tyr Pro Asn Asn Val Pro Val Ala Leu Glu
            660                 665                 670
Ile Lys Glu Leu Met Glu Asn Leu Tyr Glu Val Ser Arg Arg Glu Ile
        675                 680                 685
Thr Ser Met Glu Ala Trp Asp Leu Arg Asn Asn Ser Lys Glu Asn Tyr
        690                 695                 700
Arg Glu Lys Thr Lys Leu Gly Val Glu Gly Thr Lys Glu Val Leu Met
705                 710                 715                 720
Val Glu Asp Ile Arg Ala Met Leu Thr Thr Trp Ser Phe Leu Val Lys
                725                 730                 735
Lys Gly Ile Glu Lys Ala Val Lys Leu Gly Lys Gly Ile Cys Pro Thr
            740                 745                 750
```

```
Tyr Phe Tyr Tyr Lys Ala Lys Glu Tyr Glu Lys Lys Glu Asp Gly Ile
            755             760             765

Phe Ile Lys Glu Phe Glu Leu Met Ser Met Pro Tyr Phe Leu Glu Gly
        770             775             780

Pro Val His Tyr Leu Lys Leu Glu Gln Ser Gln Glu Glu Lys Lys Arg
785             790             795                     800

Leu Tyr Gln Ala Val Lys Glu Ser Asn Leu Tyr Asp Arg Lys Leu Lys
                805             810                 815

Met Tyr Lys Val Asn Glu Ser Leu His Lys Ala Ser Phe Glu Val Gly
                820             825             830

Arg Ser Thr Ala Phe Thr Pro Gly Trp Leu Glu Asn Glu Ser Ile Trp
            835             840             845

Leu His Met Glu Tyr Lys Tyr Tyr Leu Glu Leu Leu Lys Ser Gly Leu
        850             855             860

Tyr Glu Glu Tyr Phe Glu Asp Phe Lys Asn Gly Leu Ile Pro Phe Leu
865             870             875                     880

Glu Glu Lys Lys Tyr Gly Arg Ser Ile Leu Glu Asn Ser Ser Phe Leu
                885             890             895

Ala Ser Ser Ala Asn Pro Asp Glu Lys Ile His Gly Lys Gly Phe Val
            900             905             910

Ala Arg Leu Ser Gly Ser Thr Ala Glu Phe Val His Met Trp Gln Ile
        915             920             925

Met Met Phe Gly His Asn Pro Phe Arg Tyr Glu Gln Glu Glu Leu Tyr
        930             935             940

Leu Ser Leu Glu Pro Ile Leu Pro Glu Tyr Leu Ile Gly Glu Asp Gly
945             950             955                     960

Val Ile Lys Ala Thr Phe Leu Gly Lys Ile Pro Val Cys Tyr Gln Leu
                965             970             975

Leu Lys Lys Lys Ala Leu Leu Pro Gly Arg Tyr Lys Val Glu Ser Tyr
            980             985             990

Thr Leu Gln Tyr Glu Asp Gly Glu  Ile Lys Gln Ile Ser  Glu Ser Lys
        995             1000            1005

Leu Pro Cys Lys Glu Ser Met  Asp Val Arg Asp Gly  Arg Val Asn
    1010            1015            1020

Ser Ile Ser Val Ser Ile Ser  Leu Glu His His His  His His His
    1025            1030            1035
```

SYNTHESIS OF GLUCAN COMPRISING BETA-1,3 GLYCOSIDIC LINKAGES WITH BETA-1,3-GLUCAN PHOSPHORYLASE ENZYMES This application claims the benefit of International Application No. PCT/CN2018/084036 (filed Apr. 23, 2018), which is incorporated herein by reference in its entirety.

FIELD

The present disclosure is in the field of enzymatic reactions. For example, the disclosure pertains to reactions and methods of producing beta-1,3-glucan using a beta-1,3-glucan phosphorylase.

REFERENCE TO SEQUENCE LISTING SUBMITTED ELECTRONICALLY

The official copy of the sequence listing is submitted electronically via EFS-Web as an ASCII formatted sequence listing with a file named 20190410_NB41430USNP_SequenceListing.txt created on Apr. 10, 2019, and having a size of about 156 kilobytes and is filed concurrently with the specification. The sequence listing contained in this ASCII-formatted document is part of the specification and is herein incorporated by reference in its entirety.

BACKGROUND

Driven by a desire to use polysaccharides in various applications, researchers have explored for polysaccharides that are biodegradable and that can be made economically from renewably sourced feedstocks. One such polysaccharide is beta-1,3-glucan, a glucan polymer characterized by having beta-1,3-glycosidic linkages. Different forms of beta-1,3-glucan have been prepared from various sources, such as algae, fungi, plants and bacteria (Stone, B. A., 2009, Chemistry of Beta-Glucans, In Antony Bacic et al., Eds., *Chemistry, Biochemistry, and Biology of* 1-3 *Beta Glucans and Related Polysaccharides*, Academic Press, Burlington, Mass.). Beta-1,3-glucan isolated from the cell walls of yeast and mushrooms can be large (well over 100 kDa) and/or branched in structure. Branching in fungal forms of beta-1,3-glucan can comprise pendent beta-1,6-linked glucoses, and/or spans of beta-1,3-glucan iteratively linked together through beta-1,6 linkage, for example. A plant-derived beta-glucan, callose, has mostly beta-1,3 glycosidic linkages and a small amount of beta-1,6 glycosidic linkages. Beta-1,3-glucan produced by members of the kingdom Protista include, for example, laminarin and paramylon, which are produced by brown algae and *Euglena*, respectively. While paramylon is high in molecular weight and consists of linear beta-1,3-glucan, laminarin is low in molecular weight and further comprises beta-1,6-linked branches. The bacterial beta-1,3-glucan, curdlan, is linear and of high molecular weight (e.g., over 100 kDa). These and other natural forms of beta-1,3-glucan can be synthesized in relatively large amounts in vivo by beta-1,3-glucan synthase enzymes, which utilize UDP-glucose as a substrate for glucan polymer synthesis (Brownfield, L. et al., 2009, Biochemical and Molecular Properties of Biosynthetic Enzymes for (1,3)-Beta-Glucans in Embryophytes, Chlorophytes and Rhodophytes; Nogami, S. et al., 2009, Biosynthetic Enzymes for (1-3)-Beta-Glucans, (1-3;1-6)-Beta-Glucans from Yeasts: Biochemical Properties and Molecular Biology; Bulone, V., 2009, Biosynthetic Enzymes for (1,3)-Beta-Glucans and (1,3;1,6)-Beta-Glucans in Protozoans and Chromistans: Biochemical Characterization and Molecular Biology; Stanisich, V. A., 2009, Enzymology and Molecular Genetics of Biosynthetic Enzymes for (1,3)-Beta-Glucans: Prokaryotes; Each in Antony Bacic et al., Eds., *Chemistry, Biochemistry, and Biology of* 1-3 *Beta Glucans and Related Polysaccharides*, Academic Press, Burlington, Mass.).

Isolated phosphorylase enzymes have been used to produce beta-1,3-glucan in vitro (e.g., Yamamoto et al., 2013, *Biosci. Biotechnol. Biochem.* 77:1949-1954; U.S. Pat. No. 8,530,202). Further ways of producing glucan containing beta-1,3 glycosidic linkages with isolated glucan phosphorylases are presently disclosed.

SUMMARY

In one embodiment, the present disclosure concerns a reaction composition comprising at least water, alpha-G1P, an acceptor molecule, and a beta-1,3-glucan phosphorylase enzyme comprising an amino acid sequence that is at least 90% identical to SEQ ID NO:2, SEQ ID NO:4, SEQ ID NO:6, SEQ ID NO:8, SEQ ID NO:10, or SEQ ID NO:12, wherein the enzyme synthesizes beta-1,3-glucan.

In another embodiment, the present disclosure concerns a method for producing beta-1,3-glucan (such as disclosed herein), the method comprising: (a) contacting at least water, alpha-G1P, an acceptor molecule, and a beta-1,3-glucan phosphorylase enzyme comprising an amino acid sequence that is at least 90% identical to SEQ ID NO:2, SEQ ID NO:4, SEQ ID NO:6, SEQ ID NO:8, SEQ ID NO:10, or SEQ ID NO:12, wherein beta-1,3-glucan is produced; and (b) optionally, isolating the beta-1,3-glucan produced in step (a).

In another embodiment, the present disclosure concerns a method of processing beta-1,3-glucan (such as disclosed herein), the method comprising: (a) providing an aqueous composition comprising up to about 40 wt % insoluble beta-1,3-glucan having a degree of polymerization (DP) of at least 17; (b) heating the aqueous composition to at least about 75° C., thereby dissolving the beta-1,3-glucan in the aqueous composition to provide a solution; (c) subjecting the solution to at least one process that reduces the content of one or more solutes other than the dissolved beta-1,3-glucan, thereby increasing the content of the dissolved beta-1,3-glucan in the solution on a dry weight basis; and (d) optionally cooling the solution to a temperature at which the beta-1,3-glucan precipitates back to an insoluble state, and optionally isolating the precipitated beta-1,3-glucan.

BRIEF DESCRIPTION OF THE SEQUENCES

TABLE 1

Summary of Nucleic Acid and Protein SEQ ID Numbers

| Description | Nucleic acid SEQ ID NO. | Protein SEQ ID NO. |
|---|---|---|
| "PstGp1", *Paenibacillus stellifer* DSM 14472 beta-1,3-glucan phosphorylase (CRC12021). | 1 | 2 (1087 aa) |
| "GmaGp1", *Gorillibacterium massiliense* G5 beta-1,3-glucan phosphorylase (CRC12023). | 3 | 4 (1077 aa) |

TABLE 1-continued

Summary of Nucleic Acid and Protein SEQ ID Numbers

| Description | Nucleic acid SEQ ID NO. | Protein SEQ ID NO. |
|---|---|---|
| "PspGp2", *Paenibacillus* sp. FSL H8-237 beta-1,3-glucan phosphorylase (CRC12024). | 5 | 6 (1075 aa) |
| "CauGp1", *Caloramator australicus* RC3 beta-1,3-glucan phosphorylase (CRC12026). | 7 | 8 (1071 aa) |
| "CgrGp1", *Clostridium grantii* DSM 8605 beta-1,3-glucan phosphorylase (CRC12027). | 9 | 10 (1060 aa) |
| "LphGp1", *Lachnoclostridium phytofermentans* KNHs2131 beta-1,3-glucan phosphorylase (CRC12030). | 11 | 12 (1030 aa) |
| PstGp1 with additional C-terminal residues including a 6x-His tag. Nucleotide sequence codon-optimized for expression in *Escherichia coli*. | 13 | 14 (1095 aa) |
| GmaGp1 with additional C-terminal residues including a 6x-His tag. Nucleotide sequence codon-optimized for expression in *E. coli*. | 15 | 16 (1085 aa) |
| PspGp2 with additional C-terminal residues including a 6x-His tag. Nucleotide sequence codon-optimized for expression in *E. coli*. | 17 | 18 (1083 aa) |
| CauGp1 with additional C-terminal residues including a 6x-His tag. Nucleotide sequence codon-optimized for expression in *E. coli*. | 19 | 20 (1079 aa) |
| CgrGp1 with additional C-terminal residues including a 6x-His tag. Nucleotide sequence codon-optimized for expression in *E. coli*. | 21 | 22 (1068 aa) |
| LphGp1 with additional C-terminal residues including a 6x-His tag. Nucleotide sequence codon-optimized for expression in *E. coli*. | 23 | 24 (1038 aa) |

Detailed Description

The disclosures of all cited patent and non-patent literature are incorporated herein by reference in their entirety.

Unless otherwise disclosed, the terms "a" and "an" as used herein are intended to encompass one or more (i.e., at least one) of a referenced feature.

Where present, all ranges are inclusive and combinable, except as otherwise noted. For example, when a range of "1 to 5" (i.e., 1-5) is recited, the recited range should be construed as including ranges "1 to 4", "1 to 3", "1-2", "1-2 & 4-5", "1-3 & 5", and the like.

The term "saccharide" and other like terms herein refer to monosaccharides and/or disaccharides/oligosaccharides, unless otherwise noted. A "disaccharide" herein refers to a carbohydrate having two monosaccharides joined by a glycosidic linkage. An "oligosaccharide" herein can refer to a carbohydrate having 3 to 15 monosaccharides, for example, joined by glycosidic linkages. An oligosaccharide can also be referred to as an "oligomer". Monosaccharides (e.g., glucose and/or fructose) comprised within disaccharides/oligosaccharides can be referred to as "monomeric units", "monosaccharide units", or other like terms.

The terms "beta-glucan", "beta-glucan polymer" and the like are used interchangeably herein. A beta-glucan is a polymer comprising glucose monomeric units linked together by beta-glycosidic linkages. Beta-glucan herein can be in the form of an oligosaccharide or polysaccharide. In typical embodiments, a beta-glucan herein comprises at least about 80%, 81%, 82%, 83%, 84%, 85%, 86%, 87%, 88%, 89%, 90%, 91%, 92%, 93%, 94%, 95%, 96%, 97%, 98%, 99%, or 100% beta-glycosidic linkages. Examples of beta-glucan polymers herein include beta-1,3-glucan. Glucose as comprised within a saccharide, beta-glucan, or other carbohydrate herein can be referred to as glucose monomeric unit(s), glucose monomer(s), glucose units, or other like terms.

The terms "poly beta-1,3-glucan", "beta-1,3-glucan", "beta-1,3-glucan polymer" and the like are used interchangeably herein. Beta-1,3-glucan is a polymer of at least DP3 and comprises glucose monomeric units linked together by glycosidic linkages, wherein at least about 90% of the glycosidic linkages are beta-1,3. Beta-1,3-glucan in certain embodiments has about 100% beta-1,3 glycosidic linkages, or comprises at least about 90% or 95% beta-1,3 glycosidic linkages. Most or all of other linkages (if present) in beta-1,3-glucan herein typically are beta-1,6 (typically forming a branch).

The terms "glycosidic linkage", "glycosidic bond", "linkage" and the like are used interchangeably herein and refer to the covalent bond that joins a carbohydrate (sugar) molecule to another group such as another carbohydrate. The term "beta-1,3-glycosidic linkage" as used herein refers to the type of covalent bond that joins beta-D-glucose molecules to each other through carbons 1 and 3 on adjacent beta-D-glucose rings. The glycosidic linkages of a glucan polymer herein can also be referred to as "glucosidic linkages". Herein, "beta-D-glucose" is referred to as "glucose", unless otherwise noted.

The glycosidic linkage profile of a beta-glucan herein can be determined using any method known in the art. For example, a linkage profile can be determined using methods using nuclear magnetic resonance (NMR) spectroscopy (e.g., $^{13}$C NMR or $^{1}$H NMR). These and other methods that can be used are disclosed in, for example, *Food Carbohydrates: Chemistry, Physical Properties, and Applications* (S. W. Cui, Ed., Chapter 3, S. W. Cui, Structural Analysis of Polysaccharides, Taylor & Francis Group LLC, Boca Raton, Fla., 2005), which is incorporated herein by reference.

The "molecular weight" of large beta-glucan polymers herein can be represented as weight-average molecular weight (Mw) or number-average molecular weight (Mn), the units of which are in Daltons or grams/mole. Alternatively, the molecular weight of large beta-glucan polymers can be represented as DPw (weight average degree of polymerization) or DPn (number average degree of polymerization). The molecular weight of smaller beta-glucan polymers such as oligosaccharides typically can be provided as "DP" (degree of polymerization), which simply refers to the number of glucose monomeric units comprised within the beta-glucan. Various means are known in the art for calculating these various molecular weight measurements such as with high-pressure liquid chromatography (HPLC), size exclusion chromatography (SEC), or gel permeation chromatography (GPC).

Unless otherwise disclosed, the terms "phosphorylase", "phosphorylase enzyme" and the like as used herein refer to a particular class of enzymes belonging to the glycosyl hydrolase 94 (GH94) family according to the CAZy (Carbohydrate-Active EnZymes) database (cazy.org website; see Cantarel et al., 2009, *Nucleic Acids Res.* 37:D233-238, incorporated herein by reference). Such a phosphorylase can reversibly catalyze synthesis (such reversibility is typically only under isolated/in vitro conditions) of a certain type of disaccharide, oligosaccharide, or polysaccharide (e.g., beta-glucan) and free phosphate (reaction products) from alpha-glucose-1-phosphate (alpha-G1P) and a suitable acceptor (reaction substrates). A "beta-1,3-glucan phosphorylase" (or "phosphorylase enzyme that synthesizes beta-1,3-glucan", "1,3-beta-D-glucan phosphorylase", and like terms) herein catalyzes synthesis of beta-1,3 glycosidic linkage-containing oligosaccharides or polysaccharides and free phosphate from alpha-G1P and a suitable acceptor. A beta-1,3-glucan phosphorylase is of the Enzyme Commission (EC) entry 2.4.1.97, and in certain aspects catalyzes the following reversible reaction: alpha-G1P+(1,3-beta-D-glucosyl)$_{n-1}$↔(1,3-beta-glucosyl)$_n$+phosphate; while "(1,3-beta-D-glucosyl)$_{n-1}$" is shown as an acceptor in this reaction, a beta-1,3-glucan phosphorylase can use other acceptor types such as those disclosed herein. A beta-1,3-glucan phosphorylase in certain aspects comprises an amino acid sequence that is at least 90% identical to SEQ ID NO:2, 4, 6, 8, 10, or 12. Depending on the acceptor used in a beta-1,3-glucan phosphorylase reaction herein, a beta-1,3 glycosidic linkage-containing oligosaccharide or polysaccharide product can (i) be comprised entirely of glucose monomeric units (when acceptor itself is comprised only of one or more glucose units in certain aspects), or (ii) comprise non-glucose monosaccharide units and/or non-saccharide moieties in addition to glucose units (when acceptor itself comprises such other monosaccharide units and/or moieties). Either of these product types (i or ii), for example, can optionally be characterized with respect to the beta-1,3 glycosidic linkage-containing oligosaccharide or polysaccharide that was synthesized from the acceptor (i.e., the product linkage profile does not include the linkages of the acceptor).

The terms "acceptor", "acceptor molecule", "acceptor compound" and the like are used interchangeably herein. A suitable acceptor herein is contemplated to be an organic molecule comprising at least one hydroxyl moiety (—OH), which hydroxyl moiety is capable of being involved in formation of a glycosidic linkage (involving the oxygen atom of the hydroxyl moiety) with the 1-position of glucose of alpha-G1P (phosphate group is replaced during linkage formation) via catalytic activity of a beta-1,3-glucan phosphorylase herein. A suitable acceptor can be a carbohydrate or non-carbohydrate. Examples of non-carbohydrate acceptors include alcohols, polyols, phenolic compounds, and amino acids. Examples of carbohydrate acceptors include disaccharides, oligosaccharides and polysaccharides; all or some of the monomeric units of a carbohydrate acceptor in some embodiments can be glucose units. The non-reducing end of a carbohydrate acceptor is typically involved in glycosidic linkage formation. The term "initial acceptor" can optionally be used herein to characterize an acceptor as used when preparing a beta-1,3-glucan phosphorylase reaction. An initial acceptor has not yet had a glucose linked to it by beta-1,3-glucan phosphorylase. During a beta-1,3-glucan phosphorylase reaction, an acceptor typically serves iteratively as an acceptor for subsequent glucose addition by the phosphorylase.

"Glucose-1-phosphate" (G1P) as used herein refers to a glucose molecule with a phosphate group on the 1-carbon. G1P herein typically is alpha-D-glucose-1-phosphate (alpha-G1P), which is D-glucopyranose with alpha configuration at the anomeric center. Unless as otherwise disclosed, G1P herein is not beta-D-glucose-1-phosphate (beta-G1P).

"Inorganic phosphate", which can be denoted as "$P_i$", refers to a free phosphate ion in solution, and is distinguished from phosphate as bound in a phosphate ester such as G1P.

The terms "enzymatic reaction", "enzymatic reaction composition", "glucan phosphorylase reaction", "beta-1,3-glucan phosphorylase reaction" and like terms are used interchangeably herein and, except as otherwise noted, refer to a reaction that is performed by a beta-1,3-glucan phosphorylase enzyme. An enzymatic reaction generally refers to an aqueous solution/preparation comprising at least alpha-G1P, an acceptor, and an active beta-1,3-glucan phosphorylase enzyme. It is in such a reaction where the step of contacting water, alpha-G1P, acceptor and beta-1,3-glucan phosphorylase enzyme is performed. The term "under suitable reaction conditions" and like terms refer to reaction conditions that support conversion of substrates (alpha-G1P and acceptor) to beta-1,3-glucan (as extended from the acceptor) and free phosphate products via beta-1,3-glucan phosphorylase activity. It would be understood that, in certain embodiments, as a beta-1,3-glucan phosphorylase reaction produces insoluble beta-1,3-glucan product, such product is present out of solution (the reaction becomes a mixture).

A "control" enzymatic reaction as used herein refers to a reaction using a beta-1,3-glucan phosphorylase not comprising an amino acid sequence that is at least 90% identical to SEQ ID NO:2, 4, 6, 8, 10, or 12, for example. All the other features (e.g., substrate concentrations, temperature, pH, time) of a control reaction can be the same as the reaction to which it is being compared.

The term "laminaribiose" (also known as "beta-1,3-glucobiose") as used herein refers to the disaccharide 3-beta-D-glucosyl-D-glucose.

The terms "laminarin" "laminaran" and the like herein typically refer to a water-soluble beta-1,3-glucan of low molecular weight (e.g., DP less than ~40) with beta-1,6-linked branches (e.g., 1 branch in every 10 residues of beta-1,3-linked backbone).

An "alpha-G1P-producing enzyme" herein refers to an enzyme that can catalyze synthesis of products including at least alpha-G1P. Examples of alpha-G1P-producing enzymes include starch phosphorylase, sucrose phosphorylase, and cellodextrin phosphorylase.

"Starch phosphorylase" as used herein is of the EC entry 2.4.1.1 and can reversibly catalyze conversion of starch and inorganic phosphate to products including alpha-G1P. Such a reaction can also be written as: (1,4-alpha-D-glucosyl)$_n$+phosphate↔(1,4-alpha-D-glucosyl)$_{n-1}$+alpha-G1P.

A "starch debranching enzyme" as used herein refers to an enzyme that can catalyze hydrolysis of alpha-1,6 linkages that are at branch points in starch. Examples of starch debranching enzymes herein include pullulanase and isoamylase. A "pullulanase" as used herein is of the EC entry 3.2.1.41. An "isoamylase" as used herein is of the EC entry 3.2.1.68.

The term "sucrose" herein refers to a non-reducing disaccharide composed of an alpha-D-glucose molecule and a beta-D-fructose molecule linked by an alpha-1,2-glycosidic bond. Sucrose is known commonly as table sugar.

"Sucrose phosphorylase" as used herein is of the EC entry 2.4.1.7 and can reversibly catalyze conversion of sucrose and phosphate to fructose and alpha-G1P. Such a reaction can also be written as: sucrose+phosphate↔fructose+alpha-G1P.

A "cellodextrin phosphorylase" as used herein is of the EC entry 2.4.1.49 and can reversibly catalyze conversion of cellodextrin and phosphate to products including alpha-G1P. Such a reaction can also be written as: (1,4-beta-glucosyl)$_n$+phosphate↔(1,4-beta-D-glucosyl)$_{n-1}$+alpha-G1P.

"Cellulosic biomass", "cellulose-comprising biomass" and the like are used interchangeably herein and refer to material comprising the structural portion of plants (e.g., wood, stems) that cannot directly be used for food ingredients or as fermentation substrates.

"Endoglucanase" and "beta-1,4-endoglucanase" are used interchangeably herein and refer to an enzyme that can cleave internal bonds within cellulose chains, making shorter cellulose chains. Such shorter chains are suitable substrates for cellodextrin phosphorylase.

A "laminaribiose phosphorylase" as used herein is of the EC entry 2.4.1.31 and can reversibly catalyze conversion the following reaction: D-glucose+alpha-G1P↔3-beta-D-glucosyl-D-glucose+phosphate.

A "second reaction" as used herein refers to a reaction that is in addition to a beta-1,3-glucan phosphorylase reaction ("first reaction"), and which provides alpha-G1P substrate for the first reaction. A second reaction herein can optionally be characterized as an "alpha-G1P-producing reaction". The combination of at least first and second reactions herein is a form of a "coupled reaction". A second reaction herein typically provides alpha-G1P by using a phosphorylase and free phosphate to phosphorolyze a disaccharide, oligosaccharide, or polysaccharide, which phosphorolysis produces at least alpha-G1P.

A "third reaction" as used herein refers to a reaction that is in addition to a beta-1,3-glucan phosphorylase reaction ("first reaction"), and which provides acceptor substrate for the first reaction. A third reaction herein can optionally be characterized as an "acceptor-producing reaction". The combination of at least first and third reactions herein is another form of a "coupled reaction". Yet another form of a coupled reaction herein comprises all three of first, second and third reactions. A third reaction herein typically provides an acceptor (e.g., laminaribiose) by using a phosphorylase that is not a beta-1,3-glucan phosphorylase (e.g., laminaribiose phosphorylase), G1P (e.g., alpha-G1P) and a suitable acceptor (e.g., glucose).

The term "nanofiltration" herein refers to a filtration process in which a low to moderately high pressure (typically 5-30 bar) transports solvent and some solute(s) (e.g., monosaccharides) through a semi-permeable membrane with some solute(s) (e.g., beta-1,3-glucan) being retained. A semi-permeable membrane for nanofiltration herein can have pore sizes between 0.1 nm to 10 nm and/or molecular weight cut-off (MWCO) between 100-5000 Daltons, for example. The term "ultrafiltration" herein refers to a filtration process using a semi-permeable membrane, typically with larger pore sizes than used in nanofiltration, for removing solvent and small solute(s) from larger solutes (e.g., beta-1,3-glucan). Material that passes through the membrane of a nanofiltration or ultrafiltration unit can be referred to as "permeate", whereas material that does not pass through the membrane can be referred to as either "concentrate" or "retentate".

The terms "percent by volume", "volume percent", "vol %", "v/v %" and the like are used interchangeably herein. The percent by volume of a solute in a solution can be determined using the formula: [(volume of solute)/(volume of solution)]×100%.

The terms "percent by weight", "weight percentage (wt %)", "weight-weight percentage (% w/w)" and the like are used interchangeably herein. Percent by weight refers to the percentage of a material on a mass basis as it is comprised in a composition, mixture, or solution.

The terms "dry weight basis" (dwb), "dry solids basis" (dsb) and the like are used interchangeably herein. The amount of a material (e.g., beta-1,3-glucan) on a dry weight basis in a solution, for example, refers to the weight percentage of the material as it exists in all the dissolved material (e.g., beta-1,3-glucan, fructose, sucrose, glucose, optionally salts and impurities) in the solution. For example, if a solution comprises 20% (dwb) dissolved beta-1,3-glucan, there would be 20 wt % beta-1,3-glucan in the dry matter resulting from removing all the water from the solution.

The "percent dry solids" (percent DS) of a solution herein refers to the wt % of all the materials (i.e., the solids) dissolved in the solution. For example, a 100 g solution with 10 wt % DS comprises 10 g of dissolved material.

The terms "aqueous liquid", "aqueous fluid" and the like as used herein can refer to water or an aqueous solution. An "aqueous solution" herein can comprise one or more dissolved salts, where the maximal total salt concentration can be about 3.5 wt % in some embodiments. Although aqueous liquids herein typically comprise water as the only solvent in the liquid, an aqueous liquid can optionally comprise one or more other solvents (e.g., polar organic solvent) that are miscible in water. Thus, an aqueous solution can comprise a solvent having at least about 10 wt % water.

An "aqueous composition" herein has a liquid component that comprises at least about 10 wt % water, for example. Examples of aqueous compositions include mixtures, solutions, dispersions (e.g., colloidal dispersions), suspensions and emulsions, for example.

As used herein, the term "colloidal dispersion" refers to a heterogeneous system having a dispersed phase and a dispersion medium, i.e., microscopically dispersed insoluble particles are suspended throughout another substance (e.g., an aqueous composition such as water or aqueous solution). An example of a colloidal dispersion herein is a hydrocolloid. All, or a portion of, the particles of a colloidal dispersion such as a hydrocolloid can comprise insoluble beta-glucan of the present disclosure. The terms "dispersant" and "dispersion agent" are used interchangeably herein to refer to a material that promotes the formation and/or stabilization of a dispersion.

A glucan that is "insoluble", "aqueous-insoluble", "water-insoluble" (and like terms) (e.g., insoluble beta-1,3-glucan) does not dissolve (or does not appreciably dissolve) in water or other aqueous conditions, optionally where the aqueous conditions are further characterized to have a pH of 4-9 (e.g., pH 6-8) (i.e., non-caustic) and/or a temperature of about 1 to 74° C. (e.g., 20-45° C. or 20-40° C.). In contrast, glucans herein that are "soluble", "aqueous-soluble", "water-soluble" and the like (e.g., soluble beta-1,3-glucan) appreciably dissolve under these conditions. In some aspects herein, a beta-1,3-glucan that is aqueous-insoluble per the above definition becomes aqueous-soluble at a temperature of at least about 75° C.

The terms "sequence identity", "identity" and the like as used herein with respect to polynucleotide or polypeptide sequences refer to the nucleic acid residues or amino acid residues in two sequences that are the same when aligned for maximum correspondence over a specified comparison window. Thus, "percentage of sequence identity", "percent identity" and the like refer to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. It would be understood that, when calculating sequence identity between a DNA sequence and an RNA sequence, T residues of the DNA sequence align with, and can be considered "identical" with, U residues of the RNA sequence. For purposes of determining "percent complementarity" of first and second polynucleotides, one can obtain this by determining (i) the percent identity between the first polynucleotide and the complement sequence of the second polynucleotide (or vice versa), for example, and/or (ii) the percentage of bases between the first and second polynucleotides that would create canonical Watson and Crick base pairs.

Percent identity can be readily determined by any known method, including but not limited to those described in: 1) *Computational Molecular Biology* (Lesk, A. M., Ed.) Oxford University: NY (1988); 2) *Biocomputing: Informatics and Genome Projects* (Smith, D. W., Ed.) Academic: NY (1993); 3) *Computer Analysis of Sequence Data, Part I* (Griffin, A. M., and Griffin, H. G., Eds.) Humana: NJ (1994); 4) *Sequence Analysis in Molecular Biology* (von Heinje, G., Ed.) Academic (1987); and 5) *Sequence Analysis Primer* (Gribskov, M. and Devereux, J., Eds.) Stockton: NY (1991), all of which are incorporated herein by reference.

Preferred methods for determining percent identity are designed to give the best match between the sequences tested. Methods of determining identity and similarity are codified in publicly available computer programs, for example. Sequence alignments and percent identity calculations can be performed using the MEGALIGN program of the LASERGENE bioinformatics computing suite (DNASTAR Inc., Madison, Wis.), for example. Multiple alignment of sequences can be performed, for example, using the Clustal method of alignment which encompasses several varieties of the algorithm including the Clustal V method of alignment (described by Higgins and Sharp, *CABIOS.* 5:151-153 (1989); Higgins, D. G. et al., *Comput. Appl. Biosci.,* 8:189-191 (1992)) and found in the MEGALIGN v8.0 program of the LASERGENE bioinformatics computing suite (DNASTAR Inc.). For multiple alignments, the default values can correspond to GAP PENALTY=10 and GAP LENGTH PENALTY=10. Default parameters for pairwise alignments and calculation of percent identity of protein sequences using the Clustal method can be KTUPLE=1, GAP PENALTY=3, WINDOW=5 and DIAGONALS SAVED=5. For nucleic acids, these parameters can be KTUPLE=2, GAP PENALTY=5, WINDOW=4 and DIAGONALS SAVED=4. Additionally, the Clustal W method of alignment can be used (described by Higgins and Sharp, *CABIOS.* 5:151-153 (1989); Higgins, D. G. et al., *Comput. Appl. Biosci.* 8:189-191(1992); Thompson, J. D. et al., *Nucleic Acids Research,* 22 (22): 4673-4680, 1994) and found in the MEGALIGN v8.0 program of the LASERGENE bioinformatics computing suite (DNASTAR Inc.). Default parameters for multiple alignment (protein/nucleic acid) can be: GAP PENALTY=10/15, GAP LENGTH PENALTY=0.2/6.66, Delay Divergen Seqs (%)=30/30, DNA Transition Weight=0.5, Protein Weight Matrix=Gonnet Series, DNA Weight Matrix=IUB.

Various polypeptide amino acid sequences and polynucleotide sequences are disclosed herein as features of certain embodiments. Variants of these sequences that are at least about 70-85%, 85-90%, or 90%-95% identical to the sequences disclosed herein can be used or referenced. Alternatively, a variant amino acid sequence or polynucleotide sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identity with a sequence disclosed herein. The variant amino acid sequence or polynucleotide sequence has the same function/activity of the disclosed sequence, or at least about 80%, 81%, 82%, 83%, 84%, 85%, 86%, 87%, 88%, 89%, 90%, 91%, 92%, 93%, 94%, 95%, 96%, 97%, 98%, or 99% of the function/activity of the disclosed sequence. Any polypeptide amino acid sequence disclosed herein not beginning with a methionine can typically further comprise at least a start-methionine at the N-terminus of the amino acid sequence. In contrast, any polypeptide amino acid sequence disclosed herein beginning with a methionine can optionally lack such a methionine residue.

The term "isolated" as used herein characterizes a substance (or process) in a form or environment that does not occur in nature. A non-limiting example of an isolated substance includes any non-naturally occurring substance such as beta-1,3-glucan or any other polymer as synthesized herein (as well as any of the presently disclosed beta-1,3-glucan phosphorylases and reactions/processes using these enzymes). It is believed that the embodiments disclosed herein are synthetic/man-made (could not have been made except for human intervention/involvement), and/or have properties that are not naturally occurring.

The term "increased" as used herein can refer to a quantity or activity that is at least about 1%, 2%, 3%, 4%, 5%, 6%, 7%, 8%, 9%, 10%, 11%, 12%, 13%, 14%, 15%, 16%, 17%, 18%, 19%, 20%, 50%, 100%, or 200% more than the quantity or activity for which the increased quantity or activity is being compared. The terms "increased", "elevated", "enhanced", "greater than", "improved" and the like are used interchangeably herein.

Reactions and methods for producing glucan containing beta-1,3 glycosidic linkages with isolated glucan phosphorylases are presently disclosed.

Certain embodiments of the present disclosure concern a reaction composition comprising at least water, alpha-glucose-1-phosphate (alpha-G1P), a suitable acceptor molecule, and a beta-1,3-glucan phosphorylase enzyme comprising an amino acid sequence that is at least 90% identical to SEQ ID NO:2, SEQ ID NO:4, SEQ ID NO:6, SEQ ID NO:8, SEQ ID NO:10, or SEQ ID NO:12, wherein the enzyme synthesizes beta-1,3-glucan. Significantly, such an enzymatic reaction produces beta-1,3-glucan in a manner that, if desired, is completely independent from using a beta-1,3-glucan synthase.

A beta-1,3-glucan phosphorylase suitable for use in an enzymatic reaction as presently disclosed can comprise, or consist of, an amino acid sequence that is 100% identical to, or at least 80%, 81%, 82%, 83%, 84%, 85%, 86%, 87%, 88%, 89%, 90%, 91%, 92%, 93%, 94%, 95%, 96%, 97%, 98%, 99%, or 99.5% identical to, SEQ ID NO:2, 4, 6, 8, 10, or 12, for example. In some aspects, a beta-1,3-glucan phosphorylase enzyme with between 80-99.5% amino acid identity with SEQ ID NO:2, 4, 6, 8, 10, or 12 can have some of (e.g., at least 30%, 40%, 50%, 60%, 70%, 80%, or 90% of), or all of, the enzymatic activity of a beta-1,3-glucan phosphorylase of SEQ ID NO:2, 4, 6, 8, 10, or 12, respectively. Examples of a beta-1,3-glucan phosphorylase comprising SEQ ID NO:2, 4, 6, 8, 10, or 12, include, respectively, SEQ ID NO:14, 16, 18, 20, 22, or 24.

A polynucleotide sequence herein encoding SEQ ID NO:2, 4, 6, 8, 10, or 12 (or a related amino acid sequence with ≥80% or ≥90% identity thereto) can optionally comprise a nucleotide sequence that is 100% identical to, or at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to, SEQ ID NO:1, 3, 5, 7, 9, or 11, respectively. Examples of such sequences herein are SEQ ID NOs:13, 15, 17, 19, 21, or 23, respectively.

Given that certain amino acids share similar structural and/or charge features with each other (i.e., conserved), one or more amino acids of a beta-1,3-glucan phosphorylase sequence herein (and/or other types of polypeptides herein) can optionally be substituted with a conserved amino acid residue ("conservative amino acid substitution") as follows:
1. The following small aliphatic, nonpolar or slightly polar residues can substitute for each other: Ala (A), Ser (S), Thr (T), Pro (P), Gly (G);
2. The following polar, negatively charged residues and their amides can substitute for each other: Asp (D), Asn (N), Glu (E), Gln (Q);
3. The following polar, positively charged residues can substitute for each other. His (H), Arg (R), Lys (K);
4. The following aliphatic, nonpolar residues can substitute for each other: Ala (A), Leu (L), Ile (I), Val (V), Cys (C), Met (M); and
5. The following large aromatic residues can substitute for each other: Phe (F), Tyr (Y), Trp (W).

In some aspects, a beta-1,3-glucan phosphorylase enzyme herein can be obtained (or is obtainable) from a microbial source, such as a bacteria, fungus (e.g., yeast), or protist. Examples of bacteria herein include *Paenibacillus, Gorillibacterium, Caloramator, Clostridium* and *Lachnoclostridium* species. Examples of *Paenibacillus* species herein include *P. stellifer, P. odorifer, P. etheri, P. sonchi, P. riograndensis, P. borealis, P. jilunlii* and *P. typhae*. Examples of *Gorillibacterium* species herein include *G. massiliense* and *G. timonense*. Examples of *Caloramator* species herein include *C. australicus, C. fervidus* and *C. mitchellensis*. Examples of *Clostridium* species herein include *C. grantii, C. ganghwense* and *C. aestuarii*. Examples of *Lachnoclostridium* species herein include *L. phytofermentans* and *L. massiliosenegalense*.

Examples of enzymes with beta-1,3-glucan phosphorylase activity herein can be any of the disclosed beta-1,3-glucan phosphorylase amino acid sequences and that further include 1-300 (or any integer there between [e.g., 10, 20, 30, 40, 50, 75, 100, 150, 200, 250]) residues on the N-terminus and/or C-terminus. Such additional residues may be a heterologous sequence such as an epitope tag (at either N- or C-terminus) or a heterologous signal peptide (at N-terminus), for example. In those embodiments in which a heterologous amino acid sequence is incorporated at the N-terminus, such a heterologous sequence can be adjacent to the original start-methionine of the beta-1,3-glucan phosphorylase, or can replace the original start methionine, for example. In the latter embodiment, a new start-methionine can be at the N-terminus of the heterologous sequence.

An enzyme with beta-1,3-glucan phosphorylase activity as presently disclosed typically lacks an N-terminal signal peptide. However, an expression system for producing a beta-1,3-glucan phosphorylase enzyme can optionally employ an enzyme-encoding polynucleotide that further comprises sequence encoding an N-terminal signal peptide to direct extra-cellular secretion. The signal peptide in such embodiments is cleaved from the enzyme during the secretion process. Since it is believed that beta-1,3-glucan phosphorylase enzymes disclosed herein (e.g., SEQ ID NOs:2, 4, 6, 8, 10 and 12) are not associated with a signal peptide, any added signal peptide can be considered as heterologous to the enzyme. An example of a signal peptide herein is one from a bacterial species (e.g., a *Bacillus* species such as *B. subtilis*) or fungal species.

A beta-1,3-glucan phosphorylase herein can be prepared by fermentation of an appropriately engineered microbial strain, for example. Recombinant enzyme production by fermentation is well known in the art using microbial species such as *E. coli, Bacillus* strains (e.g., *B. subtilis*), *Ralstonia eutropha, Pseudomonas fluorescens, Saccharomyces cerevisiae, Pichia pastoris, Hansenula polymorpha*, and species of *Aspergillus* (e.g., *A. awamori*), *Trichoderma* (e.g., *T. reesei*) and *Myceliophthora* (e.g., *M. thermophila*) (e.g., see Adrio and Demain, *Biomolecules* 4:117-139, 2014, which is incorporated herein by reference). A nucleotide sequence encoding a beta-1,3-glucan phosphorylase amino acid sequence is typically linked to a heterologous promoter sequence to create an expression cassette for the enzyme, and/or is codon-optimized accordingly. Such an expression cassette may be incorporated in a suitable plasmid or integrated into the microbial host chromosome, using methods well known in the art. The expression cassette may include a transcriptional terminator nucleotide sequence following the amino acid coding sequence. The expression cassette may also include, between the promoter sequence and phosphorylase amino acid coding sequence, a nucleotide sequence encoding a signal peptide (e.g., heterologous signal peptide) that is designed for direct secretion of the beta-1,3-glucan phosphorylase. At the end of fermentation, cells may be ruptured accordingly (typically when a signal peptide for secretion is not employed) and the phosphorylase can be isolated using methods such as precipitation, filtration, and/or concentration. Alternatively, a lysate or extract comprising a phosphorylase can be used without further isolation. If the beta-1,3-glucan phosphorylase was secreted (i.e., it is present in the fermentation broth), it can optionally be used as isolated from, or as comprised in, the fermentation broth. The activity of a beta-1,3-glucan phosphorylase enzyme can be confirmed by biochemical assay, if desired, such as by measuring phosphorus release when placing the enzyme in a reaction herein containing alpha-G1P and a suitable acceptor (e.g., under conditions as described in Example 2 below). In some aspects, one unit of beta-1,3-glucan phosphorylase activity by an enzyme can be defined as the amount of enzyme that releases 1 µmol of inorganic phosphorus per minute in an aqueous reaction comprising about 10 mM alpha-G1P, about 1 mM acceptor (e.g., cellobiose or laminaribiose), and about 60 mM Tris-HCl buffer (about pH 7.0), incubated at about 37° C. for about 30 minutes. Inorganic phosphate release can optionally be gauged using the PiBlue™ Phosphate Assay Kit (BioAssay Systems, Hayward, Calif.). A beta-1,3-glucan phosphorylase enzyme herein is not believed to have cellobiose phosphorylase activity, for example. Since a beta-1,3-glucan phosphorylase enzyme herein produces oligosaccharides/polysaccharides, it would be understood that such an enzyme does not produce laminaribiose (i.e., it is not a laminaribiose phosphorylase).

A beta-1,3-glucan phosphorylase reaction herein produces beta-1,3-glucan. In some aspects, about, or at least about, 90%, 91%, 92%, 93%, 94%, 95%, 96%, 97%, 98%, 99%, 99.5%, or 100% of the constituent glycosidic linkages of beta-1,3-glucan herein are beta-1,3 linkages. In some aspects, accordingly, beta-1,3-glucan has about, or less than about, 10%, 9%, 8%, 7%, 6%, 5%, 4%, 3%, 2, 1%, 0.5%, or 0% glycosidic linkages that are not beta-1,3. It should be understood that the higher the percentage of beta-1,3 linkages present in beta-1,3-glucan, the greater the probability that the beta-1,3-glucan is linear, since there are lower occurrences of certain linkages forming branch points in the polymer. Thus, beta-1,3-glucan with 100% beta-1,3 linkages is completely linear. In certain embodiments, beta-1,3-glucan has no branch points or less than about 5%, 4%, 3%, 2%, or 1% branch points (typically beta-1,6) as a percent of the glycosidic linkages in the polymer. In some aspects, a given linkage profile characterizes that of the beta-1,3-glucan as synthesized from an acceptor (i.e., the linkage profile does not include the linkage profile of the acceptor). In aspects in which laminaribiose is used as the initial acceptor molecule, any of the foregoing linkage percentages can optionally characterize the entire product.

Beta-1,3-glucan herein can have a molecular weight in DP of about, or at least about, 3, 4, 5, 6, 7, 8, 9, 10, 11, 12, 13, 14, 15, 16, 17, 18, 19, 20, 21, 22, 23, 24, 25, 26, 27, 28, 29, 30, 3-15, 3-20, 3-25, 3-30, 5-15, 5-20, 5-25, 5-30, 10-15, 10-20, 10-25, 10-30, 15-17, 15-18, 15-19, 15-20, 15-21, 15-22, 15-23, 15-24, 15-25, 15-30, 16-17, 16-18, 16-19, 16-20, 16-21, 16-22, 16-23, 16-24, 16-25, 16-30, 17-18, 17-19, 17-20, 17-21, 17-22, 17-23, 17-24, 17-25, 17-30, 20-25, 20-30, or 25-30, for example. In some further aspects, the DP can be less than about 30, 25, 24, 23, 22, 21, 20, or 19. In some other aspects, the DP can be about, at least about, or up to about, 40, 50, 60, 70, 80, 90, or 100. In some aspects, any of the aforementioned DP values (e.g., 8 or greater) can instead be represented in terms of DPw or DPn. In some aspects, a given molecular weight characterizes that of the beta-1,3-glucan as synthesized from an acceptor (i.e., the molecular weight does not include the molecular weight of the acceptor). In aspects in which laminaribiose is used as the initial acceptor molecule, any of the foregoing molecular weight disclosures can optionally characterize the entire product.

Beta-1,3-glucan in some aspects is insoluble in aqueous conditions. Such insolubility is in non-caustic aqueous conditions, such as those conditions of a beta-1,3-glucan phosphorylase reaction herein (see below). Linear beta-1,3-glucan of DP 17 or 18 is shown in Example 3 below to be aqueous-insoluble at about 37° C., but aqueous-soluble at about 80-85° C. Thus, it is contemplated that, in certain aspects, linear beta-1,3-glucan (typically 100% beta-1,3 linkages) with a DP of at least 17 or 18 is insoluble, and that linear beta-1,3-glucan with a DP of 16 or less, or 15 or less, is soluble, in non-caustic aqueous conditions at a temperature of less than about 75, 74, 73, 72, 71, 70, 65, 60, 55, or 50° C. It is contemplated that linear beta-1,3-glucan herein with a DP of 30, 29, 28, 27, 26, 25, 24, 23, 22, 21, 20, 19 or less is aqueous-soluble in non-caustic aqueous conditions at a temperature of at least about 75, 76, 77, 78, 79, 80, 81, 82, 83, 84, 85, 86, 87, 88, 89, 90, 91, 92, 93, 94, 95° C. or higher. Non-caustic aqueous conditions (or aqueous conditions herein) can include, for example, water or an aqueous solution with a solvent having about, or at least about, 10, 20, 30, 40, 50, 60, 70, 80, 90, 95, 98%, 99%, or 100 wt % water, and a pH of 4-9 (e.g., pH 4-8 or 6-8).

Beta-1,3-glucan herein is typically enzymatically derived in an inert vessel (typically under cell-free conditions) (in vitro), and is not derived from a cell wall (e.g., plant, fungal, protist [e.g., algal], or bacterial cell wall). Some embodiments are drawn to beta-1,3-glucan as produced by, or that are producible (obtainable) by, any of the enzymatic reaction processes/conditions disclosed herein.

A suitable acceptor molecule is used in a beta-1,3-glucan phosphorylase reaction herein, and can optionally be characterized as an "initial acceptor" since it typically is added when first preparing a reaction.

In some aspects, an acceptor molecule comprises a monosaccharide, disaccharide, or oligosaccharide. Yet in some aspects, an acceptor consists of a monosaccharide, disaccharide, or oligosaccharide (e.g., the saccharide acceptor is not chemically derivatized/substituted). A disaccharide or oligosaccharide acceptor molecule typically comprises one or more glucose monomeric units (e.g., at least about 10%, 20%, 30%, 40%, 50%, 60%, 70%, 80%, 90%, or 95% of the monomeric units are glucose), or comprises only glucose monomeric units. A disaccharide or oligosaccharide can optionally comprise, typically in addition to one or more glucose monomeric units, one or more non-glucose monomeric units. In some aspects, a disaccharide or oligosaccharide comprises only non-glucose monomeric units. A non-glucose monomeric unit of a disaccharide or oligosaccharide (or a non-glucose monosaccharide acceptor) can be fructose, arabinose, xylose, or galactose in some aspects. Still, in some aspects a monosaccharide acceptor can be p-nitrophenyl beta-D-glucopyranoside or methyl beta-D-glucopyranoside. In some aspects, an acceptor is not (does not consist of) glucose, fructose, mannose, or glucosamine. An acceptor can be linear (no branches) or branched, for example.

A disaccharide or oligosaccharide acceptor molecule herein can comprise beta-glycosidic linkages and/or alpha-glycosidic linkages. The linkages of an acceptor can be 100% beta-glycosidic linkages, or at least about 50%, 60%, 70%, 80%, 90%, or 95% beta-glycosidic linkages, for example. Beta- or alpha-glycosidic linkages between glucose monomers of a disaccharide or oligosaccharide acceptor can comprise one type of, or more than one type of, the following linkages: 1,1; 1,2; 1,3; 1,4; and/or 1,6. Just to illustrate, the linkages can be all beta-1,3 glucosidic linkages or all beta-1,6 glucosidic linkages, or a mix of beta-1,3 and beta-1,6 glucosidic linkages.

An oligosaccharide acceptor herein can have, have at least, or have up to, 3, 4, 5, 6, 7, 8, 9, 10, 11, 12, 13, 14, or 15 monomeric units, for example. Particular examples of disaccharide and oligosaccharide acceptor molecules herein comprise, or consist of, laminaribiose, cellobiose, sophorose, laminaritriose, laminaritetraose, laminaripentaose, laminarihexaose, laminariheptaose, cellotriose, cellotetraose, cellopentaose, or gentiobiose. In some aspects, an acceptor molecule comprises, or consists of, laminaribiose or a DP3-15 laminarioligosaccharide such as laminaritriose, laminaritetraose, laminaripentaose, laminarihexaose, or laminariheptaose. In some aspects, an acceptor can be a p-nitrophenyl or methyl derivative of a disaccharide or oligosaccharide as disclosed herein.

In some aspects, an acceptor molecule comprises a polysaccharide. Yet in some aspects, an acceptor consists of a polysaccharide (e.g., the polysaccharide acceptor is not chemically derivatized/substituted). A polysaccharide acceptor molecule typically comprises one or more glucose monomeric units (e.g., at least about 10%, 20%, 30%, 40%, 50%, 60%, 70%, 80%, 90%, or 95% of the monomeric units are glucose), or comprises only glucose monomeric units (i.e., glucan). A polysaccharide can optionally comprise, typically in addition to one or more glucose monomeric units, one or more non-glucose monomeric units. A non-glucose monomeric unit of a polysaccharide can be fructose, arabinose, xylose, or galactose in some aspects.

A polysaccharide acceptor molecule herein can comprise beta-glycosidic linkages and/or alpha-glycosidic linkages. The linkages of a polysaccharide acceptor can be 100% beta-glycosidic linkages (e.g., beta-glucan), or at least about 50%, 60%, 70%, 80%, 90%, or 95% beta-glycosidic linkages, for example. Beta- or alpha-glycosidic linkages between glucose monomers of a polysaccharide acceptor can comprise one type of, or more than one type of, the following linkages: 1,1; 1,2; 1,3; 1,4; and/or 1,6. Just to illustrate, the linkages can be all beta-1,3 glucosidic linkages, or a mix of beta-1,3 and beta-1,6 glucosidic linkages (e.g., beta-1,3-glucan with pendant beta-1,6-linked glucose groups, or spans of beta-1,3-glucan iteratively linked together through beta-1,6 linkage [i.e., branch-on-branch]).

A polysaccharide acceptor herein can have a DP or DPw of about, or at least about, 16, 17, 18, 19, 20, 21, 22, 23, 24, 25, 26, 27, 28, 29, 30, 35, 40, 45, 50, 75, 100, 150, 200, 250, 300, 400, or 500, for example. This DP/DPw can optionally be expressed as a range between any two of these values. Merely as examples, the DP/DPw can be about 16-30, 16-40, 16-50, 16-30, 16-40, 20-50, 25-30, 25-40, 25-50, 30-40, or 30-50.

Examples of polysaccharide acceptors herein can comprise, or consist of, laminarin, mycolaminarin, or chrysolaminarin. A polysaccharide acceptor herein typically is aqueous-soluble.

An acceptor in some aspects can be a beta-glucan, particularly a soluble beta-glucan, as disclosed in Stone, B. A. (2009, Chemistry of Beta-Glucans, In Antony Bacic et al., Eds., *Chemistry, Biochemistry, and Biology of* 1-3 *Beta Glucans and Related Polysaccharides*, Academic Press, Burlington, Mass.), which is incorporated herein by reference.

The temperature of a beta-1,3-glucan phosphorylase reaction herein can be controlled, if desired. In some aspects, the temperature is between about 5° C. to about 50° C. The temperature in some aspects is between about 20° C. to about 42° C. In still some aspects, the temperature is about 20, 21, 22, 23, 24, 25, 26, 27, 28, 29, 30, 31, 32, 33, 34, 35, 36, 37, 38, 39, 40, 41, or 42° C.

The pH of a beta-1,3-glucan phosphorylase reaction composition in some aspects can be about 4.0-9.0, 4.0-8.5, 4.0-8.0, 5.0-8.0, 6.0-8.0, 5.5-7.5, or 5.5-6.5. In some aspects, the pH can be about 4.0, 4.5, 5.0, 5.5, 6.0, 6.5, 7.0, 7.5, or 8.0. The pH can be adjusted or controlled by the addition or incorporation of a suitable buffer, including but not limited to: phosphate (e.g., sodium phosphate buffer), tris (tris [hydroxymethyl] aminomethane; e.g., Tris-HCl), citrate, or a combination thereof. Buffer concentration in the enzymatic reaction can be from 0 mM to about 100 mM, or about 10, 25, 50, or 75 mM, for example. In some aspects, a buffer comprises, or consists of, tris; in this and some other aspects, a buffer optionally does not comprise phosphate.

The initial concentration of alpha-G1P in a beta-1,3-glucan phosphorylase reaction herein can be about, or at least about, 1 to 100 mM, for example. Also for example, the alpha-G1P initial concentration can be about, or at least about, 1, 5, 10, 20, 30, 40, 50, 60, 70, 80, 90, or 100 mM, or about 10-50 mM. The initial concentration of an acceptor in a beta-1,3-glucan phosphorylase reaction herein can be about 1 to 50 mM, for example. In some aspects, the initial concentration of an acceptor can be about, or at least about, 1, 5, 10, 15, 20, 25, 30, 35, 40, 45, or 50 mM, or about 1-10 or 5-10 mM. Still, in some aspects, the initial concentration of an acceptor can be about, or at least about, 0.05, 0.1, 0.5, 1.0, 2.5, 5, 7.5, or 10 g/L. "Initial concentration" of a substrate such as alpha-G1P or acceptor refers to the substrate concentration in an enzymatic reaction just after all the reaction components have been added (at least water, alpha-G1P, acceptor, beta-1,3-glucan phosphorylase).

The amount of a beta-1,3-glucan phosphorylase enzyme (active enzyme) comprised in an enzymatic reaction in some aspects can be about 0.01-60 mg/mL. For example, about, or at least about, 0.01, 0.05, 0.1, 0.5, 1, 5, 8, 10, 20, 30, 40, 50, or 60 mg/mL of enzyme can be employed in a reaction. A reaction herein can comprise one, two, or more beta-1,3-glucan phosphorylase enzymes, for example. In some aspects, only one or two beta-1,3-glucan phosphorylase enzymes is/are comprised in a reaction. A reaction composition herein can be, and typically is, cell-free (e.g., no whole cells present).

A reaction composition can be contained within any vessel (e.g., an inert vessel/container) suitable for applying one or more reaction conditions disclosed herein. An inert vessel in some aspects can be of stainless steel, plastic, or glass (or comprise two or more of these components) and be of a size suitable to contain a particular reaction. An inert vessel can optionally be equipped with a stirring device. A reaction composition in some aspects can be comprised within a product/application; production of beta-1,3-glucan in such aspects can optionally be characterized as in situ production. In situ produced beta-1,3-glucan typically is not subject to any downstream isolation process, but can be if desired. Any of the foregoing features, for example, can be used to characterize an isolated reaction herein.

Completion of a reaction in some aspects can be determined visually (e.g., no more accumulation of insoluble product), and/or by measuring the remaining amount of substrate(s) (alpha-G1P and/or acceptor) in the reaction (e.g., no more decrease in substrate levels over time). A reaction herein can be conducted for about, or at least about, 0.5, 1, 2, 4, 6, 8, 10, 12, 14, 16, 18, 20, 22, 24, 36, 48, 60, 72, 96, 120, 144, or 168 hours, for example.

Embodiments of the present disclosure also concern a method for producing beta-1,3-glucan, comprising:
  (a) contacting at least water, alpha-G1P, an acceptor molecule, and a beta-1,3-glucan phosphorylase enzyme comprising an amino acid sequence that is at least 90% identical to SEQ ID NO:2, SEQ ID NO:4, SEQ ID NO:6, SEQ ID NO:8, SEQ ID NO:10, or SEQ ID NO:12, wherein beta-1,3-glucan is produced; and
  (b) optionally, isolating the beta-1,3-glucan produced in step (a).

The contacting step in a method herein of producing beta-1,3-glucan can optionally be characterized as providing an enzymatic reaction as presently disclosed, which comprises at least water, alpha-G1P, an acceptor molecule, and a beta-1,3-glucan phosphorylase enzyme. Thus, any feature of an enzymatic reaction composition herein likewise characterizes a beta-1,3-glucan production method as presently disclosed.

The contacting step in a beta-1,3-glucan production method can be performed in any number of ways. For example, a desired amount of alpha-G1P and/or acceptor can first be dissolved in water (optionally, other components may also be added at this stage of preparation, such as buffer components), followed by addition of one or more beta-1,3-glucan phosphorylase enzymes. The reaction may be kept still, or agitated (e.g., via stirring or orbital shaking), for example.

In some aspects, isolating beta-1,3-glucan can include at least conducting a step of centrifugation, filtration, fractionation, chromatographic separation, dialysis, evaporation, and/or dilution. Isolation of insoluble beta-1,3-glucan can include at least conducting a centrifugation or filtration step, for example, and can optionally further comprise washing the centrifuged and/or filtered beta-1,3-glucan one, two, or more times with water or other aqueous liquid. A wash volume can optionally be at least about 10-100% of the volume of the reaction composition used to produce the beta-1,3-glucan. Washing can be done by various modes, as desired, such as by displacement or re-slurry washing. Isolation herein can optionally further comprise drying beta-1,3-glucan, and/or preparing an aqueous composition comprising insoluble beta-1,3-glucan (e.g., dispersion).

An isolated beta-1,3-glucan product herein, as provided in a dry form, can comprise no more than 2.0, 1.5, 1.0, 0.5, 0.25, 0.10, 0.05, or 0.01 wt % water, for example. In some aspects, a beta-1,3-glucan product is provided in an amount of at least 1 gram (e.g., at least 2.5, 5, 10, 25, 50, 100, 250, 500, 750, or 1000 g); such an amount can be a dry amount, for example.

Beta-1,3-glucan herein that has been isolated (optionally characterized as "purified") can be present in a composition at a wt % (dry weight basis) of about 100%, or at least about 50%, 60%, 70%, 80%, 85%, 90%, 91%, 92%, 93%, 94%, 95%, 96%, 97%, 98%, 98.5%, 99%, 99.5%, 99.8%, or 99.9%, for example. Such isolated beta-1,3-glucan itself can be used as an ingredient/component in a product/application, if desired.

Alpha-G1P for performing a beta-1,3-glucan production method herein can be provided directly via addition of isolated alpha-G1P (e.g., alpha-G1P obtained from a commercial source), for example. Alternatively, alpha-G1P can be supplied by providing at least a second reaction, wherein the products of the second reaction comprise alpha-G1P (i.e., the second reaction produces alpha-G1P as a product).

A second reaction for providing alpha-G1P in some aspects produces alpha-G1P by contacting (i) water, (ii) inorganic phosphate, (iii) a disaccharide, oligosaccharide, or polysaccharide (all of which comprise one or more glucose monomeric units), and (iv) a phosphorylase that phosphorolyzes the disaccharide, oligosaccharide, or polysaccharide. A phosphorylase in this aspect is an example of an alpha-G1P-producing enzyme herein. The monomeric units of a disaccharide, oligosaccharide, or polysaccharide substrate in a second reaction can be all glucose, or at least 30%, 40%, 50%, 60%, 70%, 80%, or 90% glucose, for example. The glycosidic linkages between the monomeric units can be alpha- and/or beta-linkages, and can be one type of, or more than one type of, the following linkages: 1,1; 1,2; 1,3; 1,4; and/or 1,6. A disaccharide or trisaccharide is typically employed in a second reaction herein.

Examples of a suitable phosphorylase as an alpha-G1P-producing enzyme herein include starch phosphorylase, sucrose phosphorylase and cellodextrin phosphorylase. In the presence of at least water and inorganic phosphate, these enzymes, respectively, convert starch (optionally debranched with a starch debranching enzyme such as pullulanase and/or isoamylase), sucrose, and cellodextrin (optionally prepared by treating cellulose with one or more beta-1,4-endoglucanases such as cellulase and/or endo-beta-1,4-glucanase, and optionally further with a lytic polysaccharide monooxygenase and/or cellobiohydrolase) to products including alpha-G1P. Any of these enzymes can have a plant, microbial (e.g., bacterial), or fungal (e.g., yeast) origin, for example. Examples of starch phosphorylase are disclosed in Patent Appl. Publ. No. 2002/0133849 and Tiwari and Kumar (2012, *Biotechnol. Mol. Biol. Rev.* 7:69-83), which are incorporated herein by reference. Examples of sucrose phosphorylase are disclosed in U.S. Pat. Nos. 5,716,837, 7,229,801 and 7,968,309, which are incorporated herein by reference. A sucrose phosphorylase in some aspects can be derivable from a *Leuconostoc* species (e.g., *L. mesenteroides*). Examples of cellodextrin phosphorylases are disclosed in U.S. Pat. No. 8,889,379, and U.S. Patent Appl. Publ. Nos. 2014/0087435, 2014/0057323, 2013/0059340 and 2017/0327857, which are incorporated herein by reference.

An acceptor molecule for performing a beta-1,3-glucan production method herein can be provided via direct addition of an isolated acceptor (e.g., acceptor obtained from a commercial source), for example. Alternatively, an acceptor molecule can be supplied by providing at least a third reaction, wherein the products of the third reaction comprise the acceptor molecule (i.e., the third reaction produces the acceptor molecule as a product). A third reaction typically comprises at least a phosphorylase that is not a beta-1,3-glucan phosphorylase, G1P (e.g., alpha-G1P) and a suitable acceptor for the phosphorylase. For example, a third reaction can be comprise laminaribiose phosphorylase, alpha-G1P and glucose, which serves as the acceptor for laminaribiose phosphorylase; such a third reaction produces laminaribiose (as well as phosphate). This laminaribiose product can then serve as an acceptor in a first reaction comprising beta-1,3-phosphorylase and alpha-G1P. As another example, a third reaction can comprise cellobiose phosphorylase, alpha-G1P and glucose; such a third reaction produces cellobiose (as well as phosphate), which can serve as an acceptor in a first reaction herein. While the foregoing disclosure relates to alternative ways of providing acceptors for beta-1,3-glucan phosphorylases as presently disclosed, this way of providing acceptors can likewise be applied when employing any beta-1,3-glucan phosphorylase. Examples of other beta-1,3-glucan phosphorylases in such embodiments further include those from *Euglena* species (e.g., *E. gracilis*, GENBANK Acc. No. AUO30192.1), *Ochromonas* species (e.g., *O. danica*, GENBANK Acc. No. BAU78234.1), *Fervidobacterium* species (e.g., *F. pennivorans*, GENBANK Acc. No. BAU78236.1) and *Paenibacillus* species (e.g., *P. polymyxa*, GENBANK Acc. No. BAU78235.1) (all of which GENBANK accession numbers are incorporated herein by reference), or an amino acid sequence that is at least about 90%, 91%, 92%, 93%, 94%, 95%, 96%, 97%, 98%, or 99% identical to any of the sequences of these GENBANK accession numbers and that have beta-1,3-glucan phosphorylase activity. Reactions and methods employing any other beta-1,3-glucan phosphorylase can have any of the features of a reaction/method as disclosed herein.

An acceptor-producing phosphorylase (e.g., laminaribiose phosphorylase, cellobiose phosphorylase) for a third reaction herein can have a plant, microbial (e.g., bacterial), or fungal (e.g., yeast) origin, for example. A laminaribiose phosphorylase in some aspects can be derivable from a *Paenibacillus* species. Examples of a laminaribiose phosphorylase are disclosed in Kitakoa et al. (2012, *Biosci. Biotechnol. Biochem.* 76:343-348; 1993, *Arch. Biochem. Biophys.* 304:508-514) and Nihira et al. (2012, *Carb. Res.* 361:49-54), which are incorporated herein by reference. Examples of a cellobiose phosphorylase are disclosed in Hamura et al. (2012, *Biosci. Biotechnol. Biochem.* 76:812-818) and Reichenbecher et al. (1997, *Eur. J. Biochem.* 247:262-267), which are incorporated herein by reference.

A second reaction and/or third reaction in some aspects can be provided in the same vessel in which a beta-1,3-glucan phosphorylase enzymatic reaction (first reaction) is performed, and can optionally be characterized as a "coupled reaction" (such aspects include in situ reaction compositions as disclosed above, for example). Alternatively, a second reaction and/or third reaction can be performed outside of (separate from) the vessel in which a first reaction is performed. A second reaction and/or third reaction can be performed before and/or continuously with a first reaction, for example. The conditions (e.g., time, temperature, pH) of a second reaction and/or third reaction herein can be as disclosed for a first reaction, for example. In some aspects, (i) only first and second reactions are performed, (ii) only first and third reactions are performed, or (iii) first, second and third reactions are performed. When all three reactions (as in [iii]) are performed as a coupled reaction, it is possible in some aspects that (A) the phosphate product of the first reaction and/or third reaction can be advantageously used by the second reaction, and/or (B) the alpha-G1P product of the second reaction can be advantageously used by the third reaction (in addition to being used by the first reaction).

Embodiments of the present disclosure also concern a method of processing beta-1,3-glucan, comprising:
  (a) providing an aqueous composition comprising up to about 40 wt % insoluble beta-1,3-glucan having a DP of at least 17;
  (b) heating the aqueous composition to at least about 75° C., thereby dissolving the beta-1,3-glucan in the aqueous composition to provide a solution;
  (c) subjecting the solution to at least one process that reduces the content (level or concentration) of one or more solutes other than the dissolved beta-1,3-glucan, thereby increasing the content (level or concentration) of the dissolved beta-1,3-glucan in the solution on a dry weight basis; and
  (d) optionally cooling the solution to a temperature at which the beta-1,3-glucan precipitates back to an insoluble state, and optionally further isolating the precipitated beta-1,3-glucan.

A method of processing beta-1,3-glucan can alternatively be characterized as a method of refining, purifying, preparing, or treating beta-1,3-glucan, if desired.

In typical embodiments, an aqueous composition comprising up to about 40 wt % insoluble beta-1,3-glucan can be provided by performing a beta-1,3-glucan synthesis reaction/method as disclosed herein. Alternatively, an aqueous composition comprising up to about 40 wt % insoluble beta-1,3-glucan can be provided, for example, by isolating beta-1,3-glucan from a biological source (e.g., plant, protist, fungus, bacteria) (and optionally hydrolyzing the isolated beta-1,3-glucan to reduce its molecular weight), or synthesizing beta-1,3-glucan in vitro using a beta-1,3-glucan synthase (synthetase) (e.g., see Miyamoto and Tamari, 1973, *Agr. Biol. Chem.* 37:1253-1260, incorporated herein by reference). The aqueous composition is non-caustic. An aqueous composition entered into in a processing method herein can comprise about, or up to about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 wt % insoluble beta-1,3-glucan, for example. In some aspects, an aqueous composition comprises about 5-40, 5-35, 5-30, 2-25, 5-20, 10-40, 10-35, 10-30, 10-25, 10-20, 15-40, 15-35, 15-30, 15-25, 15-20, 20-40, 20-35, 20-30, 20-25, 25-40, 25-35, 25-30, 30-40, 30-35, or 35-40 wt % insoluble beta-1,3-glucan. An aqueous composition entered into in a processing method herein can comprise solutes such as one or more sugars (e.g., a monosaccharide such as fructose and/or glucose; a disaccharide such as sucrose, laminaribiose, and/or cellobiose) and/or other molecules (e.g., buffer components, inorganic compounds such as phosphate), for example. An aqueous composition herein can be in the form of a paste or gel, and be white in color, for example.

A method of processing herein is directed to processing an aqueous composition that comprises insoluble beta-1,3-glucan with a DP of at least 17. DP examples of 17 and above are disclosed herein. In some aspects, the DP is 17 or 18 to 20, 21, 22, 23, 24, 25, 26, 27, 28, 29, or 30 (or any DP herein between 17 and 30). Insoluble beta-1,3-glucan in a processing method is typically linear.

A method of processing as presently disclosed comprises step (b) of heating an aqueous composition to at least about 75° C. to dissolve insoluble beta-1,3-glucan therein, thereby converting the aqueous composition to a solution. Heating can be to a temperature of about, at least about, or no more than about, 75, 76, 77, 78, 79, 80, 81, 82, 83, 84, 85, 86, 87, 88, 89, 90, 91, 92, 93, 94, 95, 96, 97, 98, 99, or 100° C., for example. Heating in some aspects can be to about 75-100, 75-95, 75-90, 75-88, 75-86, 78-100, 78-95, 78-90, 78-88, 78-86, 80-100, 80-95, 80-90, 80-88, 80-86, 82-100, 82-95, 82-90, 82-88, 82-86, 84-100, 84-95, 84-90, 84-88, or 84-86° C. Heating can optionally be accompanied by agitation of the aqueous composition (e.g., stirring or shaking). Upon dissolving beta-1,3-glucan, the aqueous composition becomes a solution that typically is water-like in feel and consistency (handles similarly to water). The solution typically is clear/transparent, whereas the aqueous composition prior to beta-1,3-glucan dissolution is not transparent (hazy, opaque, and/or white [e.g., opaque white]).

In some aspects, heating an aqueous composition in step (b) provides an aqueous composition with a complex viscosity of about 3 to 125 mPa (millipascals). The complex viscosity of a heated composition can be about, or less than about, 125, 120, 115, 110, 105, 104, 103, 102, 101, 100, 99, 98, 97, 96, 95, 90, 80, 70, 60, 50, 40, 30, 20, 15, 14, 13, 12, 11, 10, 9, 8, 7, 6, 5, 4, 2, or 1 mPa, for example. Also for example, the complex viscosity of a heated composition can be about 2-20, 2-15, 2-10, 5-20, 5-15, 5-10, 7-20, 7-15, 7-10, 90-105, 90-103, 90-100, 95-105, 95-103, 95-100, 97-105, 97-103, or 97-100 mPa. In some aspects, the complex viscosity of an aqueous herein as measured at about 55-65° C. (e.g., 60° C.) can decrease by about, or at least about, 95%, 96%, 97%, 98%, 99%, 99.5%, 99.8%, or 99.9%, when heated to a temperature of about 80-100, 85-100, or 90-100° C. (e.g., or any temperature listed above of 80° C. or higher). Complex viscosity in some aspects can be measured at a frequency (optionally constant frequency) of about 3-7, 4-6, or 5 Hz, and/or using a rotational rheometer (e.g., Kinexus® rheometer, Malvern Instruments) optionally with plate-on-plate geometry in oscillatory mode. Complex viscosity in some aspects can be measured according to Franck (2004, Understanding rheology of structured fluids, *Book of TA instruments*, pp. 1-11), Franck (2003, *Ann. Trans. Nordic Rheol. Soc.* 11:95-100), or U.S. Pat. No. 9,932,503 or 9,913,876, which are all incorporated herein by reference.

Step (c) of a method of processing herein subjects the solution to at least one process that reduces the content (level/concentration) of one or more solutes other than the dissolved beta-1,3-glucan, thereby increasing the content (level/concentration) of the dissolved beta-1,3-glucan in the solution on a dry weight basis. The temperature at which this processing is done is typically at least 75° C. (or any temperature as applied in step [b]). This processing step can comprise nanofiltration and/or ultrafiltration, for example. One can select a filtration approach and/or filtration pore size, as appropriate, based on the molecular weight of the beta-1,3-glucan being processed. Suitable nanofiltration or ultrafiltration methods contemplated to be applicable herein include those disclosed by Catarino et al. (2008, *J. Membrane Science* 312:34-40), Machado et al. (2016, *J. Food Eng.* 180:120-128), U.S. Patent Appl. Publ. No. 2017/0166938 and U.S. Pat. Nos. 6,454,946, 5,254,174, 5,403,604 and 9,909,119, which are all incorporated herein by reference. It is contemplated that processing step (c) completely removes (to below detection level), or partially removes (e.g., at least about 85%, 90%, 95%, 99%, or 99.5% by weight of original amount of solute is removed), one or more of solutes (e.g., see above) aside from the dissolved beta-1,3-glucan, for example. In some aspects, it is contemplated that processing step (c) increases the content of the dissolved beta-1,3-glucan in the solution on a dry weight basis by about, or at least about, 5%, 10%, 15%, 20%, 25%, 30%, 35%, 40%, 45%, or 50%.

A method of processing as presently disclosed optionally further comprises step (d) of cooling the solution (that was subject to processing in step [c]) to a temperature at which the beta-1,3-glucan precipitates back to an insoluble state, and optionally isolating the precipitated beta-1,3-glucan. Cooling can bring the temperature down to any temperature disclosed herein between 5° C. and 50° C. (e.g., 20-25° C.), for example. Cooling can be done any in any number of ways, including, for example, refrigeration, incubation in a cold water bath, using a circulating cold water jacket, and/or adding cold water to the solution. The precipitated beta-1, 3-glucan can optionally be isolated as described above for isolating insoluble beta-1,3-glucan following its enzymatic synthesis.

In some alternative aspects, a method can instead comprise above steps (a), (b) and (d) (where step [d] cooling and/or isolation is optional); removal of one or more solutes (by step [c]) in such alternative aspects is also optional, and typically is not performed. Any of the above other features of a beta-1,3-glucan refining method can characterize such alternative aspects, for example. Thus, an example of such an alternative aspect herein is a method of processing, handling, manipulating, or controlling beta-1,3-glucan, comprising:

(a) providing an aqueous composition comprising up to about 40 wt % insoluble beta-1,3-glucan having a DP of at least 17;

(b) heating the aqueous composition to at least about 75° C., thereby dissolving the beta-1,3-glucan in the aqueous composition; and (c) optionally cooling the aqueous composition to a temperature at which the beta-1,3-glucan precipitates back to an insoluble state.

In some of these alternative aspects, step (c) of cooling is performed; such a method can be used, for example, to prepare a product/application in which the beta-1,3-glucan provides texture and/or thickening to the product/application. The thermoreversibility/thermoshifting exhibited by beta-1,3-glucan in aqueous compositions of these aspects facilitates production of such products/applications. Products/applications produced by this method are thus also disclosed.

In some further alternative aspects, step (b) of heating can instead be conducted at a temperature of about, at least about, or no more than about, 31, 32, 33, 34, 35, 36, 37, 38, 39, 40, 31-40, 31-39, 31-38, 31-37.5, 36-40, 36-39, 36-38, 36-37.5, 36.5-38, 36.5-37.5, 37-38, or 37-37.5° C. (e.g., human/mammal body temperature such as normal or febrile), for example. Heating can be conducted, for example, by exposure to (contacting with) an external human/mammal body surface (e.g., skin, nails, hair), a human/mammal body orifice (e.g., oral cavity, nasal cavity, aural cavity, rectal cavity, genitourinary tract), or an internal human/mammal surface/organ (e.g., alimentary canal, respiratory system). An aqueous composition in such further alternative aspects can comprise about, or up to about, 1, 2, 3, 4, 5, 6, 7, 8, 9, 10, 11, 12, 13, 14, 15, 16, 17, 18, 19, 20, 1-20, 1-10, 1-8, 1-5, 1-3, 2-20, 2-10, 2-8, 2-5, 2-3, 4-20, 4-10, 4-8, 4-5, 8-20, or 8-10 wt % insoluble beta-1,3-glucan herein, for example. Other features of such further alternative aspects can be any of those as disclosed above, such as complex viscosity (after heating step [b]) and/or beta-1,3-glucan DP, for example. Such further alternative aspects can optionally be characterized as a method of handling, manipulating, controlling, or tactile sensing (feeling) of beta-1,3-glucan. Various aqueous products/applications can take advantage of the thermoreversibility/thermoshifting characteristics exhibited by aqueous compositions of beta-1,3-glucan in these further alternative aspects, such as products that generate, evoke, or stimulate human/mammal tactile response/sensitivity/sensing (e.g., where tactile response is stimulated by a change in beta-1,3-glucan solution state [e.g. undissolved to dissolved]). Thus, an example of such a further alternative aspect herein is a method of handling, manipulating, controlling, or tactile sensing (feeling) of beta-1,3-glucan, comprising:

(a) providing an aqueous composition comprising up to about 20 wt % insoluble beta-1,3-glucan having a DP of at least 17;

(b) heating the aqueous composition to at least about 31-40° C., thereby dissolving the beta-1,3-glucan in the aqueous composition; and (c) optionally cooling the aqueous composition to a temperature at which the beta-1,3-glucan precipitates back to an insoluble state.

Therefore, products/applications for practicing such a method (e.g., steps [a] and [b]) are also disclosed.

Non-limiting examples of compositions and methods disclosed herein include:

1. A reaction composition comprising at least water, alpha-G1P, an acceptor molecule, and a beta-1,3-glucan phosphorylase enzyme comprising an amino acid sequence that is at least 90% identical to SEQ ID NO:2, SEQ ID NO:4, SEQ ID NO:6, SEQ ID NO:8, SEQ ID NO:10, or SEQ ID NO:12, wherein the enzyme synthesizes beta-1,3-glucan.

2. The reaction composition of embodiment 1, wherein the beta-1,3-glucan has at least about 90% beta-1,3 glycosidic linkages.

3. The reaction composition of embodiment 2, wherein the beta-1,3-glucan has at least about 99% beta-1,3 glycosidic linkages.

4. The reaction composition of embodiment 1, 2, or 3, wherein the degree of polymerization (DP) of the beta-1,3-glucan is at least 3.
5. The reaction composition of embodiment 4, wherein the DP of the beta-1,3-glucan is at least about 15.
6. The reaction composition of embodiment 1, 2, 3, 4, or 5, wherein the acceptor molecule comprises a monosaccharide, disaccharide, or oligosaccharide.
7. The reaction composition of embodiment 6, wherein the acceptor molecule comprises laminaribiose.
8. The reaction composition of embodiment 1, 2, 3, 4, or 5, wherein the acceptor molecule comprises a polysaccharide.
9. The reaction composition of embodiment 8, wherein the polysaccharide comprises beta-glucan.
10. The reaction composition of embodiment 9, wherein the beta-glucan comprises laminarin.
11. A method for producing beta-1,3-glucan (e.g., as produced in a reaction composition of any of embodiments 1-10), the method comprising: (a) contacting at least water, alpha-G1P, an acceptor molecule, and a beta-1,3-glucan phosphorylase enzyme comprising an amino acid sequence that is at least 90% identical to SEQ ID NO:2, SEQ ID NO:4, SEQ ID NO:6, SEQ ID NO:8, SEQ ID NO:10, or SEQ ID NO:12, wherein beta-1,3-glucan is produced; and (b) optionally, isolating the beta-1,3-glucan produced in step (a).
12. The method of embodiment 11, wherein the alpha-G1P is provided in step (a) by providing a second reaction, wherein the products of the second reaction comprise alpha-G1P.
13. The method of embodiment 12, wherein the second reaction is provided in the same vessel in which step (a) is performed, and wherein the second reaction is performed before and/or continuously with step (a).
14. The method of embodiment 12 or 13, wherein the second reaction produces alpha-G1P by contacting (i) water, (ii) inorganic phosphate, (iii) a glucose-comprising disaccharide, oligosaccharide, or polysaccharide, and (iv) a phosphorylase that phosphorolyzes the disaccharide, oligosaccharide, or polysaccharide.
15. The method of embodiment 11, 12, 13, or 14, wherein the acceptor molecule is provided in step (a) by providing a third reaction, wherein the products of the third reaction comprise the acceptor molecule.
16. The method of embodiment 15, wherein the acceptor molecule provided by the third reaction is laminaribiose.
17. A method of processing beta-1,3-glucan, the method comprising: (a) providing an aqueous composition comprising up to about 40 wt % insoluble beta-1,3-glucan having a degree of polymerization (DP) of at least 17 (optionally by practicing a reaction composition of any of embodiments 1-10 or a method of any of embodiments 11-16); (b) heating the aqueous composition to at least about 75° C., thereby dissolving the beta-1,3-glucan in the aqueous composition to provide a solution; (c) subjecting the solution to at least one process that reduces the content of one or more solutes other than the dissolved beta-1,3-glucan, thereby increasing the content of the dissolved beta-1,3-glucan in the solution on a dry weight basis; and (d) optionally cooling the solution to a temperature at which the beta-1,3-glucan precipitates back to an insoluble state, and optionally isolating the precipitated beta-1,3-glucan.
18. The method of embodiment 17, wherein the process of (c) comprises nanofiltration and/or ultrafiltration.

EXAMPLES

The present disclosure is further exemplified in the following Examples. It should be understood that these Examples, while indicating certain aspects herein, are given by way of illustration only. From the above discussion and these Examples, one skilled in the art can ascertain the essential characteristics of the disclosed embodiments, and without departing from the spirit and scope thereof, can make various changes and modifications to adapt the disclosed embodiments to various uses and conditions.

Example 1

Cloning and Expression of Putative Beta-1,3-Glucan Phosphorylases

This Example describes cloning and expression of various putative beta-1,3-glucan phosphorylase enzymes.

The amino acid sequences of six putative beta-1,3-glucan phosphorylases were identified. These enzymes were denoted as PstGp1 (SEQ ID NO:2), GmaGp1 (SEQ ID NO:4), PspGp2 (SEQ ID NO:6), CauGp1 (SEQ ID NO:8), CgrGp1 (SEQ ID NO:10), and LphGp1 (SEQ ID NO:12). The respective SEQ ID numbers for the native genetic coding sequences of these enzymes are listed in Table 1. An alignment of the amino acid sequence of each of these enzymes was made against the GENBANK database via a BLAST search on the National Center for Biotechnology Information (NCBI) website. Table 2 (below) lists database sequences provided by each alignment with at least 90% amino acid identity to the respective query sequence.

TABLE 2

Sequences Provided by BLAST Alignment of PstGp1, GmaGp1, PspGp2, CauGp1, CgrGp1 and LphGp1 Amino Acid Sequences Against the GENBANK Database

| Enzyme Name | SEQ ID NO.[c] | Origin | Aligning Database Sequence(s)[a] (% Identity[b]) (Annotation)[d] |
|---|---|---|---|
| PstGp1 | 2 | Paenibacillus stellifer DSM 14472 | WP_038698858.1 (100%) ("hypothetical protein"). Next aligning hit only 60% identical. |
| GmaGp1 | 4 | Gorillibacterium massiliense G5 | WP_040952469.1 (100%) ("hypothetical protein"). Next aligning hit only 73% identical. |
| PspGp2 | 6 | Paenibacillus sp. FSL H8-237 | ETT58856.1 (100%) ("hypothetical protein"). WP_036682608.1 (100%) ("hypothetical protein"). Accession Nos for sequences that are 93-99% identical and disclose either "hypothetical protein" or "cellobiose phosphorylase": WP_036682608.1, WP_076147384.1, WP_076101331.1, WP_038568482.1, WP_076273097.1, WP_076223429.1, |

TABLE 2-continued

Sequences Provided by BLAST Alignment of PstGp1, GmaGp1, PspGp2, CauGp1, CgrGp1 and LphGp1 Amino Acid Sequences Against the GENBANK Database

| Enzyme Name | SEQ ID NO.[c] | Origin | Aligning Database Sequence(s)[a] (% Identity[b]) (Annotation)[d] |
|---|---|---|---|
| | | | WP_076215068.1, WP_094902051.1, OME55357.1, WP_076185206.1, WP_076218937.1, WP_076203607.1, WP_076302337.1, WP_076304336.1, WP_076276013.1, WP_076306494.1, WP_076278898.1, WP_076282331.1, WP_076124547.1, WP_076142080.1, WP_076310029.1, WP_076134883.1, WP_076192770.1, OMD57475.1, OMD33815.1, OMD65572.1, OMD71492.1, OMD92517.1, OME27446.1, OME03079.1, OMC64708.1, OME05948.1, OMD80815.1, OME20601.1, OMC77182.1, OMD82535.1, WP_076300120.1, WP_076285201.1, WP_042184448.1, WP_094878231.1, WP_076116623.1, WP_094874192.1, WP_081953976.1, WP_060626728.1, OMD44475.1, WP_039834362.1. Next aligning hit only 80% identical. |
| CauGp1 | 8 | *Caloramator australicus* RC3 | WP_008909277.1 (100%) ("hypothetical protein"). Next aligning hit only 80% identical. |
| CgrGp1 | 10 | *Clostridium grantii* DSM 8605 | WP_073338818.1 (100%) ("cellobiose phosphorylase"). Next aligning hit only 59% identical. |
| LphGp1 | 12 | *Lachnoclostridium phytofermentans* KNHs2131 | WP_029501686.1 (100%) ("hypothetical protein"). Next aligning hit only 85% identical. |

[a]GENBANK database Accession Number is provided for each aligning sequence.
[b]Percent identity of aligning sequence to entire query sequence or at least a 98% portion thereof.
[c]Query sequence used in alignment against GENBANK database sequences.
[d]Annotation provided in respective GENBANK Accession Number.

Nucleic acid sequences encoding PstGp1 (SEQ ID NO:2), GmaGp1 (SEQ ID NO:4), PspGp2 (SEQ ID NO:6), CauGp1 (SEQ ID NO:8), CgrGp1 (SEQ ID NO:10) and LphGp1 (SEQ ID NO:12) were each optimized for expression in *Escherichia coli*. Specifically, codon-optimized nucleic acid sequences were synthesized and individually inserted into expression vector pET30a (Novagen, Madison, Wis.) at NdeI and XhoI sites by Generay Biotech Co. (Shanghai, China), resulting in expression plasmids. Each insertion into pET30a resulted in a sequence (under a LacI-regulated T7 promoter) encoding a putative beta-1,3-phosphorylase (same amino acid sequence as above) followed by two extra amino acids (Leu-Glu) (resulting from the XhoI site) and a 6×His-tag at the C-terminus. The PstGp1, GmaGp1, PspGp2, CauGp1, CgrGp1 and LphGp1 amino acid sequences as encoded by each pET30a construct were SEQ ID NOs:14, 16, 18, 20, 22 and 24, respectively; the respective SEQ ID numbers for the genetic coding sequences of these amino acid sequences are listed in Table 1.

Each expression plasmid was individually transformed into *E. coli* BL21(DE3) pLysS (Novagen) and the transformation mixes were spread onto Luria agar plates supplemented with 50 ppm kanamycin and 30 ppm chloramphenicol. Colonies carrying correct expression plasmids, as confirmed by polymerase chain reaction (PCR) and sequencing analyses, were inoculated into 5 mL Luria broth supplemented with 50 ppm kanamycin and 30 ppm chloramphenicol and then incubated at 37° C. with shaking for about 24 hours. To induce expression from the pET30a construct in each transformant, about 1 mL of each culture was inoculated to 25 mL of MagicMedia™ (Thermo Fisher Scientific) supplemented with 50 ppm kanamycin and 30 ppm chloramphenicol and then incubated at 37° C. with shaking for 24 hours.

Cells were harvested by centrifugation after the protein expression induction period, after which the cell pellet was resuspended in lysis buffer (50 mM Tris pH 7.0, 500 mM NaCl, 10% glycerol, 0.1% TWEEN-20) and lysed on ice via ultra-sonication for 10 min (35% power, 20 min, 2 s on/2 s off) (SCIENT2-II D, Ningbo Scientz Biotechnology Co., LTD). The lysates were then cleared by centrifugation at 13000 rpm for 30 min (BECKMAN COULTER, Avanti J-E). The clarified lysates were individually applied onto a HisTrap™ HP (5-mL) histidine-tagged protein purification column (GE Healthcare) pre-equilibrated with 50 mM Tris pH 7.0, 500 mM NaCl and 10% glycerol. The target protein was eluted from the column with a linear gradient from 0 to 250 mM imidazole in equilibration buffer. The fractions containing target protein were pooled, concentrated and buffer-exchanged to equilibration buffer using Amicon ULTRA ultrafiltration (10 kDa cutoff) devices, and stored in 40% glycerol at −20° C. until usage. Each purified target protein was then analyzed for beta-1,3-glucan phosphorylase activity and product formation, as described in Examples 2 and 3 below.

Example 2

Analysis of Phosphorylase Activity of PstGp1, GmaGp1, PspGp2, CauGp1, CgrGp1 and LphGp1

This Example describes measuring the phosphorylase activity of the putative beta-1,3-glucan phosphorylases expressed in Example 1, namely PstGp1, GmaGp1, PspGp2, CauGp1, CgrGp1 and LphGp1.

The phosphorylase activity of each of PstGp1 (SEQ ID NO:14), GmaGp1 (SEQ ID NO:16), PspGp2 (SEQ ID NO:18), CauGp1 (SEQ ID NO:20), CgrGp1 (SEQ ID NO:22) and LphGp1 (SEQ ID NO:24) was measured in 100-µL reactions in a 96-well plate format. Each reaction (water-based) was incubated at 37° C. for 30 minutes and comprised about 4 ppm of one of the foregoing proteins, 10 mM alpha-G1P (alpha-D-glucose-1-phosphate disodium salt hydrate, Sigma-Aldrich, product no. G7000), 1 mM cellobiose (D-[+]-cellobiose, Sigma-Aldrich, product no. C7252) as the initial acceptor, and 60 mM Tris-HCl buffer, pH 7.0. Phosphorus release from each reaction was quantified using PiBlue™ reagent (BioAssay Systems, Hayward, Calif.). One unit of phosphorylase activity was defined as the amount of enzyme that releases 1 µmol of inorganic phosphorus per minute under the above test conditions. Each of the tested proteins had phosphorylase activity, indicating that they could add glucose (derived from alpha-G1P) to the cellobiose acceptor while releasing free phosphate. The extended product (i.e., cellobiose extended at its non-reducing end by one glucose monomer) likely itself served as an acceptor for ongoing phosphorylase activity.

Glucose, p-nitrophenyl beta-D-glucopyranoside, and laminarin were also separately tested for acceptor function using this assay. It was found that p-nitrophenyl beta-D-glucopyranoside (1 mM) and laminarin (5 mg/mL), but not glucose (1 mM), could each function as acceptors.

Based on these results, PstGp1 (SEQ ID NO:2), GmaGp1 (SEQ ID NO:4), PspGp2 (SEQ ID NO:6), CauGp1 (SEQ ID NO:8), CgrGp1 (SEQ ID NO:10) and LphGp1 (SEQ ID NO:12) are considered to have phosphorylase activity. These results are striking in view of Table 2, which shows that PstGp1, GmaGp1, CauGp1 and LphGp1 were previously characterized only as "hypothetical proteins", and that PspGp2 and CgrGp1 might have been considered to have cellobiose phosphorylase activity. Cellobiose phosphorylase enzymes are known to reversibly convert cellobiose into glucose and alpha-G1P. The present data suggest that PstGp1 (SEQ ID NO:2), GmaGp1 (SEQ ID NO:4), PspGp2 (SEQ ID NO:6), CauGp1 (SEQ ID NO:8), CgrGp1 (SEQ ID NO:10) and LphGp1 (SEQ ID NO:12) are able to recognize and extend certain acceptor compounds, as indicated by free phosphate release.

Example 3

Beta-1,3-Glucan Production by PstGp1, GmaGp1, PspGp2, CauGp1, CgrGp1 and LphGp1 Phosphorylases This Example describes reactions that produce linear beta-1,3-glucan using PstGp1, GmaGp1, PspGp2, CauGp1, CgrGp1 and LphGp1 phosphorylases, thereby confirming that each of these phosphorylases is a beta-1,3-glucan phosphorylase.

Alpha-G1P was provided in the reactions of this Example (below) by way of the activity of sucrose phosphorylase on sucrose (sucrose phosphorylase, using free phosphate, converts sucrose to fructose and alpha-G1P). Laminaribiose served as an initial acceptor compound for each of PstGp1, GmaGp1, PspGp2, CauGp1, CgrGp1, or LphGp1; laminaribiose was extended (at its non-reducing end) by each of these phosphorylases to produce beta-1,3-glucan with a degree of polymerization (DP) of 3. Beta-1,3-glucan (DP3 and higher) itself was also extended (at its non-reducing end) by each of PstGp1, GmaGp1, PspGp2, CauGp1, CgrGp1, or LphGp1 to produce beta-1,3-glucan with higher DP. The laminaribiose initial acceptor was provided in these reactions by way of the activity of laminaribiose phosphorylase on alpha-G1P (provided by the sucrose phosphorylase) and glucose (directly provided), both of which substrates are used by laminaribiose phosphorylase to produce laminaribiose and free phosphate.

Individual coupled reactions as described immediately above were conducted to test each of the PstGp1, GmaGp1, PspGp2, CauGp1, CgrGp1, and LphGp1 phosphorylases. Each 1-L reaction (water-based) was conducted at 37° C. in a solution initially containing 100 mM sodium phosphate buffer at pH 7.0, 200 g/L sucrose, 1 g/L glucose, 4 mg/L of a *Leuconostoc mesenteroides* sucrose phosphorylase (Sigma-Aldrich, product no. S0937), 1 mg/L of a *Paenibacillus* laminaribiose phosphorylase (as disclosed in Kitakoa et al., 2012, *Biosci. Biotechnol. Biochem.* 76:343-348, which is incorporated herein by reference), and 4 mg/L one of the PstGp1, GmaGp1, PspGp2, CauGp1, CgrGp1, or LphGp1 phosphorylases. After 1-2 days incubation, insoluble glucan began to precipitate in each of the reactions. Each reaction was continued for an additional 3-5 days for complete conversion, at which time there was no more accumulation of insoluble glucan.

The following steps were taken to refine the insoluble glucan produced in each reaction. First, the insoluble glucan was collected from each reaction by centrifugation at 10,000 rpm for 20 minutes, after which the supernatant was removed leaving behind a wet pellet containing about 75 wt % water (about 25 wt % solids). The pellets were opaque white and each resembled a paste. Each pellet (about 400-500 mL) was then heated to 85° C. in a water bath, resulting in liquefication of the pellet (i.e., dissolution of the insoluble beta-1,3-glucan into the aqueous phase of the pellet) after about 5-10 minutes (separate experiments showed that heating at 80° C. also resulted in pellet liquefication). Each liquefied pellet, now a solution, had a water-like feel and consistency, and was clear/transparent with a yellowish hue. Cold water was then added to a total volume of 1 L, which resulted in precipitation of the insoluble glucan. The precipitated insoluble glucan was then washed twice with water, using the same volume of water as used in the precipitation step. It is contemplated that the ease in which the insoluble glucan (about 25 wt % solids in water) could be dissolved at an elevated temperature to a water-like state allows for ready application of certain liquid processing of the dissolved glucan. For example, nanofiltration or ultrafiltration could be applied to remove sugars (monosaccharides and/or disaccharides) that might be present.

Further work was performed to explore the water-like consistency of heated samples of beta-1,3-glucan synthesized by the above phosphorylases. Viscosity transitions of samples were measured using a Kinexus® rotational rheometer (Malvern Instruments) with plate-on-plate geometry in oscillatory mode (constant frequency of 5 Hz as a function of temperature). For example, it was found that, for beta-1,3-glucan (17 wt % in water) produced by phosphorylase PspGp2, the complex viscosity (measured according to Franck, 2004, Understanding rheology of structured fluids, *Book of TA instruments*, pp. 1-11, incorporated herein by reference) changed from about 10000 mPa at 60° C. to about 10 mPa at 95° C. Similarly, for beta-1,3-glucan (28 wt % in water) produced by phosphorylase CgrGp1, the complex viscosity changed from about 100000 mPa at 60° C. to about 100 mPa at 95° C. These measured viscosity transitions were quite dramatic, corresponding well with visual observations of these samples changing from non-flowing pastes to low viscosity fluids.

The glycosidic linkage profile of each washed insoluble glucan product was then analyzed by NMR (nuclear magnetic resonance, $^1$H 600-MHz NMR, in 3% LiCl/DMSO with DSS/D$_2$O added, 80° C.). The linkages of each product were found to be 100% beta-1,3. Thus, the insoluble glucan products of each of the disclosed PstGp1, GmaGp1, PspGp2, CauGp1, CgrGp1 and LphGp1 phosphorylases were linear beta-1,3-glucan. SEC (size-exclusion chromatography) analysis (using Aminex® HPX-42A column, water eluent, 0.6 mL/min flow rate, 85° C., RI detector) showed that these linear beta-1,3-glucan products had a DP of about 17 or 18.

The results of the present Example are striking in view of Table 2, which shows that PstGp1, GmaGp1, CauGp1 and LphGp1 were previously characterized only as "hypothetical proteins", and that PspGp2 and CgrGp1 might have been considered to have cellobiose phosphorylase activity. The present data show that PstGp1 (SEQ ID NO:2), GmaGp1 (SEQ ID NO:4), PspGp2 (SEQ ID NO:6), CauGp1 (SEQ ID NO:8), CgrGp1 (SEQ ID NO:10) and LphGp1 (SEQ ID NO:12) are each able to synthesize linear beta-1,3-glucan using alpha-G1P and laminaribiose as initial substrates. PstGp1, GmaGp1, PspGp2, CauGp1, CgrGp1 and LphGp1 phosphorylases, therefore, are beta-1,3-glucan phosphorylases. The results of the present Example are further striking, since the amino acid sequences of these beta-1,3-glucan phosphorylases appear to have at most about 25%, 43%, 63%, and 50% sequence identity, respectively, with beta-1,3-glucan phosphorylase amino acid sequences from *Euglena gracilis* (GENBANK Acc. No. AUO30192.1), *Ochromonas danica* (GENBANK Acc. No. BAU78234.1), *Fervidobacterium pennivorans* (GENBANK Acc. No. BAU78236.1), and *Paenibacillus polymyxa* (GENBANK Acc. No. BAU78235.1), which are believed to be representative of the only previously disclosed beta-1,3-glucan phosphorylase amino acid sequences. It is also notable that the beta-1,3-glucan products of the disclosed reactions—linear with a DP of 17 or 18—were aqueous-insoluble. This observation contrasts with other disclosures (e.g., Legentil et al., 2015, *Molecules* 20:9745-9766; Mishima et al., 2009, *J. Biol. Chem.* 284:28687-28697; Yamamoto et al., 2013, *Biosci. Biotechnol. Biochem.* 77:1949-1954; Ogawa et al., 1973, *Carbohydr. Res.* 29:397-403) indicating that linear beta-1,3-glucan products with a DP less than 20 are aqueous-soluble.

Thus, beta-1,3-glucan can be synthesized in a reaction comprising at least water, alpha-G1P, a suitable acceptor molecule such as laminaribiose, and a beta-1,3-glucan phosphorylase enzyme comprising SEQ ID NO:2, SEQ ID NO:4, SEQ ID NO:6, SEQ ID NO:8, SEQ ID NO:10, or SEQ ID NO:12. It is notable that aqueous compositions of this Example comprising insoluble beta-1,3-glucan products were easily converted with heating to water-like compositions, which are contemplated to be amenable to one or more processing steps that, for example, reduce the level of non-beta-1,3-glucan component(s) (e.g., sugars) in the composition.

What is claimed is:

1. A reaction composition comprising at least water, alpha-glucose-1-phosphate (alpha-G1P), an acceptor molecule, and a beta-1,3-glucan phosphorylase enzyme comprising an amino acid sequence that is at least 95% identical to SEQ ID NO: 6,
wherein said amino acid sequence has beta-1,3-glucan phosphorylase activity,
wherein the acceptor molecule (i) comprises one or more glucose monomeric units, (ii) does not consist of glucose, and (iii) has one or more glycosidic linkages,
wherein the beta-1,3-glucan phosphorylase enzyme synthesizes a beta-1,3-glucan in the reaction composition and the reaction composition is cell-free.

2. The reaction composition of claim 1, wherein the beta-1,3-glucan has at least about 90% beta-1,3 glycosidic linkages.

3. The reaction composition of claim 2, wherein the beta-1,3-glucan has at least about 99% beta-1,3 glycosidic linkages.

4. The reaction composition of claim 1, wherein the degree of polymerization (DP) of the beta-1,3-glucan is at least 3.

5. The reaction composition of claim 4, wherein the DP of the beta-1,3-glucan is at least about 15.

6. The reaction composition of claim 1, wherein the acceptor molecule comprises a monosaccharide, disaccharide, or oligosaccharide.

7. The reaction composition of claim 6, wherein the acceptor molecule comprises laminaribiose.

8. The reaction composition of claim 1, wherein the acceptor molecule comprises a polysaccharide.

9. The reaction composition of claim 8, wherein the polysaccharide comprises beta-glucan.

10. The reaction composition of claim 9, wherein the beta-glucan comprises laminarin.

11. A method for producing beta-1,3-glucan, said method comprising:
contacting at least water, alpha-glucose-1-phosphate (alpha-G1P), an acceptor molecule, and a beta-1,3-glucan phosphorylase enzyme comprising an amino acid sequence that is at least 95% identical to SEQ ID NO: 6,
wherein said amino acid sequence has beta-1,3-glucan phosphorylase activity,
wherein the acceptor molecule (i) comprises one or more glucose monomeric units, (ii) does not consist of glucose, and (iii) has one or more glycosidic linkages,
wherein a beta-1,3-glucan is produced, and
wherein the contacting step is performed under cell-free conditions.

12. The method of claim 11, wherein said alpha-G1P is provided in the contacting step by providing a second reaction, wherein the products of the second reaction comprise alpha-G1P.

13. The method of claim 12, wherein the second reaction is provided in the same vessel in which the contacting step is performed, and wherein the second reaction is performed before and/or continuously with the contacting step.

14. The method of claim 12, wherein the second reaction produces alpha-G1P by contacting (i) water, (ii) inorganic phosphate, (iii) a glucose-comprising disaccharide, oligosaccharide, or polysaccharide, and (iv) a phosphorylase that phosphorolyzes the disaccharide, oligosaccharide, or polysaccharide.

15. The method of claim 11, wherein said acceptor molecule is provided in the contacting step by providing a third reaction, wherein the products of the third reaction comprise said acceptor molecule.

16. The method of claim 15, wherein said acceptor molecule provided by the third reaction is laminaribiose.

17. The method of claim 11, further comprising isolating the beta-1,3-glucan produced in the contacting step.

18. The method of claim 11, wherein the amino acid sequence is at least 97% identical to SEQ ID NO:6.

19. The method of claim 11, wherein the amino acid sequence is at least 98% identical to SEQ ID NO:6.

20. The reaction composition of claim 6, wherein the acceptor molecule comprises cellobiose or p-nitrophenyl beta-D-glucopyranoside.

21. The reaction composition of claim 1, wherein the amino acid sequence is at least 97% identical to SEQ ID NO:6.

22. The reaction composition of claim 1, wherein the amino acid sequence is at least 98% identical to SEQ ID NO: 6.

23. The reaction composition of claim 1, wherein amino acid sequence is at least 99% identical to SEQ ID NO: 6.

24. The reaction composition of claim 1, wherein the amino acid sequence is at least 99.5% identical to SEQ ID NO: 6.

* * * * *